US005981259A

United States Patent [19]
Franzusoff

[11] Patent Number: 5,981,259
[45] Date of Patent: Nov. 9, 1999

[54] CD4+ T-LYMPHOCYTE PROTEASE GENES AND INHIBITORS THEREOF

[75] Inventor: Alex Franzusoff, Denver, Colo.

[73] Assignee: University Technology Corporation, Boulder, Colo.

[21] Appl. No.: 08/976,838

[22] Filed: Nov. 24, 1997

Related U.S. Application Data

[63] Continuation-in-part of application No. 08/368,852, Feb. 5, 1995, Pat. No. 5,691,183, and application No. 08/525,940, Sep. 8, 1995, Pat. No. 5,866,351, which is a continuation-in-part of application No. 08/368,852, and application No. 08/340,185, Nov. 15, 1994, Pat. No. 5,830,463, which is a continuation-in-part of application No. 08/088,322, Jul. 7, 1993, Pat. No. 5,413,914, said application No. 08/368,852, is a continuation-in-part of application No. 08/088,322.

[51] Int. Cl.$^6$ ............................ C12N 15/74; C12N 15/80; C12N 15/85; A61K 31/70

[52] U.S. Cl. .................... 435/235.1; 435/325; 435/252.3; 514/44; 536/24.5

[58] Field of Search .......................... 536/24.5; 435/325, 435/252.3, 235.1; 514/44

[56] References Cited

U.S. PATENT DOCUMENTS

| | | | |
|---|---|---|---|
| 4,929,553 | 5/1990 | Bussey et al. | 435/172.3 |
| 5,077,204 | 12/1991 | Brake et al. | 435/68.1 |
| 5,162,220 | 11/1992 | Oshima et al. | 435/224 |
| 5,225,537 | 7/1993 | Foster | 530/380 |
| 5,234,830 | 8/1993 | Oshima et al. | 435/252.3 |
| 5,413,914 | 5/1995 | Franzusoff | 435/23 |

FOREIGN PATENT DOCUMENTS 2024277  3/1991  Canada .

OTHER PUBLICATIONS

Anderson et al., 1993, *J. Biol. Chem.*, 268(33):24887–24891.
Angliker, 1993, *Biochem. J.*, 293:75–81, Part 1.
Ashorn, et al., 1990 *Proc. Natl. Acad. Sci. USA*, 87:7472–7476.
Baker, et al., 1988 *Cell*, 54:335–344.
Baldari, et al., 1985 *Gene*, 35:27–32.
Barr, et al., 1991 *DNA & Cell Biol.*, 10(5):319–328.
Barr, et al.,. 1988 *J. Biol. Chem.*, 263(31):16471–16478.
Barr, 1991 *Cell*, 66:1–3.
Bathurst, et al., 1989 *J. Virol.*, 63(7):3176–3179.
Berman, et al., 1988, *J. Virol.*, 62(9):3135–3142.
Bizzini et al., 1990, *FEMS Microbiol. Immunol.*, 64:155–168.
Bosch, et al., 1989, *Science*, 244:694–697.
Bosch, et al., 1990, *J. Virol.*, 64(5):2337–2344.
Bourdette et al., 1994, *J. Immunol.*, 152:2510–2519.
Brake, et al., 1984, *Proc. Natl. Acad. Sci. USA*, 81:4642–4646.
Brennan, et al., 1988, *FEBS Lett.*, 229(1):167–170.
Brenner, et al., 1992, *Proc. Natl. Acad. Sci. USA*, 89:922–926.
Bresnahan, et al., 1990, *J. Cell Biol.*, 111:2851–2859.
Chan, et al., 1983, *J. Bacteriol.*, 155(2):903–906.
Chou et al., 1994, *J. Immunol.*, 152:2520–2529.
Cohen, 1994, *Science*, 264:1839.
Cohen, 1994, *Science*, 264:1660.
Copeland, et al., 1986, *J. Cell Biol.*, 103:1179–1191.
Davies et al., 1992, *Nucleic Acids Res.*, 20(11):2693–2698.
Decroly et al., 1994, *J. Biol. Chem.*, 269(16):12240–12247.
Demmer et al., 1993, *J. Immunol.*, 150(12):5371–5378.
Dewar, et al., 1989, *J. of Virol.*, 63(6):2452–2456.
Dreyer, et al., 1989, *Proc. Natl. Acad. Sci. USA*, 86:9752–9756.
Dreyer, et al., 1992, *Biochem.*, 31:6646–6659.
Earl, et al., 1991, *J. Virol.*, 65(1):31–41, 65(4):2047–2055.
Egel–Mitani, 1990, *Yeast*, 6:127–137.
Einfeld, et al., 1988, *Proc. Natl. Acad. Sci. USA*, 85:8688–8692.
Engelhardt et al., 1994, *Hum. Gene Ther*, 5:1217–1229.
Fattal–German et al., 1992, *Develop. Biol. Standard.*, 77:115–120.
Fisher, et al., 1988, *J. Biol. Chem.*, 263(32):16515–16518.
Fitting, et al., 1982, *J. Biol. Chem.*, 257(23):14011–14017.
Franzusoff et al., 1995, *J. Biol. Chem.*, 270(7):3154–3159.
Franzusoff, 1992, *Seminars Cell Biol.*, 3:309–324.
Franzusoff, et al., 1991, *J. of Cell Biol.*, 112(1):27–37.
Franzusoff, et al., 1989, *EMBO J.*, 8(9):2695–2702.
Freed, et al., 1990, *Proc. Natl. Acad. Sci. USA*, 87:4650–4654.
Freed, et al., 1992, *Proc. Natl. Acad. Sci. USA*, 89:70–74.
Fuller, et al., 1989, *Proc. Natl. Acad. Sci. USA*, 86:1434–1438.
Fuller, et al., 1989, *Science*, 246:482–486.
Garcia–Blanco, et al., 1991, *Science*, 254:815–820.
Garten, et al., 1989, *Virol.*, 172:25–31.
Gnirke et al., 1991, *EMBO J.*, 10(7):1629–1634.
Gobin et al., 1995, *Gene*, 163:27–33.
Göttlinger, et al., 1989, *Proc. Natl. Acad. Sci. USA*, 86:5781–5785.
Graham, et al., 1991, *J. Cell Biol.*, 114(2):207–218.
Guy, et al., 1991, *J. Virol.*, 65(3):1325–1331.
Haffar, et al., 1990, *J. Virol.*, 64(6):3100–3103.
Hakes et al., 1991, *Endocrinology*, 129(6):3053–3063.
Hallenberger et al., 1992, *Nature*, 360:358–361.
Haseltine, 1991, *FASEB J.*, 5:2349–2360.
Hatsuyama et al., 1994, *Plant Cell Physiol.*, 35(1):93–98.

(List continued on next page.)

*Primary Examiner*—Charles L. Patterson, Jr.
*Attorney, Agent, or Firm*—Sheridan Ross P.C.

[57] ABSTRACT

The present invention includes the identification and isolation of a nucleic acid molecule encoding a dibasic amino acid processing endoprotease from CD4+ T-lymphocytes as well as a protein encoded by that nucleic acid molecule. The present invention also includes related nucleic acid molecules and proteins encoded by such nucleic acid molecules as well as recombinant molecules and recombinant cells that include nucleic acid molecules of the present invention. The present invention also includes use of such nucleic acid molecules and proteins to develop therapeutic compositions that enhance or inhibit dibasic amino acid processing endoprotease activity.

41 Claims, 4 Drawing Sheets

OTHER PUBLICATIONS

Hatsuzawa, et al., 1990, *J. Biol. Chem.*, 265(36):22075–22078.
Hattori, et al., 1989, *FEBS Lett.*, 248(1,2):48–52.
Horitmoto et al., 1994, *J. Virol.*, 68(9):6074–6078.
Hosaka, et al., 1991, *J. Biol. Chem.*, 266(19):12127–12130.
Inocencio, et al., 1993, *J. Virol.*, 67(1):593–595.
Johnston, et al., 1993, *Science*, 260:1286–1293.
Julius, et al., 1984, *Cell*, 37:1075–1089.
Julius, et al., 1983, *Cell*, 32:839–852.
Keränen, 1986, *Gene*, 48:267–275.
Ketner et al., 1994, *Proc. Natl. Acad. Sci. USA*, 91:6186–6190.
Kiefer et al., 1991, *DNA and Cell Biol.*, 10(10):757–769.
Kowalski, et al., 1991, *Virol.*, 65(1):281–291.
Kowalski, et al., 1987, *Science*, 237:1351–1355.
Kozarsky, et al., 1989, *J. Acq. Immun. Def. Syn.*, 2(2):163–169.
Kramer, et al., 1986, *Science*, 231:1580–1584.
Kuroda, et al., 1992, *J. Biol. Chem.*, 267(3):1953–1961.
Kwang, et al., 1988, *J. Virol.*, 62(5):1774–1780.
Lapatto, et al., 1989, *Nature*, 342:299–302.
Legrain, et al., 1989, *Gene*, 79:227–237.
Leibowitz, et al., 1976, *Proc. Natl. Acad. Sci. USA*, 73(6):2061–2065.
Lusson et al., 1993, *Proc. Natl. Acad. Sci. USA*, 90:6691–6695.
Machida, et al., 1982, *J. Biol. Chem.*, 257(23):14018–14022.
Manetta, et al., 1992, *Anal. Biochem.*, 202:10–15.
Markie et al., 1993, *Somat. Cell Mol. Genet.*, 19(2):161–169.
Matayoshi, et al., 1990, *Science*, 247:954–958.
McCune, et al., 1988, *Cell*, 53:55–67.
Meek, et al., 1990, *Nature*, 343:90–92.
Miller, et al., 1989, *Science*, 246:1149–1152.
Mitsuya, et al., 1991, *FASEB J.*, 5:2369–2380.
Mitsuya, et al., 1990, *Science*, 249:1533–1544.
Mizuno, et al., 1989, *Biochem Biophys. Res. Comm.*, 164(2):780–787.
Mizuno, et al., 1988, *Biochem Biophys. Res. Comm.*, 156(1):246–254.
Moehring, et al., 1993, *J. Biol. Chem.*, 268(4):2590–2594.
Montefiori, et al., 1988, *Proc. Natl. Acad. Sci. USA*, 85:9248–9252.
Morikawa et al., 1993, *J. Virol.*, 67(6):3601–3604.
Morrison, et al., 1985, *J. Virol.*, 53(3):851–857.
Moulard et al., 1994, *Eur. J. Biochem.*, 225:565–572.
Moulard et al., 1994, *FEBS Lett.*, 338:281–284.
Moulard et al., 1993, In *Int. Conf. AIDS*, 9(1):155 (abstract No. PO–A08–0123).
Mullen et al., 1994, *Plant Physiol.*, 105:113 (Abstr. 606).
Nakagawa et al., 1993, *J. Biochem.*, 113:132–135.
Nakagawa et al., 1993, *FEBS Lett.*, 327(2):165–171.
Nara, et al., 1988, *Nature*, 332:469–470.
Navia, et al., 1989, *Nature*, 337:615–620.
Oda, 1991, *Biochem. Biophys. Res. Comm.*, 179(3):1181–1186.
Owens, 1991, *Biochem. Biophys. Res. Comm.*, 181(1):402–408.
Pachnis et al., 1990, *Proc. Natl. Acad. Sci. USA*, 87:5109–5113.
Perez, et al., 1987, *J. Virol.*, 61(5):1609–1614, 61(10):2981–2988.
Peterson et al., 1993, *Proc. Natl. Acad. Sci. USA*, 90:11207–11211.
Pichuantes, et al., "Expression of Heterologous Gene Products in Yeast", Chapter 8 in *Principles and Practice of Protein Engineering*, in press, 1993, (J.L. Cleland & C. Craik, eds.), Hauser Publ.
Pichuantes, et al., 1990, *J. Biol. Chem.*, 265(23):13890–12898.
Pinter, et al., 1989, *J. Virol.*, 63(6):2674–2679.
Pique, et al., 1992, *J. Virol.*, 66(2):906–913.
Rabinovich et al., 1994, *Science*, 265:1401–1404.
Renneisen, et al., 1990, *J. Biol. Chem.*, 265(27):16337–16342.
Roberts, et al., 1990, *Science*, 248:358–361.
Robey, et al. 1985, *Science*, 228:593–595.
Sanchez–Pescador, et al., 1985, *Science*, 227:484–492.
Scheid, et al., 1974, *Virol.*, 57:475–490.
Scheid, et al., 1976, *Virol.*, 69:265–277.
Seidah et al., 1994, *Biochim.*, 76:197–209.
Seidah et al., 1990, *DNA and Cell Biol.*, 9(6):415–424.
Shen, et al., 1989, *Gene*, 84:303–309.
Smeekens, et al., 1991, *Proc. Natl. Acad. Sci. USA*, 88:340–344.
Smeekens, et al., 1990, *J. Biol. Chem.*, 265(6):2997–3000.
Sodroski, et al., 1986, *Nature*, 322:470–474.
Starcich et al., 1986, *Cell*, 45:637–648.
Stein, et al., 1990, *J. Biol. Chem.*, 265(5):2640–2649.
Steiner et al., pp. 23435–23438, 1992, *J. Biol. Chem.*, vol. 267, No. 33.
Stern et al., 1992, *Cell*, 68:465–477.
Stevenson, et al., 1990, *J. Virol.*, 64(8):3792–3803.
Stieneke–Gröber, et al., 1992, *EMBO J.*, 11(7):2407–2414.
Suda et al., 1993, *Cell*, 75:1169–1178.
Thim, et al., 1986, *Proc. Natl. Acad. Sci. USA*, 83:6766–6770.
Thomas, et al., 1988, *Science*, 241:226–229.
Valenzuela, et al., 1982, *Nature*, 298:347–350.
Veronese, et al., 1985, *Science*, 229:1402–1405.
Vonèche, et al., 1992, *Proc. Natl. Acad. Sci. USA*, 89:3810–3814.
Walker, et al., 1987, *Proc. Natl. Acad. Sci. USA*, 84:8120–8124.
Wen, et al., 1986, *Proc. Natl. Acad. Sci. USA*, 83:3639–3643.
Wen, et al., 1986, *Virol.*, 153:150–154.
Wickner et al., 1976, *Genetics*, 82:429–442.
Wilcox, et al., 1991, *J. Cell Biol.*, 115(2):297–307.
Willey, et al., 1988, *Proc. Natl. Acad. Sci. USA*, 85:9580–9584.
Wills, et al., 1984, *J. Cell Biol.*, 99:2011–2023.
Wise, et al., 1990, *Proc. Natl. Acad. Sci. USA*, 87:9378–9382.
Wlodawer, et al., 1989, *Science*, 245:616–621.
Zinkernagel, et al., 1991, *Nature*, 354:433.

CD4+ T-LYMPHOCYTE PROTEASE GENES AND INHIBITORS THEREOF

CROSS-REFERENCE TO RELATED APPLICATIONS

The present application is a continuation-in-part of U.S. patent application Ser. No. 08/525,940, entitled "CD4+ T-Lymphocyte Proteases and Genes Encoding said Proteases", filed Sep. 8, 1995, issued as U.S. Pat. No. 5,866,351 on Feb. 2, 1999, and a continuation-in-part of U.S. patent application Ser. No. 08/368,852, entitled "CD4+ T-Lymphocyte Proteases and Genes Encoding said Proteases", filed Jan. 5, 1995, which issued as U.S. Pat. No. 5,691,183, on Nov. 25, 1997, both of which are incorporated herein by reference in their entireties. Ser. No. 08/525,940,. U.S. Pat. No. 5,866,351 is a continuation-in-part of Ser. No. 08/368,852, U.S. Pat. No. 5,691,183, which is a continuation-in-part of U.S. patent application Ser. No. 08/088,322, entitled "Yeast Assay to Identify Inhibitors of Dibasic Amino Acid Processing Endoproteases", filed Jul. 7, 1993, which issued as U.S. Pat. No. 5,413,914, on May 9, 1995. Ser. No. 08/525,940, U.S. Pat. No. 5,866,351 is also a continuation-in-part of U.S. patent application Ser. No. 08/340,185, entitled "Yeast-Based Delivery Vehicles", filed Nov. 15, 1994, which issued as U.S. Pat. No. 5,830,463 on Nov. 3, 1998. Ser. No. 08/340,185, U.S. Pat. No. 5,830, 463 is a continuation-in-part of Ser. No. 08/088,322 U.S. Pat. No. 5,413,914.

GOVERNMENT SUPPORT

This invention was made at least in part with government support under Grant No. AI 34747, awarded by the National Institute of Allergy and Infectious Diseases, National Institutes of Health. The government has certain rights to this invention.

FIELD OF THE INVENTION

The present invention is directed to novel dibasic amino acid processing endoprotease genes, to novel proteins encoded by such genes, and to novel inhibitors of such genes. More particularly, the present invention is directed to a novel human CD4+ T-lymphocyte dibasic amino acid processing endoprotease gene, to proteins encoded by that gene. The present invention also includes use of such genes and proteins to develop therapeutic compositions that enhance or inhibit dibasic amino acid processing endoprotease activity.

BACKGROUND OF THE INVENTION

A number of enveloped viruses, including retroviruses, hepatitis viruses, herpes viruses, orthomyxoviruses and paramyxoviruses, produce precursor envelope glycoproteins that require cleavage by a cellular dibasic amino acid processing endoprotease as one step in the process of envelope glycoprotein maturation. As precursor envelope glycoproteins are being synthesized, they are directed into the host cell secretory pathway for transport to the cell surface. As the precursor proteins move through the pathway, they are subjected to a variety of post-translational events including glycosylation and proteolytic cleavage (see, for example, Stein et al., 1990, *J. Biol. Chem.* 265, 2640–2649). The precursor human immunodeficiency virus (HIV) envelope protein gp160, for example, is co-translationally glycosylated and subsequently cleaved into gp120 and gp41 by a cellular dibasic amino acid processing endoprotease that apparently is localized in the Golgi apparatus. The gp120 and gp41 proteins are further glycosylated prior to reaching the infected cell surface. Cleavage of the HIV gp160 protein has been shown to be necessary for membrane fusion, syncytium formation and viral infectivity (see, for example, McCune et al., 1988, *Cell* 53, 55–67; Kowalski et al., 1987, *Science* 237, 1351–1355).

Although the genes encoding several dibasic amino acid processing endoproteases (also referred to as subtilisin-like protein convertases) have been isolated (see, for example, Barr, 1991, *Cell* 66, 1–3; Hakes et al., 1991, *Endocrinology* 129, 3053–3063; Kiefer et al., 1991, *DNA and Cell Biology* 10, 757–769; Lusson et al., 1993, *Proc. Natl. Acad. Sci. USA* 90, 6691–6695; Steiner et al., 1992, *J. Biol. Chem.* 267, 23435–23438, Nakagawa et al., 1993, *J. Biochem.* 113, 132–Nakagawa et al., 1993, *FEBS Lett.* 327, 165–171; Tsuji, et al., 1994, *Biochem. Biophys. Res. Commun.* 202, 1452–1459; Decroly et al., 1996, *J. Biol. Chem.* 271, 30442–30450), a number of cellular dibasic amino acid processing endoproteases remain to be identified, including CD4+ T-lymphocyte dibasic amino acid processing endoproteases responsible for cleaving the precursor envelope proteins of lentiviruses and lymphotropic viruses into envelope proteins, such as the enzyme that cleaves HIV gp160 into gp120 and gp41 in vivo. There is a need to identify cellular dibasic amino acid processing endoproteases that are responsible for in vivo cleavage of targeted substrates. Investigators have shown, for example, that the extent of proteolytic cleavage is a function of the sequence of amino acids at the dibasic amino acid processing site and of the dibasic amino acid processing endoprotease for hormones such as insulin and renin (see, for example, Oda et al., 1991, *Biochem. Biophys. Res. Comm.* 179, 1181–1186; Thim et al., 1986, *Proc. Natl. Acad. Sci. USA* 83, 6766–6770.

Nucleoside analogs are currently in use as antiviral drugs, particularly for treating retroviral infections as the analogs can inhibit the ability of the retroviral reverse transcriptase enzyme to make a DNA copy of the incoming viral RNA. For example, HIV infections are being treated with AZT (3'1-azidothymidine), ddI (2'3'-dideoxyinosine), ddC (2'3'-dideoxycytidine), and d4T (didehydrothymidine). Nucleoside analogs, however, have short half-lives and can exhibit substantial side effects. In addition, viruses often develop resistance to the nucleoside analog within a short period time of its administration.

Non-nucleoside inhibitors of HIV reverse transcriptase, such as TIBO (tetrahydro-imidazo(4,5,1-jk)(1,4)-benzodiazepin-2(1H)-one), BI-RG-587 (11-cyclopropyl-7-methyl-dipyrido-(2,3-b:3'3'-f)1,4-diazepin-6H-5-one), pyridones, and bis(heteroaryl)piperazines, are also being developed and tested. Since these compounds are highly selective for the HIV reverse transcriptase enzyme, they apparently cause less severe side effects than do nucleoside analogs. Decreased sensitivity of HIV to these agents, however, also develops rapidly.

The HIV-encoded aspartyl protease that processes the gag and gag/pol polyproteins to yield the mature structural proteins and enzymes required for virion formation (p24, p17, p15, reverse transcriptase) has also been targeted as an enzyme against which to design antiviral agents. HIV protease inhibitors, at least theoretically, can inhibit HIV production by chronically infected cells and, as such, have an advantage over reverse transcriptase inhibitors that apparently can only block replication if added to cells before HIV infection. Peptide-based substrate analogs are being prepared and tested. One persistent drawback of HIV protease inhibitors is the emergence of HIV strains that are resistant to the inhibitor being administered.

Other strategies for inhibiting HIV infection that are being pursued include inhibition of other HIV-encoded proteins such as Tat, Rev, and integrase; blocking entry of the virus into the cell by, for example, soluble CD4 receptor molecules; targeted delivery of toxins to HIV-infected cells; inhibition of viral functions using antisense technology; and immune constitution protocols. Although several of these technologies are at the early stages of development, clinical trials conducted using some of these technologies have been disappointing. For a recent review of present and future strategies to treat HIV infection, see Johnston et al., 1993, *Science* 260, 1286–1293.

Most assays used to test antiviral drugs are either in vitro or mammalian cell culture assays, many relying on the use of infectious virus. Mammalian cell culture assays are usually costly, complex, time-consuming, and potentially dangerous if infectious virus is used. Recently, a Drosophila cell-based assay was developed for screening inhibitors of the HIV Rev protein. For a review of methods to identify HIV inhibitors, see Johnston et al., ibid.

Thus, there remains a need to identify antiviral drugs with improved efficacy that have fewer side effects than known drugs and against which an infected host is less likely to develop resistance. A preferred class of inhibitors to identify are those that can be used to treat infectious diseases, such as HIV infections, in which proliferation of the infectious agent depends on dibasic amino acid processing endoprotease cleavage. In order to identify such drugs in a rapid and straightforward manner, an improved assay is required that is less complex, less expensive, less time-consuming, and more selective than currently used methods. There is also a need to identify CD4+ T-lymphocyte dibasic amino acid processing endoproteases, such as the enzyme that cleaves HIV gp160 in vivo, in order to identify specific inhibitors having greater selectivity and, hence, fewer side effects.

SUMMARY OF THE INVENTION

The present invention includes the identification and isolation of a gene encoding a dibasic amino acid processing endoprotease from CD4+ T-lymphocytes as well as a protein encoded by that gene. The present invention also includes use of such genes and proteins in a number of applications, including use of proteins of the present invention to identify compounds that are particularly useful therapeutic compositions in that they can treat infectious diseases susceptible to inhibition of dibasic amino acid processing endoprotease activity with improved efficacy and with fewer side effects than compounds that are currently employed.

One embodiment of the present invention relates to an isolated nucleic acid molecule that selectively reduces the expression of a dibasic amino acid processing endoprotease hTCP gene by hybridizing to a nucleic acid molecule selected from the group of a dibasic amino acid processing endoprotease hTCP gene and transcription products thereof. Another embodiment of the present invention is an isolated nucleic acid molecule that is capable of hybridizing under stringent conditions with a regulatory region of a dibasic amino acid processing endoprotease gene comprising nhTCP.

The present invention also includes recombinant molecules that include nucleic acid molecules of the present invention operatively linked to a transcription control sequence as well as recombinant cells and recombinant viruses that include nucleic acid molecules of the present invention.

The present invention also includes a therapeutic composition capable of reducing the infectivity of an infectious agent susceptible to inhibition of dibasic amino acid processing endoprotease activity. Such a composition can include a nucleic acid molecule that selectively reduces the expression of a dibasic amino acid processing endoprotease hTCP gene by hybridizing to a nucleic acid molecule selected from the group consisting of a dibasic amino acid processing endoprotease hTCP gene and transcription products thereof and/or a compound that inhibits dibasic amino acid processing endoprotease activity, wherein the compound is identified by its ability to inhibit the activity of hTCP. A therapeutic composition of the present invention also includes an excipient.

Another embodiment of the present invention is a method to protect an animal from disease caused by an infectious agent susceptible to inhibition of dibasic amino acid processing endoprotease activity. The method includes the step of administering to the animal a therapeutic composition that includes a nucleic acid molecule that selectively reduces the expression of a dibasic amino acid processing endoprotease hTCP gene by hybridizing to a nucleic acid molecule selected from the group consisting of a dibasic amino acid processing endoprotease hTCP gene and transcription products thereof and/or a compound that inhibits dibasic amino acid processing endoprotease activity, wherein the compound is identified by its ability to inhibit the activity of hTCP.

Yet another embodiment of the present invention is a method to reduce the infectivity of an infectious agent susceptible to inhibition of dibasic amino acid processing endoprotease activity in an animal. The method includes contacting the dibasic amino acid processing endoprotease with a compound that selectively reduces the expression of a dibasic amino acid processing endoprotease hTCP gene.

Yet another embodiment of the present invention relates to a method to produce an animal model for studying the effect of TCP depletion. Such a method includes the steps of administering to the animal a composition that includes a nucleic acid molecule that selectively reduces the expression of a dibasic amino acid processing endoprotease TCP gene by hybridizing to a nucleic acid molecule selected from the group consisting of a dibasic amino acid processing endoprotease TCP gene and transcription products thereof and/or a compound that inhibits dibasic amino acid processing endoprotease activity, wherein the compound is identified by its ability to inhibit the activity of TCP.

Another embodiment of the present invention is a non-human animal model for studying the effects of TCP depletion. Such an animal model is a non-human animal to which a composition has been administered, such composition including a nucleic acid molecule that selectively reduces the expression of a dibasic amino acid processing endoprotease TCP gene by hybridizing to a nucleic acid molecule selected from the group consisting of a dibasic amino acid processing endoprotease TCP gene and transcription products thereof and/or a compound that inhibits dibasic amino acid processing endoprotease activity, wherein the compound is identified by its ability to inhibit the activity of TCP.

DETAILED DESCRIPTION OF THE INVENTION

Figure 1:
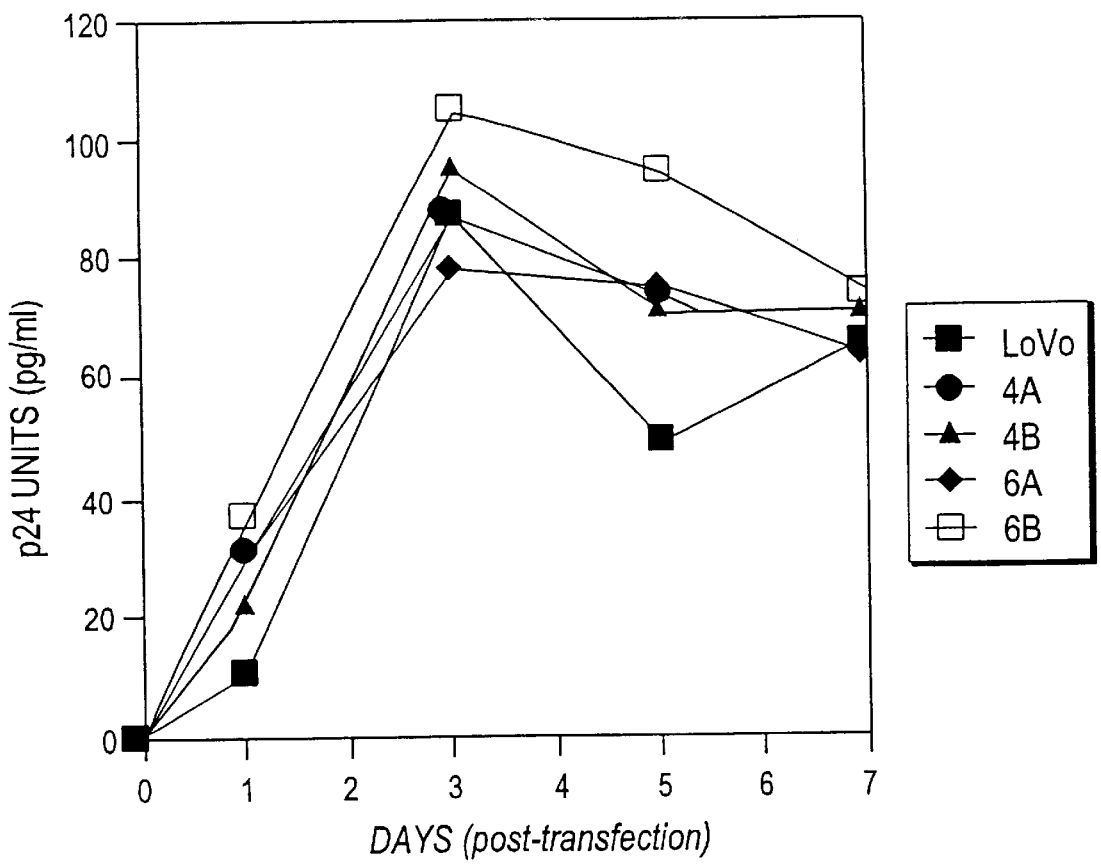
FIG. 1 is a graph showing results from a p24 ELISA which demonstrates that the cellular capacity for HIV-1 virion production by LoVo cells transfected with nhTCP antisense constructs.

The present invention includes the identification and isolation of a gene encoding a dibasic amino acid processing endoprotease from CD4+ T-lymphocytes as well as a protein encoded by that gene. Without being bound by theory, such a protein is believed to be the enzyme naturally responsible for the cleavage of precursor proteins having dibasic amino acid processing sites that are produced by CD4+ T-lymphocytes. Such precursor proteins include, but are not limited to, precursors of growth factors and other hormones as well as precursor proteins of infectious agents, such as immunodeficiency viruses that infect CD4+ T-lymphocytes. Genes and proteins of the present invention can be used in a number of applications, including those discussed below. Examples include the development of therapeutic compositions to reduce the infectivity of infectious agents having dibasic amino acid processing sites, to reduce excessive production of proteins that as precursors have dibasic amino acid processing sites and to enhance production of desired proteins, the precursors of which have dibasic amino acid processing sites.

The present invention also includes the surprising discovery that the dibasic amino acid processing endoprotease gene isolated from human CD4+ T-lymphocytes, as well as the protein encoded by that gene, is remarkably similar to mouse and rat PC5 genes and proteins (for sequences of rat and mouse PC5, also referred to as PC6 (e.g., PC6A and PC6B), genes and proteins, see Lusson et al. ibid., and Nakagawa et al., 1993, *FEBS Lett.*, ibid.). The present invention also includes the use of such nucleic acid molecules and proteins encoded therefrom, as well as other nucleic acid molecules that form stringent hybrids with the human gene of the present invention and proteins encoded therefrom, as therapeutic compositions and as tools to identify compounds that inhibit infection by infectious agents that are susceptible to inhibition of dibasic amino acid processing endoprotease activity. The inventors are not aware of any suggested or actual use of such molecules in such an embodiment.

The term dibasic amino acid processing endoprotease refers to any proteolytic enzyme that cleaves a precursor protein (also referred to as a proprotein) at a dibasic amino acid processing site within the precursor protein. Dibasic amino acid processing endoproteases are typically serine proteases of the subtilisin family (e.g. subtilisin-like protein convertases, or SPC), such as those described by Steiner et al., ibid.

The phrase dibasic amino acid processing site refers to a site on the precursor protein that can be cleaved by a dibasic amino acid processing endoprotease. Dibasic amino acid processing sites usually include at least one pair of basic amino acid residues that are substantially adjacent to each other. Suitable sites include, but are not limited to, Lys—Arg, Arg—Arg, Lys—Lys, Pro—Arg, Ala—Arg, Lys/Arg—X—Lys/Arg, and Lys/Arg—X—$X_1$—Lys/Arg (also referred to herein as SEQ ID NO:5), where "Lys" is lysine, "Arg" is arginine, "Pro" is proline, "Ala" is alanine, "X" is any amino acid, and "$X_1$" is preferably Lys, Arg, Ala or Pro. A particularly preferred dibasic amino acid processing site to target, particularly with inhibitory compounds of the present invention, is the Arg—Glu—Lys—Arg (also referred to herein as SEQ ID NO:6) site found in HIV gp160 precursor proteins, wherein "Glu" is glutamic acid.

The term precursor protein refers to a protein that undergoes post-translational modification during maturation, a process that includes at least one step of cleavage by a dibasic amino acid processing endoprotease at a dibasic amino acid processing site within the precursor protein to form at least one cleavage protein. The terms cleavage protein, cleaved protein, cleavage product, and cleaved product each refer to a protein that has been produced by proteolytic cleavage of a precursor protein, the cleavage being required, but not necessarily sufficient, for the protein to become mature and bioactive. It should be understood that cleavage proteins of the present invention can undergo additional post-translational maturation steps prior and/or subsequent to dibasic amino acid processing endoprotease cleavage. A precursor protein of the present invention can be a polyprotein such that the precursor protein contains more than one product which can be separated by cleavage with a dibasic amino acid processing endoprotease.

The present invention includes a number of novel nucleic acid molecules as well as the use of those and additional similar nucleic acid molecules in a variety of embodiments as disclosed herein. One embodiment of the present invention is an isolated nucleic acid molecule that includes the dibasic amino acid processing endoprotease gene nhTCP (defined below) and nucleic acid molecules that include fragments of that gene that encode a dibasic amino acid processing endoprotease having proteolytic activity. As used herein, the gene nhTCP includes all natural allelic variants of that gene. Methods to produce fragments and to identify those that encode proteins having proteolytic activity are known to those skilled in the art; examples are provided herein.

An isolated nucleic acid molecule of the present invention can include at least one of the following isolated nucleic acid molecules: a nucleic acid molecule that includes a nucleic acid sequence having at least about 86 percent nucleic acid sequence identity with SEQ ID NO:1; a nucleic acid molecule that includes a nucleic acid sequence having at least about 93 percent nucleic acid sequence identity with SEQ ID NO:3; a nucleic acid molecule that includes a nucleic acid sequence having at least about 86 percent nucleic acid sequence identity with SEQ ID NO:12; a nucleic acid molecule that includes a nucleic acid sequence having at least about 86 percent nucleic acid sequence identity with SEQ ID NO:14; and an isolated nucleic acid molecule having at least about 91% nucleic acid sequence identity with SEQ ID NO:19. As will be disclosed in further detail below, SEQ ID NO:1, SEQ ID NO:3, SEQ ID NO:12, SEQ ID NO:17 and SEQ ID NO:19 are each believed to include sequences encoding at least part of the catalytic domain (i.e., active site) of a dibasic amino acid processing endoprotease. As used herein, a catalytic domain can be as small as the minimal amount of nucleic acid sequence that is required to encode a dibasic amino acid processing endoprotease protein having proteolytic activity. As can be appreciated by those skilled in the art, such a domain can consist of contiguous or noncontiguous nucleic acid sequences.

Isolated nucleic acid molecules of the present invention can include isolated nucleic acid molecules that selectively reduce the expression of a dibasic amino acid processing endoprotease hTCP gene by hybridizing to a nucleic acid molecule selected from the group of a dibasic amino acid processing endoprotease hTCP gene and transcription products thereof. Isolated nucleic acid molecules of the present invention can also be nucleic acid molecules that include regions capable of hybridizing under stringent conditions with a regulatory region of the dibasic amino acid processing endoprotease gene nhTCP (i.e., with a region that controls expression of the gene hTCP, including the untranslated region (UTR) of an RNA molecule encoding hTCP).

A preferred isolated nucleic acid molecule of the present invention has at least about 75 percent, preferably at least about 80 percent, more preferably at least about 85 percent, and even more preferably at least about 90 percent nucleic acid sequence identity with nhTCP. As used herein, percent nucleic acid sequence identity refers to the percentage of identical sequences within corresponding regions of two nucleic acid molecules. Such regions can be of a size spanning from the minimal length required for two molecules to form a stringent hybrid to the entire gene.

The present invention also includes the use of any isolated nucleic acid molecule capable of hybridizing, under stringent conditions, with (i.e., to) a human CD4+ T-lymphocyte dibasic amino acid processing endoprotease gene referred to herein as nhTCP, or human T cell protease gene. As such, all of these nucleic acid molecules are also included in the present invention. Such nucleic acid molecules also include isolated nucleic acid molecules that selectively reduce the expression of a dibasic amino acid processing endoprotease hTCP gene by hybridizing to a nucleic acid molecule selected from the group consisting of a dibasic amino acid processing endoprotease hTCP gene and transcription products thereof. Such an isolated nucleic acid molecule can include a nucleic acid molecule that is capable of hybridizing with an nhTCP gene encoding any isoform of hTCP, including hTCPA and hTCPB. According to the present invention, the term "selectively reduce the expression of a dibasic amino acid processing endoprotease hTCP gene" refers to the ability of an isolated nucleic acid molecule to reduce the expression of an hTCP gene to a greater degree as compared to its ability to reduce the expression of another dibasic amino acid processing endoprotease gene, as measured by standard methods of determining nucleic acid molecule expression levels. Preferably, such an isolated nucleic acid molecule is able to reduce the expression of an hTCP gene without substantially reducing the expression of another dibasic amino acid processing endoprotease gene. More preferably, such an isolated nucleic acid molecule is able to reduce the expression of an hTCP gene without reducing the expression of any one other dibasic amino acid processing endoprotease gene by more than 50%, more preferably by more than 25%, and most preferably by more than 5%.

As used herein, the gene nhTCP includes all nucleic acid sequences related to a natural nhTCP gene, such as regulatory regions that control production of a human T cell dibasic amino acid processing endoprotease encoded by that gene (e.g., transcription, translation or post-translation control regions) as well as the coding region itself. The gene nhTCP of the present invention can be distinguished from other dibasic amino acid processing endoprotease genes in that nhTCP includes nhTCP$_{483}$, a cDNA (complementary DNA) nucleic acid molecule, the production of which is disclosed in the Examples, and the deduced nucleic acid sequence of the coding strand of which is presented herein as SEQ ID NO:1. The protein encoded by nhTCP$_{483}$, referred to herein as hTCP$_{161}$, has a deduced amino acid sequence presented herein as SEQ ID NO:2. (It should be noted that since nucleic acid and amino acid sequencing technologies are not entirely error-free, SEQ ID NO:1, as well as other SEQ ID NOs disclosed herein, represent, at best, apparent sequences of the respective nucleic acid molecules and proteins.) According to the present invention a transcription product of an hTCP gene includes all nucleic acid sequences related to a natural nhTCP mRNA transcript, such as regulatory regions that control translational or post-translational processes as well as the coding region itself. As such, transcription products include the untranslated regions (UTR's) of the RNA molecule. As used herein, stringent hybridization conditions refer to standard so hybridization conditions under which nucleic acid molecules, including oligonucleotides, are used to identify similar sequences. Stringent hybridization conditions typically permit isolation of nucleic acid molecules having at least about 70% nucleic acid sequence identity with the nucleic acid molecule being used as a probe in the hybridization reaction. Such standard conditions are disclosed, for example, in Sambrook et al., 1989, *Molecular Cloning: A Laboratory Manual,* Cold Spring Harbor Labs Press. The reference Sambrook et al., ibid., is incorporated by reference herein in its entirety. Examples of such conditions include, but are not limited to, the following: oligonucleotide probes of about 18–25 nucleotides in length with T$_n$'s ranging from about 50° C. to about 65° C., for example, can be hybridized to nucleic acid molecules typically immobilized on a filter (e.g., nitrocellulose filter) in a solution containing 5× SSPE, 1% Sarkosyl, 5× Denhardts and 0.1 mg/ml denatured salmon sperm DNA at 37° C. for about 2 to 12 hours. The filters are then washed 3 times in a wash solution containing 5× SSPE, 1% Sarkosyl at 37° C. for 15 minutes each. The filters can be further washed in a wash solution containing 2× SPE, 1% Sarkosyl at 37° C. for 15 minutes per wash. Randomly primed DNA probes can be hybridized, for example, to nucleic acid molecules typically immobilized on a filter (e.g., nitrocellulose filter) in a solution containing 5× SSPE, 1% Sarkosyl, 0.5% Blotto (dried milk in water), and 0.1 mg/ml denatured salmon sperm DNA at 42° C. for about 2 to 12 hours. The filters are then washed 2 times in a wash solution containing 5× SSPE, 1% Sarkosyl at 42° C. for 15 minutes each, followed by 2 washes in a wash solution containing 2× SSPE, 1% Sarkosyl at 42° C. for 15 minutes each. Further examples of such conditions are provided in the Examples section. It should be noted that the extent of identity required to form a stable hybrid can vary depending on whether the sequences shared between two molecules are interspersed throughout the nucleic acid molecules or are clustered (i.e., localized) in distinct regions on the nucleic acid molecules.

In accordance with the present invention, an isolated nucleic acid molecule is a nucleic acid molecule that has been removed from its natural milieu (i.e., that has been subject to human manipulation). As such, "isolated" does not reflect the extent to which the nucleic acid molecule has been purified. An isolated nucleic acid molecule can include DNA, RNA, or derivatives of either DNA or RNA. As used herein, an isolated nucleic acid molecule can include both the coding strand (i.e., the sense strand) and the complementary strand (i.e., the non-sense, or anti-sense strand) of a DNA molecule.

An isolated nucleic acid molecule of the present invention can be obtained from its natural source either as an entire (i.e., complete) gene or a portion thereof. As used herein, the phrase "at least a portion of" an entity refers to an amount of the entity that is at least sufficient to have the functional aspects of that entity. For example, at least a portion of a nucleic acid sequence, as used herein, is an amount of a nucleic acid sequence capable of forming a stable hybrid with that nucleic acid sequence under stringent hybridization conditions. Nucleic acid molecules of the present invention, therefore, can be derived from any source having a nucleic acid molecule that hybridizes under stringent hybridization conditions with nhTCP. Preferred sources include animals, with mammals, birds, amphibians, insects and fish being more preferred, and with humans, other primates, cats, dogs, cattle, horses, swine, sheep and rodents as well as other pets and livestock being even more preferred. An isolated nucleic acid molecule of the present invention can also be produced using recombinant DNA technology (e.g., polymerase chain reaction (PCR) amplification, cloning) or chemical synthesis.

Isolated nucleic acid molecules include natural nucleic acid molecules and homologues thereof, including, but not limited to, natural allelic variants, nucleic acid molecules that are the result of alternative splicing mechanisms, and modified nucleic acid molecules in which nucleotides have been inserted, deleted, substituted, and/or inverted in such a manner that such modifications do not substantially interfere with the nucleic acid molecule's ability to encode a protein of the present invention and/or to form stable hybrids under stringent conditions with natural isolates. Included in the present invention are nucleic acid molecules that encode hTCP proteins similar to rat and mouse soluble PC6A and/or membrane bound PC6B proteins. These isoforms of hTCP proteins of the present invention are referred to herein as hTCPA and hTCPB, respectively.

A nucleic acid molecule of the present invention can include any natural gene or a homologue thereof capable of hybridizing to nhTCP. It is to be noted that, as used herein, homologues of a nucleic acid molecule include portions of that nucleic acid molecule. A nucleic acid molecule of the present invention can include one or more regulatory regions, full-length or partial coding regions, or combinations thereof. According to the present invention, a regulatory region includes any regulatory sequences that control the expression of nucleic acid molecules, including promoters, enhancers, transcription termination sequences, sequences that regulate translation, origins of replication. For example, a regulatory region of an RNA molecule of the present invention encoding hTCP is the untranslated region (UTR). The minimal size of a nucleic acid molecule of the present invention is the minimal size capable of forming a stable hybrid under stringent hybridization conditions with nhTCP.

A nucleic acid molecule homologue of the present invention can be produced using a number of methods known to those skilled in the art (see, for example, Sambrook et al., ibid.). For example, nucleic acid molecules can be modified using a variety of techniques including, but not limited to, classic mutagenesis techniques and recombinant DNA techniques, such as site-directed mutagenesis, chemical treatment of a nucleic acid molecule to induce mutations, restriction enzyme cleavage of a nucleic acid fragment, ligation of nucleic acid fragments, polymerase chain reaction (PCR) amplification and/or mutagenesis of selected regions of a nucleic acid sequence, synthesis of oligonucleotide mixtures and ligation of mixture groups to "build" a mixture of nucleic acid molecules and combinations thereof. Nucleic acid molecule homologues can be selected from a mixture of modified nucleic acids by screening for the function of the protein encoded by the nucleic acid (e.g., dibasic amino acid processing endoprotease activity, ability to induce production of a desirable antibody) and/or by hybridization with nhTCP under stringent conditions.

A nucleic acid molecule of the present invention can include a nucleic acid sequence that encodes a dibasic amino acid processing endoprotease protein, which preferably has proteolytic activity (i.e., can cleave a protein at a dibasic amino acid processing site). It is to be noted that the term "a" or "an" entity refers to one or more of that entity; as such, the terms "a" (or "an"), "one or more" and "at least one" can be used interchangeably herein. It is also to be noted that although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding a protein. Dibasic amino acid processing endoprotease proteins of the present invention include, but are not limited to, full-length proteins, proteins that are truncates thereof and fusion proteins. Examples of such proteins are disclosed below. A particularly preferred nucleic acid molecule of the present invention includes a nucleic acid sequence that encodes a human CD4+ T-lymphocyte dibasic amino acid processing endoprotease protein, which preferably has proteolytic activity.

Various embodiments of the present invention involve use of an isolated nucleic acid molecule that is capable of hybridizing, under stringent conditions, with a nucleic acid molecule comprising nhTCP$_{483}$. As used herein, a nucleic acid molecule that comprises nhTCP$_{483}$ refers to a nucleic acid molecule that includes nhTCP$_{483}$; such a nucleic acid molecule therefore can include nucleic acid sequences in addition to nhTCP$_{483}$ or can consist only of nhTCP$_{483}$. As such, nucleic acid molecules of this embodiment can include nhTCP, or any portion thereof (i.e., any region that is capable of hybridizing to a region of nhTCP). Additional nucleic acid molecules of this embodiment include nucleic acid molecules that are sufficiently similar to nhTCP, or any portion thereof, such that the nucleic acid molecules are able to form stable hybrids under stringent hybridization conditions with nhTCP.

Preferred nucleic acid molecules are able to form stable hybrids under stringent hybridization conditions with at least one of the following nucleic acid molecules: nhTCP$_{483}$ and nhTCP$_{-2400}$. The production of nhTCP$_{-2400}$ is described in the Examples as is the determination of certain nucleic acid sequences for nhTCP$_{-2400}$ which include SEQ ID NO:3, the deduced amino acid sequence of which is presented herein as SEQ ID NO:4; SEQ ID NO:12, the deduced amino acid sequence of which is presented herein as SEQ ID NO:13; and SEQ ID NO:14, the deduced amino acid sequence of which is presented herein as SEQ ID NO:15.

Particularly preferred nucleic acid molecules form stable hybrids under stringent hybridization conditions with at least one of the following nucleic acid molecules: nhTCP$_{444}$, nhTCP$_{2766}$, nhTCP$_{2745}$, nhTCP$_{2643}$, nhTCP$_{1345}$, an approximately 0.7 kb fragment of the 3' end of nhTCP$_{1345}$, and nhTCP$_{2397}$, production and characterization of which are described in the Examples. The nucleic acid sequence of nhTCP$_{444}$, a nucleic acid molecule used in the production of a full length nhTCP coding region, is represented herein as SEQ ID NO:16. Analysis of the nucleic acid sequence of nhTCP$_{2766}$, represented herein as SEQ ID NO:17, indicates that nhTCP$_{2766}$ apparently encodes a full-length hTCP, denoted herein as $hTCP_{915}$, the deduced amino acid sequence of which is represented herein as SEQ ID NO:18. The nucleic acid sequence of the complement of SEQ ID NO: 17 is represented herein as SEQ ID NO:28. The nucleic acid sequence of the open reading frame encoding that protein is represented herein as SEQ ID NO:19. The corresponding nucleic acid molecule is denoted herein as $nhTCP_{2745}$. Nucleic acid molecule $nhTCP_{2643}$, the nucleic acid sequence of which is represented herein as SEQ ID NO:20, apparently encodes a human CD4+ T-lymphocyte dibasic amino acid processing endoprotease proprotein, denoted herein as $hTCP_{881}$, the deduced amino acid sequence of which is represented herein as SEQ ID NO:21. Nucleic acid molecule $nhTCP_{2397}$, the nucleic acid sequence of which is represented herein as SEQ ID NO:22, encodes a putative (i.e., apparently) mature human CD4+ T-lymphocyte dibasic amino acid processing endoprotease protein, denoted herein as $hTCP_{799}$, the deduced amino acid sequence of which is represented herein as SEQ ID NO:23. Nucleic acid molecule $nhTCP_{1345}$, the nucleic acid sequence of which is represented herein as SEQ ID NO:26, spans nucleotides from about 924 to 2268 of SEQ ID NO:17. The nucleic acid sequence of the complementary strand of SEQ ID NO:26 is represented herein as SEQ ID NO:27. Also included in the present invention are fragments of $nhTCP_{1345}$. Such fragments can include any fragments of the complementary strand of $nhTCP_{1345}$ (SEQ ID NO:27), including, but not limited to, an approximately 0.7 kb fragment of the 3' end of $nhTCP_{1345}$. Nucleic acid molecules having a sequence comprising at least a portion of SEQ ID NO:27, or SEQ ID NO:28 are examples of nucleic acid molecules which are suitable for use in a therapeutic composition of the present invention, wherein the therapeutic composition reduces the infectivity of an infectious agent susceptible to inhibition of dibasic amino acid processing endoprotease activity. Preferred nucleic acid molecules are capable of hybridizing under stringent conditions with a nucleic acid molecule that includes the nucleic acid sequence SEQ ID NO:1, SEQ ID NO:3, SEQ ID NO:12, SEQ ID NO:14, SEQ ID NO:17, SEQ ID NO:19, SEQ ID NO:20, SEQ ID NO:22, and/or SEQ ID NO:26. More preferred nucleic acid molecules include regions that are at least about 86 percent identical, more preferably at least about 90 percent identical, even more preferably at least about 93 percent identical, and even more preferably at least about 95 percent identical with SEQ ID NO:1, SEQ ID NO:3, SEQ ID NO:12, and/or SEQ ID NO:14. Also more preferred are nucleic acid molecules that include regions that are at least about 91 percent identical, even more preferably at least about 93 percent identical and even more preferably at least about 95 percent identical with SEQ ID NO:19. Even more preferred are nucleic acid molecules that include the nucleic acid sequence presented in SEQ ID NO:1, SEQ ID NO:3, SEQ ID NO:12, SEQ ID NO:14, SEQ ID NO:17, SEQ ID NO:19, SEQ ID NO:20, SEQ ID NO:22, and/or SEQ ID NO:26.

A particularly preferred nucleic acid molecule of the present invention includes at least a portion of nhTCP that is capable of hybridizing under stringent conditions with nhTCP. Examples of such nucleic acid molecules include, but are not limited to, $nhTCP_{483}$, $nhTCP_{\sim 2400}$, $nhTCP_{444}$, $nhTCP_{2766}$, $nhTCP_{2745}$, $nhTCP_{2643}$, $nhTCP_{2397}$, $nhTCP_{1345}$, an approximately 0.7 kb fragment of the 3' end of $nhTCP_{1345}$, nhTCP, and fragments thereof.

All of the foregoing nucleic acid molecules can have the characteristic of being a nucleic acid molecule capable of hybridizing to a nucleic acid molecule that encodes a protein that includes the amino acid sequence presented in SEQ ID NO:2, SEQ ID NO:4, SEQ ID NO:13, SEQ ID NO:15, SEQ ID NO:18, SEQ ID NO:21 and/or SEQ ID NO:23. Certain preferred nucleic acid molecules include a nucleic acid molecule that encodes a protein that includes a region that shares at least about 96 percent amino acid sequence identity with SEQ ID NO:2, a nucleic acid molecule that encodes a protein that includes a region that shares at least about 89 percent amino acid sequence identity with SEQ ID NO:15, or a nucleic acid molecule that encodes a protein that includes a region that shares at least about 97 percent amino acid sequence identity with SEQ ID NO:18, SEQ ID NO:21 and/or SEQ ID NO:23. More preferred nucleic acid molecules encode at least a portion of a protein having the amino acid sequence of SEQ ID NO:2, SEQ ID NO:4, SEQ ID NO:13, SEQ ID NO:15, SEQ ID NO:18, SEQ ID NO:21 and/or SEQ ID NO:23. Particularly preferred nucleic acid molecules are capable of encoding a protein having dibasic amino acid processing endoprotease activity.

The present invention also includes use of nucleic acid molecules that are oligonucleotides capable of hybridizing, under stringent conditions, with complementary regions of other, preferably longer, nucleic acid molecules of the present invention, such as to complementary regions of CD4+ T-lymphocyte protease genes of the present invention, such as nhTCP, and to RNA molecules, including regulatory regions, that encode CD4+ T lymphocyte proteases of the present invention. Such oligonucleotides can hybridize under stringent conditions with complementary regions of $nhTCP_{483}$, $nhTCP\text{-}_{\sim 2400}$, $nhTCP_{444}$, $nhTCP_{2766}$, $nhTCP_{2745}$, nhTCP $_{\sim 2643}$, nhTCP 1345, an approximately 0.7 kb fragment of the 3' end of $nhTCP_{1345}$ and/or $nhTCP_{2397}$; complementary regions of nucleic acid molecules that include at least a portion of $nhTCP_{483}$, $nhTCP\text{-}_{\sim 2400}$, $nhTCP_{444}$, $nhTCP_{2766}$, $nhTCP_{2745}$, $nhTCP_{2643}$ , $nhTCP_{,1345}$, an approximately 0.7 kb fragment of the 3' end of $nhTCP_{1345}$ and/or $nhTCP_{2397}$; and complementary regions of nucleic acid molecules that hybridize under stringent conditions with $nhTCP_{483}$, $nhTCP_{\sim 2400}$, $nhTCP_{444}$, $nhTCP_{2766}$, $nhTCP_{2745}$, $nhTCP_{2643}$, $nhTCP_{1345}$, an approximately 0.7 kb fragment of the 3' end of $nhTCP_{1345}$ and/or $nhTCP_{2397}$. Such oligonucleotides can be RNA, DNA, or derivatives of either. The minimal size of such oligonucleotides is the size required to form a stable hybrid between a given oligonucleotide and the complementary sequence on another nucleic acid molecule of the present invention. As such, the size is dependent on nucleic acid composition and percent identity between the oligonucleotide and complementary sequence as well as upon hybridization conditions per se (e.g., temperature, salt concentration). The size of the oligonucleotide must also be sufficient for the use of the oligonucleotide in accordance with the present invention. Oligonucleotides of the present invention can be used in a variety of applications including, but not limited to, as probes to identify additional nucleic acid molecules, as primers to amplify or extend nucleic acid molecules or in therapeutic applications to inhibit dibasic amino acid processing endoprotease activity, which be discussed in more detail below.

Knowing the nucleic acid sequence of certain nucleic acid molecules of the present invention allows one skilled in the art to make copies of those nucleic acid molecules as well as to obtain nucleic acid molecules including at least a portion of such nucleic acid molecules and other nucleic acid molecule homologues. Such nucleic acid molecules can be obtained in a variety of ways including screening appropriate expression libraries with antibodies of the present invention; traditional cloning techniques using oligonucleotide probes of the present invention to screen appropriate libraries or DNA; and PCR amplification of appropriate libraries or DNA using oligonucleotide primers of the present invention. Such libraries, or DNA samples, can include genomic or cDNA, the latter of which can be produced from RNA of any cell type that expresses nhTCP or a homologue thereof. Techniques to clone and amplify genes are disclosed, for example, in Sambrook et al., ibid.

One embodiment of the present invention is an isolated protein encoded by a nucleic acid molecule of the present invention. The present invention also includes use of proteins encoded by nucleic acid molecules that can be used in accordance with the present invention as disclosed herein. According to the present invention, an isolated, or biologically pure, protein, is a protein that has been removed from its natural milieu. As such, "isolated" and "biologically pure" do not necessarily reflect the extent to which the protein has been purified. An isolated protein of the present invention can be obtained from its natural source. Examples of such sources are disclosed herein. An isolated protein of the present invention can also be produced using recombinant DNA technology or chemical synthesis.

As used herein, an isolated protein of the present invention can be a full-length dibasic amino acid processing endoprotease encoded by a nucleic acid molecule that forms a hybrid with nhTCP under stringent hybridization conditions. Such a full-length protein is also referred to herein as TCP, or CD4+ T-lymphocyte dibasic amino acid processing endoprotease, an example of which includes hTCP, for human CD4+ T-lymphocyte dibasic amino acid processing endoprotease (although it is to be appreciated that such proteins can also be expressed in other cell types). Additional proteins of the present invention include homologues of TCP, such as a TCP in which amino acids have been deleted (e.g., a truncated version of the protein, such as a peptide), inserted, inverted, substituted and/or derivatized (e.g., by glycosylation, phosphorylation, acetylation, myristylation, prenylation, palmitoylation, amidation and/or addition of glycerophosphatidyl inositol) such that the homologue has dibasic amino acid processing endoprotease activity and/or is encoded by a nucleic acid molecule that is capable of hybridizing under stringent conditions with nhTCP. In one embodiment, a homologue also includes at least one epitope capable of eliciting an immune response against a TCP (i.e., when a TCP homologue is administered to an animal as an immunogen, using techniques known to those skilled in the art, the animal will produce a humoral and/or cellular immune response against at least one epitope of the TCP). Dibasic amino acid processing endoprotease activity as well as the ability of a protein to effect an immune response, can be measured using techniques known to those skilled in the art.

TCP homologues of the present invention can be the result of natural allelic variation or natural mutation. TCP homologues can also be produced using techniques known in the art including, but not limited to, direct modifications to the protein or modifications to the gene encoding the protein using, for example, classic or recombinant DNA techniques to effect random or targeted mutagenesis. Isolated proteins of the present invention, including homologues, can be identified in a straight-forward manner by the proteins' ability to cleave dibasic amino acid processing sites and/or to be encoded by a nucleic acid molecule that hybridizes under stringent conditions with nhTCP. Such techniques are known to those skilled in the art.

The minimum size of a protein of the present invention is a size that is sufficient to have been encoded by a nucleic acid molecule capable of hybridizing under stringent conditions with nhTCP. The minimum size of such a protein is from about 4 to about 6 amino acids.

Proteins of the present invention preferably have dibasic amino acid processing endoprotease activity (also referred to herein as dibasic amino acid processing endoproteases) and are able to cleave (i.e., effect cleavage of) a precursor protein having a dibasic amino acid processing site. Sources of such precursor proteins include viruses, bacteria, fungi, animals and plants. A number of such precursor proteins are known to those skilled in the art, including, but not limited to, those disclosed in Barr, ibid. The present invention also includes the ability to identify other precursor proteins that have dibasic amino acid processing sites using techniques known to those skilled in the art, such as cleavage assays and/or amino acid sequence analysis.

Preferred dibasic amino acid processing endoproteases of the present invention are capable of effecting cleavage of precursor proteins of infectious agents that require cleavage of certain precursor proteins in order to be infective. Such infectious agents, therefore, are susceptible to inhibition of dibasic amino acid processing endoprotease activity and can include viruses, bacteria and parasites, with enveloped viruses being preferred. Examples of such viruses include, but are not limited to, retroviruses, herpes viruses, hepadnaviruses, pox viruses, orthomyxoviruses, paramyxoviruses, rhabdoviruses, togaviruses, arena viruses, bunyaviruses and coronaviruses. Preferred dibasic amino acid processing endoproteases of the present invention can effect cleavage of one or more retroviral, herpes viral, and/or hepatitis viral precursor envelope proteins.

Particularly preferred proteins of the present invention are capable of effecting cleavage of a precursor envelope protein of a virus that can infect cells displaying CD4+ markers on their cell surfaces, such as CD4+ T-lymphocytes, macrophages, dendritic cells, reticular cells of the lymph nodes, spleen and thymus, and lymphoid tissue, including Peyer's patches. Preferred viruses to target include lentiviruses and lymphotropic virus that can infect a variety of animals, including, but not limited to, humans, apes, cats, dogs, cattle and other mammals. Examples of such viruses include, but are not limited to, human (HIV), simian (SIV), feline (FIV) and canine (CIV) immunodeficiency viruses, as well as human T-cell lymphotropic virus (HTLV), bovine leukemia virus (BLV) and feline leukemia virus (FLV).

One embodiment of the present invention is a dibasic amino acid processing endoprotease that is able to effect cleavage of a precursor cellular protein that has a dibasic amino acid processing site. As used herein, a cellular protein is a protein that is produced endogenously (i.e., naturally) by a cell. Examples of such precursor cellular proteins include, but are not limited to, precursors of cytokines, hormones, other growth factors, and other factors that regulate the behavior of a cell, such precursors requiring cleavage by a dibasic amino acid processing endoprotease as part of their maturation process.

As discussed above, the extent of cleavage that a particular dibasic amino acid processing endoprotease can effect is a function of the amino acid sequence of the dibasic amino acid processing site and of the dibasic amino acid processing endoprotease. In a preferred embodiment, a dibasic amino acid processing endoprotease of the present invention is selected that can cleave a certain precursor protein with acceptable efficiency, such as selecting hTCP to cleave a HIV precursor envelope gp160 protein.

Proteins of the present invention include proteins encoded by nucleic acid molecules of the present invention as disclosed herein. Preferred proteins include proteins encoded by preferred nucleic acid molecules as disclosed herein. In one embodiment, a preferred protein of the present invention includes an amino acid sequence having at least about 96 percent identity with the amino acid sequence of SEQ ID NO:2, at least about 89 percent amino acid sequence identity with SEQ ID NO:15, and/or at least about 97 percent amino acid sequence identity with SEQ ID NO:18, SEQ ID NO:21 and/or SEQ ID NO:23.

Particularly preferred is a protein that includes an amino acid sequence comprising at least a portion of SEQ ID NO:2, of SEQ ID NO:4 of SEQ ID NO:13, of SEQ ID NO:15, of SEQ ID NO:18, of SEQ ID NO:21, and/or of SEQ ID NO:23, wherein the minimum length of the portion is sufficiently long such that it is encoded by a nucleic acid molecule capable of hybridizing under stringent conditions with nhTCP. Examples of such proteins include, but are not limited to hTCP (encoded by nhTCP), $hTCP_{161}$, (encoded by $nhTCP_{483}$), $nhTCP_{-800}$ (encoded by $nhTCP_{-2400}$), $hTCP_{915}$ (encoded by $nhTCP_{2745}$), $hTCP_{881}$ (encoded by $nhTCP_{2643}$), and $hTCP_{799}$ (encoded by $nhTCP_{2397}$)

The present invention includes fusion proteins comprising a protease protein domain (e.g., TCP or a homologue thereof) attached to a heterologous fusion segment, which preferably comprises one or more amino acids. Inclusion of a fusion segment as part of a protein of the present invention can enhance the protein's stability during production, storage and/or use. Furthermore, a fusion segment can function as a tool to simplify purification of a protein of the present invention, such as to enable purification of the resultant fusion protein using affinity chromatography. In one embodiment, a fusion protein of the present invention can be a multivalent, or multifunctional, protein that includes a proteolytic domain fused to another functional domain. Examples of such multifunctional proteins include, but are not limited to, proteins having more than one enzymatic activity and proteins that include a protease domain and a targeting domain that can target the protease to a desired cell type or to a particular compartment within a cell. The present invention also includes fusion proteins comprising inhibitors of proteases of the present invention joined to targeting domains.

A suitable fusion segment can be a domain of any size that has the desired function. It is within the scope of the present invention to use one or more fusion segments. Fusion segments can be joined to amino and/or carboxyl termini of the protease protein-containing domain of the protein. Linkages between fusion segments and protease protein domains of fusion proteins can be susceptible to cleavage in order to enable straight-forward recovery of the protease protein domains of such proteins. Fusion proteins are preferably produced by culturing a recombinant cell transformed with a fusion nucleic acid molecule that encodes a protein including the fusion segment attached to either the carboxyl and/or amino terminal end of a protease protein-containing domain.

Additional fusion proteins of the present invention include decoy targets that comprise a dibasic amino acid processing site. Exposure of a dibasic amino acid processing endoprotease to such targets reduces the ability of the protease to cleave other proteins. Also included in the present invention are fusion proteins that comprise a marker protein joined to another compound by a dibasic amino acid processing site. Such fusion proteins can be used to assay protease activity if the marker protein is "activated" upon cleavage of the processing site. An example of such a fusion protein is a mature α-factor mating pheromone joined by a dibasic amino acid processing site to another compound such that the α-factor is only active when cleaved from the other compound.

The present invention also includes mimetopes of proteins of the present invention. In accordance with the present invention, a mimetope of a protein refers to any compound that is able to mimic the activity of that protein, often because the mimetope has a structure that mimics the protein. For example, a mimetope of a dibasic amino acid processing endoprotease of the present invention is a compound that has an activity similar to that of an isolated dibasic amino acid processing endoprotease of the present invention. As such, mimetopes of the present invention can be used in a number of applications disclosed herein for proteins of the present invention.

A mimetope can be a peptide that has been modified to decrease its susceptibility to degradation but that still retains the desired activity. Other examples of mimetopes include, but are not limited to, carbohydrate-based compounds, lipid-based compounds, nucleic acid-based compounds, natural organic compounds, synthetically derived organic compounds, anti-idiotypic antibodies and/or catalytic antibodies, or fragments thereof. Such mimetopes can be designed using computer-generated structures of proteins of the present invention. Mimetopes can also be obtained by generating random samples of molecules, such as oligonucleotides, peptides or other organic molecules, and screening such samples by affinity chromatography techniques using, for example, antibodies raised against a protein of the present invention.

The present invention also includes isolated antibodies capable of selectively binding to a protein of the present invention or to a mimetope thereof. Antibodies capable of selectively binding to a TCP, or homologue thereof, of the present invention are referred to as anti-TCP antibodies. A particularly preferred antibody of this embodiment is an anti-hTCP antibody. Isolated antibodies are antibodies that have been removed from their natural milieu. The term "isolated" does not refer to the state of purity of such antibodies. As such, isolated antibodies can include anti-sera containing such antibodies, or antibodies that have been purified to varying degrees. As used herein, the term "selectively binds to" refers to the ability of such antibodies to preferentially bind to specified proteins and mimetopes thereof of the present invention. Binding can be measured using a variety of methods known to those skilled in the art, including immunoblot assays, immunoprecipitation assays, radioimmunoassays, enzyme immunoassays (e.g., ELISA), immunofluorescent antibody assays and immunoelectron microscopy; see, for example, Sambrook et al., ibid.

Antibodies of the present invention can be either polyclonal or monoclonal antibodies. Antibodies of the present invention include functional equivalents such as antibody fragments and genetically-engineered antibodies, including single chain antibodies, that are capable of selectively binding to at least one of the epitopes of the protein or mimetope used to obtain the antibodies. Preferred antibodies are raised in response to proteins, or mimetopes thereof, that are encoded, at least in part, by a nucleic acid molecule of the present invention.

A preferred method to produce antibodies of the present invention includes (a) administering to an animal an effective amount of a protein or mimetope thereof of the present invention to produce the antibodies and (b) recovering the antibodies. Antibodies raised against defined proteins or mimetopes can be advantageous because such antibodies are not substantially contaminated with antibodies against other substances that might otherwise cause interference in a diagnostic assay or side effects if used in a therapeutic composition.

Antibodies of the present invention have a variety of potential uses that are within the scope of the present invention. For example, such antibodies can be used (a) as reagents in assays to detect and selectively bind to proteins of the present invention; (b) as tools to recover desired proteins of the present invention from a mixture of proteins and other contaminants; (c) as protease inhibitors; and/or (d) as delivery vehicles into a cell. For example, antibodies of the present invention can be produced that selectively bind to and thereby inactivate proteases of the present invention by, for example, direct interaction with the active site of the protease and/or by allosteric interaction with the protease. Antibodies can also deliver inhibitory compounds to a targeted protease. Antibodies of the present invention that are used therapeutically can enter a desired cell type by endocytosis and thereby interact with the catalytic and/or luminal domains of the targeted protease.

The present invention also includes a recombinant vector, which includes a nucleic acid molecule of the present invention inserted into any vector capable of delivering the nucleic acid molecule into a host cell or virus. Such a vector contains heterologous nucleic acid sequences, that is nucleic acid sequences that are not naturally found adjacent to nucleic acid molecules of the present invention. The vector can be either RNA or DNA, either prokaryotic or eukaryotic, and typically is a virus or a plasmid. Recombinant vectors can be used in the cloning, sequencing, and/or otherwise manipulating of nucleic acid molecules of the present invention. One type of recombinant vector, herein referred to as a recombinant molecule and described in more detail below, can be used in the expression of nucleic acid molecules of the present invention. Preferred recombinant vectors are capable of replicating in the transformed cell.

Any nucleic acid molecule disclosed herein can be included in a recombinant vector of the present invention. Preferred nucleic acid molecules to include are preferred nucleic acid molecules of the present invention.

In one embodiment, an isolated protein of the present invention is produced by culturing a cell capable of expressing the protein under conditions effective to produce the protein, and recovering the protein. A preferred cell to culture is a recombinant cell that is capable of expressing the protein, the recombinant cell being produced by transforming a host cell with one or more nucleic acid molecules of the present invention. Transformation of a nucleic acid molecule into a cell can be accomplished by any method by which a nucleic acid molecule can be inserted into the cell. Transformation techniques include, but are not limited to, transfection, electroporation, microinjection, lipofection, adsorption, and protoplast fusion. A recombinant cell may remain unicellular or may grow into a tissue, organ or a multicellular organism. Transformed nucleic acid molecules of the present invention can remain extrachromosomal or can integrate into one or more sites within a chromosome of the transformed (i.e., recombinant) cell in such a manner that their ability to be expressed is retained. Suitable, as well as preferred, nucleic acid molecules with which to transform a host cell are provided herein.

Suitable host cells to transform include any cell that can be transformed and that can express the introduced nucleic acid molecule(s). Such cells are, therefore, capable of producing proteins of the present invention after being transformed with at least one nucleic acid molecule of the present invention. Host cells can be either untransformed cells or cells that are already transformed with at least one nucleic acid molecule. Suitable host cells of the present invention can include bacterial, fungal (including yeast), insect, animal and plant cells. Preferred host cells include bacterial, yeast, insect, mammalian and amphibian (e.g., Xenopus) cells.

A recombinant cell is preferably produced by transforming a host cell with one or more recombinant molecules, each comprising one or more nucleic acid molecules of the present invention operatively linked to one or more transcription control sequences, preferably included within an expression vector. The phrase operatively linked refers to insertion of a nucleic acid molecule into an expression vector in a manner such that the molecule is able to be expressed when transformed into a host cell. As used herein, an expression vector is a DNA or RNA vector that is capable of transforming a host cell and of effecting expression of a specified nucleic acid molecule. Preferably, the expression vector is also capable of replicating within the host cell. Also preferred are expression vectors that can integrate into the host genome.

Expression vectors can be either prokaryotic or eukaryotic, and are typically viruses or plasmids. Expression vectors of the present invention include any vectors that function (i.e., direct gene expression) in recombinant cells of the present invention, including in bacterial, fungal (including yeast), insect, animal, and/or plant cells. As such, nucleic acid molecules of the present invention can be operatively linked to expression vectors containing regulatory sequences such as promoters, operators, repressors, enhancers, transcription termination sequences, sequences that regulate translation, origins of replication, and other regulatory sequences that are compatible with the recombinant cell and that control the expression of nucleic acid molecules of the present invention. As used herein, a transcription control sequence includes a sequence which is capable of controlling the initiation, elongation, and termination of transcription. Particularly important transcription control sequences are those which control transcription initiation, such as promoter, enhancer, operator and/or repressor sequences. Suitable transcription control sequences include any transcription control sequence that can function in at least one of the recombinant cells of the present invention. A variety of such transcription control sequences are known to those skilled in the art. Preferred transcription control sequences include those which function in bacterial, yeast, insect, mammalian, and/or amphibian cells, such as, but not limited to, tac, lac, trp, trc, oxy-pro, omp/lpp, rrnB, bacteriophage lambda ($\lambda$) (such as $\lambda.p_L$ and $\lambda.p_R$ and fusions that include such promoters), bacteriophage T7, T7lac, bacteriophage T3, bacteriophage SP6, bacteriophage SP01, metallothionein, yeast $\alpha$-factor mating pheromone, yeast formate dehydrogenase, Pichia alcohol oxidase, viral long terminal repeat, other mammalian viral, insect viral, or subtilisin-like protein convertase transcription control sequences as well as other sequences capable of controlling gene expression in prokaryotic or eukaryotic cells. Additional yeast promoters include, but are not limited to promoters of genes encoding the following yeast proteins: Kex2, alcohol dehydrogenase I (ADH1) or II (ADH2), phosphoglycerate kinase (PGK), triose phosphate isomerase (TPI), glyceraldehyde-3-phosphate dehydrogenase (GAPDH; also referred to as TDH3, for triose phosphate dehydrogenase), galactokinase (GAL1), galactose-1-phosphate uridyl-transferase (GAL7), UDP-galactose epimerase (GAL10), cytochrome $c_1$ (CYC1) and acid phosphatase (PHOS), with hybrid promoters such as ADH2/ GAPDH and CYC1/GAL10 promoters being more preferred, and the ADH2/GAPDH promoter, which is induced when glucose concentrations in the cell are low (e.g., about 0.1 to about 0.2 percent), being even more preferred. Likewise, a number of upstream activation sequences (UASs), also referred to as enhancers, are known. Preferred upstream activation sequences for expression in yeast include, but are not limited to, the UASs of genes encoding the following proteins: CYC1, ADH2, GAL1, GAL7 and GAL10, as well as other UASs activated by the GAL4 gene product, with the ADH2 UAS being particularly preferred. Since the ADH2 UAS is activated by the ADR1 gene product, it is preferable to overexpress the ADR1 gene when a heterologous gene is operatively linked to the ADH2 UAS. Preferred transcription termination sequences for expression in yeast include the termination sequences of the α-factor mating pheromone, GAPDH, and CYC1 genes. Transcription control sequences of the present invention can also include naturally occurring transcription control sequences naturally associated with a DNA sequence encoding a dibasic amino acid processing endoprotease protein of the present invention.

Recombinant molecules of the present invention may also contain secretory signals (i.e., signal segment nucleic acid sequences) to enable an expressed protein to enter into the secretory pathway in the cell that produces the protein. Suitable signal segments can be determined by those skilled in the art.

Recombinant molecules of the present invention may also contain fusion sequences which lead to the expression of inserted nucleic acid molecules of the present invention as fusion proteins, examples of which are disclosed herein.

A recombinant molecule of the present invention includes at least one of any nucleic acid molecule heretofore described operatively linked to at least one of any transcription control sequence capable of effectively regulating expression of the nucleic acid molecule(s) in the cell to be transformed. Suitable and preferred nucleic acid molecules to include in recombinant molecules of the present invention are disclosed herein. Particularly preferred recombinant molecules include the following regulatory sequences: TDH3 or ADH2/GAPDH promoter sequences, Kex2 or α-factor mating pheromone signal and leader sequences, a translation stop sequence, and CYC1 or α-factor mating pheromone transcription terminator sequences. Even more preferred recombinant molecules include pα/nhTCP-$_{\sim 2400}$ and pα/nhTCP, the production of at least some of which is described in the Examples section. Additional preferred recombinant molecules include pα/nhTCP$_{2766}$, pα/nhTCP$_{2745}$, pα/nhTCP$_{2643}$, and pα/nhTCP$_{2397}$.

A recombinant cell of the present invention includes any cell that is transformed with at least one of any nucleic acid molecule of the present invention. Suitable and preferred nucleic acid molecules and recombinant molecules with which to transform cells are disclosed herein. Particularly preferred recombinant cells include S. cerevisiae CB023:pα/nhTCP$_{\sim 2400}$, S. cerevisiae CB023:pα/nhTCP and S. cerevisiae kex2Δ:pα/env,pα/nhTCP, the production of which is described in the Examples section. Additional preferred recombinant molecules include S. cerevisiae CB023:pα/nhTCP$_{2766}$, S. cerevisiae CB023:pα/nhTCP$_{2745}$, S. cerevisiae CB023:pα/nhTCP$_{2643}$, and S. cerevisiae CB023:pα/nhTCP$_{2397}$.

A recombinant virus of the present invention can include a viral genome in which nucleotides have been deleted, inserted, substituted or inverted using recombinant techniques known to those skilled in the art such that the recombinant viral genome is no longer the same as a natural viral genome. A recombinant viral genome of the present invention is capable of effecting expression (e.g., transcription, translation) of coding regions of an hTCP nucleic acid molecule of the present invention that are operatively linked to regulatory sequences within the genome. As used herein, a coding region is a stretch of nucleotides that encodes an RNA molecule and/or a protein. The phrase operatively linked refers to the positioning of a coding region in the viral genome such that the coding region is able to be expressed when the genome is inside a cell. Regulatory sequences include transcription control sequences, translation control sequences, and other regulatory sequences that control the expression of coding regions. Transcription control sequences are sequences which control the initiation, elongation, and termination of transcription. Particularly important transcription control sequences are those which control transcription initiation, such as promoter, enhancer, operator and repressor sequences. Suitable regulatory sequences include any regulatory sequence that can function in the present invention. Preferred regulatory sequences are disclosed herein.

It may be appreciated by one skilled in the art that use of recombinant DNA technologies can improve expression of transformed nucleic acid molecules by manipulating, for example, the number of copies of the nucleic acid molecules within a host cell (e.g., by using cir° strains), the efficiency with which those nucleic acid molecules are transcribed, the efficiency with which the resultant transcripts are translated, the efficiency of post-translational modifications, and the ability to maintain plasmids within a cell (e.g., by incorporating a selectable marker, such as an antibiotic resistance or prototrophic gene, on the plasmid). Recombinant techniques useful for increasing the expression of nucleic acid molecules of the present invention include, but are not limited to, operatively linking nucleic acid molecules to high-copy number plasmids, integration of the nucleic acid molecules into one or more host cell chromosomes, addition of vector stability sequences to plasmids, substitutions or modifications of transcription control signals (e.g., promoters, operators, enhancers), substitutions or modifications of translational control signals (e.g., ribosome binding sites, Shine-Dalgarno sequences), modification of nucleic acid molecules of the present invention to correspond to the codon usage of the host cell, deletion of sequences that destabilize transcripts, and use of control signals that temporally separate recombinant cell growth from recombinant protein production during fermentation. The activity of an expressed recombinant protein of the present invention may be improved by fragmenting, modifying, or derivatizing the resultant protein.

In accordance with the present invention, recombinant cells can be used to produce a protein of the present invention by culturing such cells under conditions effective to produce such a protein, and recovering the protein. Effective conditions to produce a protein include, but are not limited to, appropriate media, bioreactor, temperature, pH and oxygen conditions that permit protein production. An appropriate, or effective, medium refers to any medium in which a cell of the present invention, when cultured, is capable of producing a protein of the present invention. Such a medium is typically an aqueous medium comprising assimilable carbohydrate, nitrogen and phosphate sources, as well as appropriate salts, minerals, metals and other nutrients, such as vitamins. The medium may comprise complex nutrients or may be a defined minimal medium.

Cells of the present invention can be cultured in conventional fermentation bioreactors, which include, but are not limited to, batch, fed-batch, cell recycle, and continuous fermentors. Culturing can also be conducted in shake flasks, test tubes, microtiter dishes, and petri plates. Culturing is carried out at a temperature, pH and oxygen content appropriate for the recombinant cell. Such culturing conditions are well within the expertise of one of ordinary skill in the art.

Depending on the vector and host system used for production, resultant proteins may either remain within the recombinant cell; be secreted into the fermentation medium; be secreted into a space between two cellular barriers (e.g., cell membranes and/or cell walls), such as the periplasmic spaces of E. coli and yeast; or be retained on the outer surface of a cell or viral (including bacteriophage) membrane. The phrase "recovering the protein" refers simply to collecting the whole fermentation medium containing the protein and need not imply additional steps of separation or purification. Proteins of the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, chromatofocusing and differential solubilization.

In one embodiment, dibasic amino acid processing endoprotease proteins of the present invention are retrieved in "substantially pure" form. As used herein, "substantially pure" refers to a purity that allows for the effective use of the protein, for example, to identify an inhibitor thereof, as disclosed in more detail herein.

In another embodiment, dibasic amino acid processing endoprotease proteins of the present invention are retained within the recombinant cells that produced them. Such recombinant cells can have a variety of uses including in delivery and assay systems.

One embodiment of the present invention is a recombinant cell comprising a cell transformed with, and capable of expressing, a first nucleic acid molecule that is capable of hybridizing, under stringent conditions, with a dibasic amino acid processing endoprotease gene comprising nhTCP. Another embodiment of the present invention is a recombinant cell comprising a cell transformed with, and capable of expressing, a first nucleic acid molecule that reduces the expression of a dibasic amino acid processing endoprotease hTCP gene by hybridizing with a dibasic amino acid processing endoprotease hTCP gene, and transcription products thereof. Such a recombinant cell can be used in the production of proteins of the present invention and in a variety of other applications disclosed herein, including, but not limited to, the identification of compounds that inhibit dibasic amino acid processing endoproteases of the present invention and the production of surrogate cells that produce desired proteins. Preferred proteins have dibasic amino acid processing endoprotease activity. In one embodiment, such a recombinant cell can be a cell transformed in vivo, ex vivo or in vitro with a nucleic acid molecule that reduces dibasic amino acid processing endoprotease activity in the transformed cell compared to in an untransformed cell, as a result of, for example, antisense, triplex-helix formation, gene knockout, and/or RNA drug based technologies.

In one embodiment, a recombinant cell capable of expressing a dibasic amino acid processing endoprotease protein of the present invention also produces a precursor protein having a dibasic amino acid processing site. The precursor protein can be either an endogenous or heterologous precursor protein. An endogenous protein is naturally produced by the cell, whereas a heterologous precursor protein is encoded by a second nucleic acid molecule that has been introduced into the recombinant cell. Such recombinant cells can be used in a variety of applications including, but not limited to, identification of compounds that inhibit dibasic amino acid processing endoproteases of the present invention and surrogate producers of desired proteins.

Recombinant cells of the present invention can be produced in vitro or in vivo. That is, nucleic acid molecules can be introduced into cells (i.e., transformation can occur) either in vitro or in vivo.

The present invention includes therapeutic compositions that are capable of reducing the infectivity of an infectious agent that has a dibasic amino acid processing site. Such compositions are based on the discovery of the human T cell protease gene and, as such, can be targeted to TCPs and homologues thereof. Such compositions include, but are not limited to, nucleic acid molecules that reduce the expression of a dibasic amino acid processing endoprotease hTCP gene by hybridizing with a dibasic amino acid processing endoprotease hTCP gene, and transcription products thereof as well as compounds that inhibit dibasic amino acid processing endoprotease activity; such inhibitory compounds can be identified by their ability to inhibit the activity of hTCP. Therapeutic compositions of the present invention can also include other components, such as excipients. Suitable excipients include any component in which nucleic acid molecules, proteins, or inhibitory compounds of the present invention can be formulated that the animal to be treated can tolerate. The use of excipients is well known to those skilled in the art as are suitable excipients themselves.

Therapeutic compositions of the present invention are able to reduce the infectivity of an infectious agent by interfering with the production of one or more cleavage proteins required in the production of an infectious agent. For example, many if not all envelope (or enveloped) viruses produce precursor envelope proteins that require cleavage by dibasic amino acid processing endoproteases in order to propagate infectious virus. One such precursor envelope protein is the HIV gp160. The present invention includes compositions that are capable of reducing the spread of HIV and, thus to retard or reverse the onset of AIDS, because the compositions are capable of blocking the cleavage of gp160 into gp120 and gp41 in T lymphocytes.

Therapeutic compositions of the present invention are capable of reducing, or inhibiting, the propagation or spread of an infectious agent through a host, thereby decreasing or preventing further infection and/or disease otherwise caused by the infectious agent. Infectious agents are capable of spreading through host organisms by infecting cells, replicating and infecting additional cells, often causing disease. Infectious agents include viruses, bacteria, fungi, other parasites, and any other agents that effect infection and disease, particularly in animals and plants, and more particularly in animals. As used herein, susceptible infectious agents are infectious agents that have reduced infectivity when dibasic amino acid processing endoprotease activity is reduced. Examples of susceptible infectious agents are disclosed herein. Preferred infectious agents to target with therapeutic compositions of the present invention are enveloped viruses, such as retroviruses (e.g., lentiviruses, such as immunodeficiency viruses; type A cisternaviruses; type B oncoviruses, such as mammary tumor viruses; type C oncoviruses, such as human lymphotropic viruses, leukemia viruses, sarcoma viruses, leukosis viruses; type D oncoviruses; and type F spumaviruses), herpes viruses (e.g., cytomegaloviruses, herpes simplex, varicella-herpes zoster, and Epstein-Barr viruses), hepadnaviruses (e.g., hepatitis A, B, C, D, E, and other non-A, non-B hepatitis viruses), poxviruses (e.g., variola and vaccinia viruses), orthomyxoviruses (e.g., influenza viruses), paramyxoviruses (e.g., measles, mumps, para influenza, Sendai and Newcastle disease viruses), rhabdoviruses (e.g., filoviridae, rabies and vesicular stomatitis virus), togaviruses (e.g. flaviviruses and alphaviruses), arena viruses, bunyaviruses and coronaviruses. Retroviruses, herpes viruses, and hepatitis viruses are more preferred infectious agents to target, with leukemia, lymphotropic, sarcoma and lentiviruses being even more preferred, and with viruses capable of infecting a cell type expressing CD4+ markers being especially preferred. Particularly preferred lymphotropic viruses include HTLVs, such as HTLV-I and HTLV-II; BLVs; and FLVs. Particularly preferred lentiviruses include HIV, SIV, FIV, and CIV, with HIV-1 and HIV-2 being even more preferred.

One embodiment of the present invention is a therapeutic composition that includes a nucleic acid molecule that reduces the expression of a dibasic amino acid processing endoprotease hTCP gene by hybridizing with a dibasic amino acid processing endoprotease hTCP gene, and transcription products thereof. The size of such a nucleic acid molecule is restricted only in that the molecule must be capable of forming a hybrid as stated. As such, nucleic acid molecules included in therapeutic compositions can be oligonucleotides, full-length genes, or partial genes and can correspond to regulatory and/or coding regions of protease genes. An example of a such a nucleic acid molecule is nhTCP$_{1345}$, and any fragments of such molecule. Preferred fragments of nhTCP$_{1345}$ include any fragment of the 3' end of nhTCP$_{1345}$, including oligonucleotide fragments, and larger fragments, such as an approximately 0.7 kb fragment. Such nucleic acid molecules, examples of which are disclosed herein, can be administered in an effective manner to decrease production of dibasic amino acid processing endoproteases within cells using, for example, antisense-, triplex formation-, ribozyme-, gene knockout- and/or RNA drug-based technologies. In one embodiment, such nucleic acid molecules, and particularly, oligonucleotides, can be modified to increase the stability of the molecule in vivo in order to enable the molecule to more readily enter a target cell, be retained by the target cell, interact with the cellular target, and not interact with other macromolecules. Moreover, such nucleic acid molecules can be modified to increase the stability of the molecule by preventing degradation of the molecule by endonucleases both inside the target cell and outside the target cell. For example an oligonucleotide can be chemically modified for stability by the addition of a thiol group to the phosphate on the sugar-phosphate backbone of the oligonucleotide. Such oligonucleotides are referred to herein as ODN (oligodeoxynucleotide) PS (phosphorothioate) oligonucleotides, or PS oligonucleotides. Further strategies for using antisense-, triplex formation-, ribozyme-, gene knockout- and/or RNA drug-based technologies are described in Maulik et al., 1997, *Molecular Biotechnology: Therapeutic Applications and Strategies,* Wiley-Liss, Inc., which is incorporated herein by reference in its entirety. The present invention, therefore, includes such nucleic acid molecule-containing therapeutic compositions and methods to interfere with the production of dibasic amino acid processing endoproteases by use of one or more of such technologies. Appropriate nucleic acid molecule-containing therapeutic compositions can be administered to an animal, using techniques known to those skilled in the art, either prior to or after infection by an infectious agent in order to protect the animal from disease.

Another embodiment of the present invention is a therapeutic composition that includes an inhibitory compound that inhibits dibasic amino acid processing endoprotease activity. Such a compound can be identified by its ability to inhibit the activity of hTCP or of a homologue or mimetope thereof. Also included are methods to identify such inhibitory compounds, yeast strains that can be used to identify inhibitory compounds method and assay kits based on such methods.

The use of compounds that inhibit dibasic amino acid processing endoproteases of the present invention as therapeutic compounds have several advantages. Cellular dibasic amino acid processing endoproteases are preferred over enzyme targets inherent to the infectious agent (e.g., polymerases, regulatory factors, surface antigens, or proteases encoded by the infectious agent) because it is believed that over time, drug-resistant infectious agents are likely to develop much more rapidly than are drug-resistant cellular proteases. Cellular dibasic amino acid processing endoproteases are also attractive targets for inhibitory drug therapy because the cellular location of dibasic amino acid processing endoproteases in the secretory pathway (often in or near the Golgi apparatus) causes dibasic amino acid processing endoproteases to be susceptible to compounds that are endocytosed by cells. As such, inhibitory drug compounds can be of any substance capable of being endocytosed including compounds that are at least partially, and preferably essentially completely, soluble in an aqueous (hydrophilic) solution. That is, inhibitory compounds of the present invention do not need to be lipophilic as the compounds need not cross cell membranes if "delivered" by endocytosis. Furthermore, inhibitors of cellular dibasic amino acid processing endoproteases are less likely to cause severe side effects since reductions in cellular dibasic amino acid processing endoprotease activity apparently are not significantly harmful to the cell. For a more detailed discussion, see Franzusoff et al., U.S. Pat. No. 5,413,914, entitled "Yeast Assay to Identify Inhibitors of Dibasic Amino Acid Processing Endoproteases", issued on May 9, 1995, which is incorporated herein by reference in its entirety.

In accordance with the present invention, a yeast-based assay such as that disclosed in U.S. Pat. No. 5,413,914, ibid., can be used to identify compounds that are capable of inhibiting the activity of dibasic amino acid processing endoprotease proteins of the present invention (e.g., TCPs and homologues thereof). Yeast strains possess a dibasic amino acid processing endoprotease located in the Golgi apparatus called Kex2 endoprotease that is capable of processing (i.e., cleaving) yeast precursor proteins having dibasic amino acid processing sites, such as precursor proteins for α-factor mating pheromones and killer toxins. Yeast strains lacking a functional Kex2 endoprotease can grow normally; such strains, however, are unable to mate and show reduced functions at low growth temperatures (i.e., at less than about 14° C.). Apparently all wild-type yeast strains, regardless of genus or species, produce a protease having Kex2-type activity (i.e., a Kex2 endoprotease) since all wild-type yeast strains apparently are capable of mating. As used herein, the phrases a "yeast strain lacking a functional Kex2 endoprotease" and a "Kex2 endoprotease-deficient yeast strain" each refer to a yeast strain in which the Kex2 endoprotease is either absent or modified such that the enzyme has essentially no proteolytic activity (i.e., less than about 10 percent, preferably less than about 5 percent, and more preferably less than about 1 percent of wild-type Kex2 endoprotease activity). As such, a Kex2 endoprotease-deficient strain is essentially unable to produce mature α-factor mating pheromones unless the strain is supplemented with a functional dibasic amino acid processing endoprotease, for example, by transforming the strain with a gene encoding a functional dibasic amino acid processing endoprotease, such as with a nucleic acid molecule of the present invention that encodes a protein having dibasic amino acid processing endoprotease activity.

One embodiment of the present invention is a method to identify a compound that inhibits proteolytic cleavage by a dibasic amino acid processing endoprotease of the present invention (i.e., a dibasic amino acid processing endoprotease that is encoded by a nucleic acid molecule of the present invention). The method includes the steps of (a) contacting a Kex2 endoprotease-deficient yeast strain that is transformed with a nucleic acid molecule of the present invention and that contains a precursor protein having a dibasic amino acid processing site with a putative inhibitory compound under conditions in which, in the absence of the compound, the yeast strain is capable of effecting cleavage of the precursor protein into cleavage products; and (b) assaying for production of at least one of the cleavage products. Production of a reduced amount of a (i.e., at least one) cleavage product in the presence of the putative inhibitory compound compared to in the absence of the putative inhibitory compound indicates that the compound is able to inhibit proteolytic cleavage by the endoprotease. The precursor protein can be either a yeast precursor protein or a heterologous precursor protein. In the instance of a system based on cleavage of a yeast precursor protein, the ability of the putative inhibitory compound to inhibit the cleavage of the yeast precursor protein is indicative of (positively correlates with) the ability of the putative inhibitory compound to inhibit the cleavage of a heterologous precursor protein; see U.S. Pat. No. 5,413,914, ibid. An advantage of using a Kex2 endoprotease-deficient strain expressing a dibasic amino acid processing endoprotease of the present invention is that such a method identifies compounds that interact with the endoprotease with high affinity and specificity without affecting cell viability. For example, a particularly preferred yeast strain to use to identify compounds that inhibit HIV infection is a Kex2 endoprotease-deficient *S. cerevisiae* strain that expresses hTCP. Other suitable and preferred dibasic amino acid processing endoproteases, as well as other suitable and preferred precursor proteins are disclosed herein.

The term yeast precursor protein refers to a precursor protein of the same species as the yeast strain used in the identification of inhibitory compounds in accordance with the present invention. Yeast precursor proteins are preferably produced endogenously by the yeast strain. Any yeast precursor protein having a dibasic amino acid processing site, the cleavage of which can be detected, can be monitored to determine whether the putative inhibitory compound can inhibit the ability of a dibasic amino acid processing endoprotease to cleave a heterologous precursor protein. Suitable yeast precursor proteins include, but are not limited to precursor proteins of α-factor mating pheromones and killer toxins. A preferred yeast precursor protein to monitor is a precursor (α-factor protein.

The phrases a precursor protein heterologous to a yeast precursor protein and a heterologous precursor protein each refer to a precursor protein that is naturally produced in a cell type other than the yeast strain used in the identification of inhibitory compounds in accordance with the present invention or that is produced synthetically and has a sequence that is not identical to a homologous yeast precursor protein. The heterologous precursor protein can be, for example, a precursor protein of an infectious agent or a labeled precursor protein that can be used as a marker in the method to identify compounds that inhibit dibasic amino acid processing endoproteases. A heterologous precursor protein can be a precursor α-factor protein that has a heterologous dibasic amino acid processing site, such as the processing site of an infectious agent. A heterologous precursor protein can be produced by a yeast strain of the present invention by genetically engineering the yeast strain to produce the protein, using recombinant techniques known to those skilled in the art to insert the gene encoding the protein into the yeast strain in a manner such that the yeast strain is capable of expressing (i.e., producing) the precursor protein (see, for example, Sambrook et al., *Molecular Cloning: A Laboratory Manual*, Cold Spring Harbor Labs Press, 1989; Pichuantes et al., in *Principles and Practice of Protein Engineering*, Wiley and Sons, 1995, in press, Cleland and Craik, eds.). Suitable and preferred heterologous precursor proteins are disclosed herein and in U.S. Pat. No. 5,413,914, ibid.

The use of a yeast-based assay in the present invention, particularly as an initial screen, to identify compounds that inhibit dibasic amino acid processing endoproteases of the present invention has several advantages. As a eukaryote, yeast have subcellular organelles and are able to perform many post-translational modifications in a manner similar to that effected by mammalian cells, such as N-terminal myristylation, prenylation, acetylation, phosphorylation, removal of N-terminal methionine, N- and O-linked glycosylation, disulfide bridge formation and protein oligomerization. Like bacteria, yeast are easy to manipulate both genetically and biochemically, easy to transform, grow rapidly (doubling times of about 1.5 to about 4 hours) on inexpensive medium, and produce heterologous proteins in large quantities. Thus, a yeast-based assay is less complicated, less expensive, and less time-consuming than an animal cell-based assay for the identification of inhibitory compounds. A number of putative inhibitory compounds can be screened in a rapid manner, either as pools of compounds or individually. Furthermore, a yeast-based assay to identify inhibitors of dibasic amino acid processing endoproteases that otherwise would enable propagation and spread of infectious agents obviates the need to work with live infectious agents to identify such inhibitory compounds. In addition, yeast can be genetically and recombinantly manipulated in a straight-forward manner to obtain strains that produce dibasic amino acid processing endoproteases of the present invention as well as yeast and/or heterologous precursor proteins. Use of yeast strains that lack a functional yeast Kex2 endoprotease but that can express a dibasic amino acid processing endoprotease of the present invention reduces potential interference by other cellular components being expressed by the cell type that endogenously produces the particular dibasic amino acid processing endoprotease.

Suitable yeast strains to use in the present invention include any Kex2 endoprotease-deficient yeast strain that can be transformed to produce a dibasic amino acid processing endoprotease of the present invention. The yeast can be haploid, diploid, or polyploid. Yeasts with higher ploidy typically exhibit less deleterious mutation effects. Preferred yeast strains include strains of the genera Saccharomyces, Pichia, Hansenula, Schizosaccharomyces, Kluyveromyces, Yarrowia and Candida. Preferred species include *Saccharomyces cerevisiae, Pichia pastoris, Hansenula polymorpha, Schizosaccharomyces pombe, Kluyveromyces lactis, Yarrowia lipolytica* and *Candida maltosa*. *S. cerevisiae* strains are particularly preferred because of the versatility of such strains including the ease with which such strains can be manipulated genetically and recombinantly, the ease with such strains can be cultured and induced to produce heterologous proteins, and the variety of strains available for use. Kex2 endoprotease-deficient yeast strains can be produced using a variety of methods known to those skilled in the art, preferably by genetic modification. A preferred genetic method to produce a Kex2 endoprotease-deficient strain is gene replacement (see, for example, Fuller et al., 1989, *Science* 246, 482–486; and Franzusoff et al., 1991, *J. Cell. Biol.* 112, 27–37). Recombinant methods to produce yeast strains for use in identifying inhibitor compounds are disclosed herein and in U.S. Pat. No. 5,413,914, ibid.

One embodiment of the present invention is a Kex2 endoprotease-deficient yeast strain that is transformed with a nucleic acid molecule of the present invention. The nucleic acid molecule preferably encodes an active dibasic amino acid processing endoprotease. Such a strain has particular utility in assay methods and test kits of the present invention. Preferred strains are also transformed with a heterologous precursor protein that can be cleaved by the heterologous dibasic amino acid processing endoprotease produced by the yeast strain.

The conditions under which the yeast strain is contacted with (e.g., mixed with, exposed to) the putative inhibitory compound are conditions in which the yeast strain can normally cleave a precursor protein having a dibasic amino acid processing site if essentially no inhibitor is present. Such conditions include an effective medium in which the yeast strain can be cultured such that the dibasic amino acid processing endoprotease produced by the yeast can exhibit biological activity (i.e., is capable of cleaving precursor proteins). Such conditions are disclosed in U.S. Pat. No. 5,413,914, ibid.

The present invention includes any of a variety of methods to determine if putative inhibitory compounds contacted with the yeast strain can inhibit cleavage of a yeast or heterologous precursor protein, including in vivo plate assays, such as α-factor zone clearing, or halo, assays, mating assays, and killer toxin halo assays; methods to separate precursor and cleavage proteins, such as centrifugation, chromatography, electrophoresis, filtration and chemical modification (e.g., biotinylation to detect presence of cleavage protein on cell surface); methods to directly measure cleavage (e.g., use of fluorigenic peptides which emit fluorescent light when cleaved); and antibody-based methods to detect and discriminate between precursor and cleavage proteins, such as immunoprecipitation followed by gel electrophoresis and immunoblot assays. Another method to detect cleavage is to culture yeast spheroplasts, in which case cleaved proteins are secreted into the medium, which can be analyzed by enzyme immunoassay (e.g., ELISA) or radioimmunoassay. Antibodies that selectively bind to a given precursor protein or its cleaved product can be produced using standard techniques, or purchased when available. Antibodies against an infectious agent can be isolated from the infected animal's serum. In one embodiment, secretion of cleaved proteins into the culture medium is detected using a dipstick assay in which, for example, an antibody raised against the cleaved protein is attached to the dipstick. If cleavage of the precursor protein is critical for syncytium formation (e.g., a precursor retroviral envelope protein), putative inhibitory compounds may be tested for their ability to prevent syncytium formation of envelope protein-expressing yeast spheroplasts with cells expressing receptors for the retrovirus. A number of these methods are described in detail in U.S. Pat. No. 5,413,914, ibid. A preferred method to use to identify inhibitory compounds is the α-factor zone clearing, or halo, assay. In one embodiment, the precursor α-factor protein is modified to include a heterologous dibasic amino acid processing site most preferred by the dibasic amino acid processing endoprotease being tested.

Another embodiment of the present invention is an in vitro method to identify a compound that inhibits a dibasic amino acid processing endoprotease of the present invention. The method includes the steps of (a) contacting a putative inhibitory compound with a secreted soluble dibasic amino acid processing endoprotease protein of the present invention in the presence of a precursor protein having a dibasic amino acid processing site under conditions in which, in the absence of said compound, the endoprotease protein is capable of effecting cleavage of the precursor protein into cleavage products; and (b) assaying for production of the cleavage products. Production of a reduced amount of cleavage products in the presence of the putative inhibitory compound compared to in the absence of the putative inhibitory compound indicates that the compound is able to inhibit dibasic amino acid processing endoprotease proteolytic cleavage. As used herein, a secreted soluble dibasic amino acid processing endoprotease protein of the present invention is a dibasic amino acid processing endoprotease of the present invention that retains proteolytic activity but that essentially lacks the transmembrane and C-terminal cytosolic domains. As such, the endoprotease protein can be secreted into the culture medium. Such a protein can be produced as described in U.S. Pat. No. 5,413,914, ibid. The ability of a putative inhibitory compound to inhibit dibasic amino acid processing endoprotease cleavage can be determined in a variety of ways as heretofore described, including plate assays, methods to separate precursor and cleavage proteins, methods to directly measure cleavage, and antibody-based methods to detect and discriminate between precursor and cleavage proteins.

Another embodiment of the present invention is a method to screen for compounds that inhibit the cleavage of a heterologous precursor protein by a heterologous dibasic amino acid processing endoprotease which includes several screening stages of increasing specificity. Such a method enables one skilled in the art to rapidly select an inhibitory compound of desired specificity from a large group of putative inhibitory compounds. It should be recognized that not all of the following screening stages are required and that one or more stages can be used in a variety of combinations and orders. Suitable stages and combinations thereof are disclosed in U.S. Pat. No. 5,413,914, ibid.

The present invention includes inhibitory compounds identified by the assay methods of the present invention. The term inhibitory compound refers to a compound that inhibits a dibasic amino acid processing endoprotease. A putative inhibitory compound is a compound that is being tested to determine if it is capable of inhibiting the dibasic amino acid processing endoprotease. The ability of a compound to inhibit a dibasic amino acid processing endoprotease refers to the ability of the compound to reduce the activity of the endoprotease, preferably to the extent that a substantial amount of precursor protein is not cleaved compared to cleavage effected by the endoprotease in the absence of the compound. The inhibition is preferably sufficient to interfere with the ability of an infectious agent that requires cleavage of such a precursor protein to propagate and spread to other cell types; that is, the inhibitor is able to reduce disease progression by the infectious agent. Inhibition of retroviral infection preferably includes reduction in infectivity, syncytium formation, and fusion between infected and uninfected cells.

A preferred inhibitory compound of the present invention is one that is specific for the dibasic amino acid processing endoprotease being targeted but that does not substantially adversely affect other cellular components, including other classes of proteases. That is, the compound can inhibit the targeted dibasic amino acid processing endoprotease with fewer side effects than drugs currently used for treatment, such as nucleoside analogs. Preferred inhibitory compounds are peptides, mimetopes, or mixtures thereof. As used herein, a mimetope is any organic compound that mimics the ability of a peptide to inhibit cleavage by a dibasic amino acid processing endoprotease. Such inhibition can be due to allosteric interactions with the protease as well as direct interactions with the catalytic domain. Mimetopes can be peptides in which the scissile peptide bond is replaced by a bond that cannot be cleaved by the endoprotease, for example by introducing a thio group. Alternatively, mimetopes can be synthetic or natural organic molecules, including nucleic acids, that have a structure similar to the dibasic amino acid processing site and, as such, bind with high affinity to the dibasic amino acid processing endoprotease.

A preferred concentration of the inhibitory compound to use in treatment is less than about 100 micromolar ($\mu$M), more preferably in the range of about 1 to about 10 $\mu$M and even more preferably in the range of about 1 to about 300 nanomolar (nM), which is the concentration at which apparently useful inhibitors of the HIV-1 encoded aspartyl protease are being administered. Inhibitory compounds delivered in such concentration ranges preferably inhibit at least about 50, and more preferably at least about 65, and even more preferably at least about 75 percent of the activity of the targeted dibasic amino acid processing endoprotease.

The inhibitory compound can effect either permanent or temporary inhibition by, for example, binding, respectively, irreversibly or reversibly to the dibasic amino acid processing endoprotease. The inhibitory compound may also modify the dibasic amino acid processing endoprotease, for example, by chemically inactivating the dibasic amino acid processing endoprotease. For example, an alkylating agent, such as chlorambucil, can be attached to a peptide having a dibasic amino acid processing site or a mimetope of such a peptide.

The inhibitory compound can further include a component that permits targeting of the compound to a particular cell type capable of producing the dibasic amino acid processing endoprotease. Such a component can include any substance that binds selectively to the cell type, such as an antibody, hormone, lymphokine, other ligand, or even a part of a viral envelope protein capable of binding to a receptor on the targeted cell type (e.g., at least a portion of HIV gp120 that can target the CD4 receptor on human CD4+ T-lymphocytes.), or portions thereof that retain binding activity.

One aspect of the present invention is the selection of putative inhibitory compounds to test in accordance with the present invention. Any compound can be tested; however, a preferred method to select putative inhibitory compounds is to follow a strategy similar to that used in identifying other protease inhibitors, such as inhibitors of the HIV-1 encoded aspartyl protease. Such a method and examples of putative inhibitory compounds are disclosed in more detail in U.S. Pat. No. 5,413,914, ibid. Putative inhibitory compounds can be tested in pools, using techniques known to those skilled in the art. Putative inhibitory compounds can be produced using techniques known to those skilled in the art.

The present invention also includes test kits to identify a compound capable of inhibiting a dibasic amino acid processing endoprotease of the present invention. Such kits include a Kex2 endoprotease-deficient yeast strain transformed with a nucleic acid molecule that encodes the dibasic amino acid processing endoprotease. The yeast strain also contains a precursor protein having a dibasic amino acid processing site that the yeast strain is capable of cleaving into cleavage products. The test kit also includes a means for determining the extent of cleavage by the yeast strain in the presence of a putative inhibitory compound. The determining means includes means for assaying for production of the cleavage products. Production of a reduced amount of cleavage products in the presence of the putative inhibitory compound compared to in the absence of the putative inhibitory compound indicates that the compound being tested is able to inhibit proteolytic cleavage by the dibasic amino acid processing endoprotease. Any suitable means to determine cleavage, including those heretofore disclosed, can be used. Examples of determining means are disclosed in U.S. Pat. No. 5,413,914, ibid.

In a preferred embodiment, test kits of the present invention are used to identify compounds that can inhibit infectious agents and thus treat or prevent disease. A particularly preferred test kit is capable of identifying compounds that reduce the infectivity of HIV. Compounds that are identified by test kits of the present invention as being able to inhibit cleavage of HIV gp160 into gp120 and gp41 can be used to treat HIV infection and to prevent or reduce the occurrence of AIDS.

The methods and test kits of the present invention are particularly useful in developing antiviral drugs that block cleavage of precursor envelope proteins by cellular dibasic amino acid processing endoproteases. One concern of targeting cellular proteases is whether the targeted cells will still function properly if the targeted dibasic amino acid processing endoproteases are inhibited by the antiviral drugs. Without being bound by theory, it is believed that inhibition of dibasic amino acid processing endoproteases will not be substantially harmful to the cells producing the dibasic amino acid processing endoproteases since Kex2 endoprotease-deficient yeast strains and Chinese hamster ovary cells apparently lacking a functional dibasic amino acid processing endoprotease are viable, as disclosed in U.S. Pat. No. 5,413,914, ibid. It is contemplated, however, that if inhibition of a cellular dibasic amino acid processing endoprotease reduces maturation of a key protein normally processed by that dibasic amino acid processing endoprotease (such as a hormone), the antiviral treatment can be supplemented by such a key protein.

One aspect of the invention is the development of targeted therapies to treat HIV infection and prevent the onset of ARC or AIDS. As such, a preferred therapy is one that is targeted to the human CD4+ T-lymphocyte dibasic amino acid processing endoprotease that naturally cleaves gp160, i.e., hTCP. Thus, a preferred method to prevent the spread of HIV is to (a) identify a compound that inhibits hTCP from cleaving an HIV gp160 precursor protein by (i) contacting putative inhibitory compounds with a Kex2 endoprotease-deficient yeast strain that produces hTCP and (ii) selecting a compound that can reduce cleavage of gp160; and (b)

administering the selected compound to a person in need of such a treatment.

The use of a test kit of the present invention in which a CD4+ T-lymphocyte dibasic amino acid processing endoprotease is produced by the yeast strain permits one to identify compounds that bind with high affinity to the correct binding pocket in the CD4+ T-lymphocyte dibasic amino acid processing endoprotease. Such compounds will be particularly useful therapeutics as they should exhibit a high specific activity that permits them to be administered in low dosages. It is also believed that relatively low doses of inhibitory compounds of the present invention will be sufficient for treatment because the relatively low abundance of yeast Kex2 endoprotease in cells and the relatively low activity of human CD4+ T-lymphocyte dibasic amino acid processing endoprotease in cleaving HIV gp160 suggest that cells produce relatively low amounts of dibasic amino acid processing endoproteases.

Targeting cellular dibasic amino acid processing endoproteases in accordance with the present invention permits inhibitory compounds to be delivered to the dibasic amino acid processing endoproteases by endocytosis, as heretofore disclosed. Inhibitory compounds of the present invention can be endocytosed by the cell membrane (fluid phase endocytosis). Alternatively, an inhibitory compound of the present invention can be a conjugate that includes a component that targets the compound to a receptor on a targeted cell type, in which case the compound is internalized by receptor mediated endocytosis.

The present invention also includes prodrugs, and production thereof, that include a dibasic amino acid processing site which are taken up by endocytosis and cleaved by dibasic amino acid processing endoproteases in the Golgi apparatus to produce an active drug. An example of a prodrug of the present invention is an active drug coupled to a positively or negative charged side group in such a manner that a dibasic amino acid processing site is situated between the active drug and the side group. The side group enables the prodrug to be hydrophilic, thereby allowing it to be soluble in bodily fluids and susceptible to endocytosis. After being endocytosed, the prodrug is transferred to the Golgi apparatus where it is cleaved by a dibasic amino acid processing endoprotease. Upon cleavage, the activated drug, if lipophilic, can migrate across the membrane into the cytoplasm of the cell. As such, the activated drug can be targeted against a cytoplasmic agent.

One embodiment of the present invention is a recombinant cell that includes a nucleic acid molecule that encodes a defective dibasic amino acid processing endoprotease protein of the present invention, that is a protein that encodes a dibasic amino acid processing endoprotease protein that has reduced or no dibasic amino acid processing endoprotease activity. Such a recombinant cell can be used in an ex vivo protocol to protect an animal from infection by an infectious agent that infects that cell type. Such a recombinant cell, or the nucleic acid molecule itself, can be used to produce a transgenic animal that has reduced susceptibility to infection by an infectious agent that requires dibasic amino acid processing endoprotease to propagate. The nucleic acid molecule can also be delivered to targeted cells in vitro or in vivo by a number of techniques. A preferred gene delivery technique is disclosed in pending U.S. patent application Ser. No. 08/340,185, entitled "Yeast-Based Delivery Vehicles", filed Nov. 15, 1994, which is incorporated by reference herein in its entirety.

In one embodiment, a therapeutic composition of the present invention which includes, for example, an inhibitory compound or a nucleic acid molecule that hybridizes to a nhTCP gene as described herein, can be delivered to a cell by a liposome. According to the present invention, a liposome comprises a lipid composition that is capable of targeting a nucleic acid molecule of the present invention to a particular, or selected, site in an animal. Preferably, the lipid composition of the liposome is capable of targeting to any organ and/or cell of an animal. Suitable liposomes for use with the present invention include any liposome. Preferred liposomes of the present invention include those liposomes standardly used in, for example, gene delivery methods known to those of skill in the art. In one embodiment, a liposome of the present invention comprises a compound capable of targeting the liposome to a CD4+ T cell and/or to a macrophage.

A liposome comprises a lipid composition that is capable of fusing with the plasma membrane of the targeted cell to deliver a nucleic acid molecule and/or inhibitory compound into a cell. Preferably, the transfection efficiency of a liposome is at least about 0.5 microgram ($\mu$g) of DNA per 16 nanomole (nmol) of liposome delivered to about $10^6$ cells, more preferably at least about 1.0 $\mu$g of DNA per 16 nmol of liposome delivered to about $10^6$ cells, and even more preferably at least about 2.0 $\mu$g of DNA per 16 nmol of liposome delivered to about $10^6$ cells. A preferred liposome is between about 100 and about 500 nanometers (nm), more preferably between about 150 and about 450 nm and even more preferably between about 200 and about 400 nm in diameter.

Complexing a liposome with a nucleic acid molecule or inhibitory compound of the present invention can be achieved using methods standard in the art. A suitable concentration of a nucleic acid molecule or inhibitory compound to add to a liposome includes a concentration effective for delivering a sufficient amount of nucleic acid molecule and/or inhibitory compound to a cell such that the infectivity of an infectious agent susceptible to inhibition of dibasic amino acid processing endoprotease activity is reduced in a desired manner. Alternatively, or additionally, a suitable concentration of a nucleic acid molecule or inhibitory compound to add to a liposome includes a concentration effective for delivering a sufficient amount of nucleic acid molecule and/or inhibitory compound to a cell that is capable of reducing the activity of dibasic amino acid processing endoprotease nhTCP. Preferably, nucleic acid molecules are combined with liposomes at a ratio of from about 0.1 $\mu$g to about 10 $\mu$g of nucleic acid molecule of the present invention per about 8 nmol liposomes, more preferably from about 0.5 $\mu$g to about 5 $\mu$g of nucleic acid molecule per about 8 nmol liposomes, and even more preferably about 1.0 $\mu$g of nucleic acid molecule per about 8 nmol liposomes.

Another preferred delivery vehicle comprises a recombinant virus particle vaccine. A recombinant virus particle vaccine of the present invention includes a therapeutic composition of the present invention, in which the nucleic acid molecules, including recombinant molecules, contained in the composition are packaged in a viral coat that allows entrance of DNA into a cell. A number of recombinant virus particles can be used, including, but not limited to, those based on alphaviruses, poxviruses, adenoviruses, herpesviruses, arena virus and retroviruses. A preferred recombinant virus particle of delivery of a nucleic acid molecule of the present invention into a cell are adenoviruses.

The present invention also includes therapeutic compositions that can be used to decrease dibasic amino acid processing endoprotease activity in order to reduce excess production of proteins that are derived from precursor proteins, such as cytokines, hormones, other immunoregulatory factors, other growth factors, and other regulatory factors. Such compositions include, but are not limited to, nucleic acid molecules that can reduce production of the proteins themselves or inhibitory compounds that reduce the activity of the dibasic amino acid processing endoproteases involved in maturation of those proteins. Such compositions can be used to immunomodulate an excessive immune response, such as in an autoimmune disease, to decrease the production of factors that stimulate tumor cell growth, or to otherwise modulate autocrine, paracrine, or endocrine function of cells that rely on dibasic amino acid processing endoproteases of the present invention, including CD4+ T-lymphocytes.

The present invention also includes therapeutic compositions that can be used to increase dibasic amino acid processing endoprotease activity. One embodiment of the present invention is a therapeutic composition comprising a nucleic acid molecule of the present invention that encodes an active dibasic amino acid processing endoprotease that can be delivered to a cell in vitro or in vivo in order to increase cleavage of precursor proteins in that cell. The cell to which the nucleic acid molecule is delivered can be a cell type that endogenously produces the dibasic amino acid processing endoprotease or a cell type that normally does not produce that dibasic amino acid processing endoprotease, in which case the cell is referred to as a surrogate. A number of methods can be used for gene delivery. A preferred method is the use of yeast-based delivery vehicles to deliver genes, as disclosed in Ser. No. 08/340,185, ibid. Such therapeutic compositions can be used, for example, to increase cytokine or hormone production, such as insulin production in diabetics or renin production in animal with high blood pressure. In one embodiment, the surrogate cell functions as an implant, or time-release capsule, to release a desired compound at an appropriate rate over time. Surrogate cells can be produced in vivo or can be produced ex vivo and then implanted at a desired site of action.

The present invention also includes a method to protect an animal from disease by administering to the animal a therapeutic composition of the present invention. In accordance with the present invention, the ability of a therapeutic composition of the present invention to protect an animal from disease refers to the ability of that composition to treat, ameliorate and/or prevent disease, including infection leading to disease. Animals to be treated using a therapeutic composition of the present invention include any animal that can be infected by an infectious agent that is susceptible to inhibition of dibasic amino acid processing endoprotease activity or any animal that is producing too much or too little of a protein that requires a dibasic amino acid processing endoprotease for maturation. Preferred animals to treat include mammals, birds, fish, amphibians and insects, with humans, livestock and pets being more preferred. Even more preferred are humans, apes, cats, dogs, cattle, horses, monkeys, swine and sheep with humans being particularly preferred.

The present invention also includes a method to reduce the infectivity of an infectious agent susceptible to inhibition of dibasic amino acid processing endoprotease activity in an animal. This method comprises contacting such dibasic amino acid processing endoproteases in the animal with a compound that inhibits the dibasic amino acid processing endoprotease activity of hTCP. Such inhibitory compounds, including nucleic acid molecules that hybridize to an hTCP gene of the present invention and/or transcription products thereof, have been described in detail herein.

Therapeutic compositions of the present invention can be administered by a variety of routes appreciated by those skilled in the art, and can vary depending on the form of the composition. Examples of routes to administer a therapeutic composition of the present invention include, but are not limited to, aural, bronchial, genital, inhalatory, nasal, ocular, oral, parenteral, rectal, topical, transdermal and urethral routes. Aural delivery can include ear drops, nasal delivery can include nose drops and ocular delivery can include eye drops. Oral delivery can include solids and liquids that can be taken through the mouth. Parenteral delivery can include intradermal, intramuscular, intraperitoneal, intrapleural, intrapulmonary, intravenous, subcutaneous, atrial catheter and venal catheter routes.

Methods to prepare and administer compositions via these routes are well known to those skilled in the art. Compositions of the present invention are administered in an effective manner which depends on the use of the composition. For example, in order to protect an animal from disease, a composition of the present invention is administered to the animal in an effective manner such that the composition is capable of protecting that animal from that disease. Compositions of the present invention can be administered to animals prior to disease in order to prevent disease and/or can be administered to animals after onset of the disease in order to treat the disease. Acceptable protocols to administer compositions in an effective manner include individual dose size, number of doses, frequency of dose administration, and mode of administration. Determination of such protocols can be accomplished by those skilled in the art.

Another embodiment of the present invention is a method to produce an animal model for studying the effect of TCP depletion, and the non-human animal model produced by such method. Such a method comprises administering to the animal a composition selected from the group of a nucleic acid molecule that selectively reduces expression of a dibasic amino acid processing endoprotease TCP gene by hybridizing to a nucleic acid molecule selected from the group consisting of a dibasic amino acid processing endoprotease TCP gene and transcription products thereof, and a compound that inhibits dibasic amino acid processing endoprotease activity, wherein said compound is identified by its ability to inhibit the activity of TCP. The individual steps of this method have been previously described herein. Preferably, such a non-human animal model includes, but is not limited to, a rat, a mouse and a non-human primate. In one embodiment, the animal model is produced by administration of a nucleic acid molecule and preferably an oligonucleotide that hybridizes to a regulatory region of a dibasic amino acid processing endoprotease TCP gene and transcription products thereof. According to the present invention, a TCP gene refers to a TCP gene from any mammal. The term, hTCP gene, refers to the TCP gene from a human.

Such an animal model for studying the effects of TCP depletion, can provide insight into diseases and mechanisms which may be affected by TCP. Such diseases and conditions include, but are not limited to, immune responses (e.g., autoimmunity), tumor biology, and inflammation.

The following examples are provided for the purposes of illustration and are not intended to limit the scope of the present invention. Standard techniques (e.g., recombinant DNA and culturing techniques) referred to in the examples are disclosed in a variety of references including, for example, Sambrook et al., ibid. and/or Guthrie et al. (eds.), 1991, Methods in Enzymology 194, Academic Press, San Diego.

EXAMPLES

Example 1

This Example describes the cloning and sequencing of a nucleic acid molecule of the present invention.

A nucleic acid molecule of about 483 nucleotides, denoted nhTCP$_{483}$, representing a partial human TCP gene, was isolated from human CD4+ T-lymphocyte polyA+ RNA in the following manner. Total RNA was extracted from human CD4+ T-lymphocyte CEM cells (available from American Type Culture Collection (ATCC), Rockville, Md.) and poly A+ RNA was separated from total RNA by oligo-dT cellulose chromatography using standard techniques. A first strand cDNA product was produced by incubating, under standard reverse transcription conditions, the polyA+ RNA and a degenerate primer having SEQ ID NO:7, namely 5' TCCCGTCGACHYCCCABSWRTGRRYDGW-CATGAA 3' (H is a mixture of A, T, and C; Y is a mixture of T and C; B is a mixture of G, T and C; S is a mixture of G and C; W is a mixture of A and T; R is a mixture of A and G; and D is a mixture of G, A and T).

Nucleic acid molecule nhTCP$_{483}$ was PCR amplified from the cDNA product using standard protocols and the following primers: a degenerate "sense" primer having SEQ ID NO:8, namely 5' TGTCGGATCCTGYGGNGTHGGH-GTDGCHTAYAAYKCC 3' (K is a mixture of G and T); and a degenerate "antisense" primer having SEQ ID NO:9, namely 5' TCCCGTCGACSGGDGCWGMDGCH-GAKGTSCCHGWRTG 3' (M is a mixture of A and C). The primers were designed from related protease sequences, particularly using the most conserved sequences shared by all known subtilisin-like enzymes and biased toward human gene sequences, and were intended to amplify a nucleic acid molecule comprising most, if not all, of the catalytic site. However, due to the high degeneracy required in designing primers, a number of primers needed to be tested in order to accomplish a successful amplification, requiring several iterations of design of appropriate primers. Of 8 primers tested, only 2 gave the correct product.

The amplified PCR fragment was recovered and submitted to standard DNA sequencing techniques. An about 483 nucleotide sequence of nhTCP$_{483}$ was determined and is presented as SEQ ID NO:1. SEQ ID NO:1 apparently encodes a protein of about 161 amino acids, which is presented as SEQ ID NO:2. Neither the translation initiation site of the protein nor the translation termination codon is contained within this nucleic acid molecule.

Comparison of the deduced nucleic acid sequence of nhTCP$_{483}$ (i.e., SEQ ID NO:1) with the nucleic acid sequence of the genes encoding human furin (hFUR), human PC1 (hPC1), human PC2 (hPC2), human PC4 (hPC4), mouse PC5 (mPC5) and rat PC5 (rPC5) indicated that SEQ ID NO:1 was about 70%, 66.7%, 57.7%, 63.7% and 85% identical to the corresponding region of the respective genes. The deduced amino acid sequence SEQ ID NO:2 was about 71.6%, 66.1%, 56.4%, 73.5% and 95.1% identical to the respective corresponding regions of hFUR, hPC1, hPC2, hPC4, mPC5 and rPC5.

Example 2

This Example describes the cloning and sequencing of another nucleic acid molecule of the present invention.

A nucleic acid molecule of about 2400 nucleotides, denoted nhTCP$_{-2400}$, representing a partial human TCP gene, was PCR amplified from the cDNA product described in Example 1 using standard protocols and the following primers: a degenerate "sense" primer having SEQ ID NO:10, namely 5' CCAAGYATGTGGTAYATGCAYTGY-AGY 3'; and a degenerate "antisense" primer having SEQ ID NO:11, namely 5' GGCTGCTCAGCCTTGGAATGTA-CATGTTTT 3'. The primers were designed using mouse and rat PC5 gene sequences. The antisense primer spans the translation stop codon of the mouse and rat PC5 genes.

The amplified PCR fragment was recovered and submitted to standard DNA sequencing techniques. An about 111 nucleotide sequence of the 5' end of nhTCP$_{-2400}$ was determined and is presented as SEQ ID NO:3. SEQ ID NO:4 apparently encodes the first 37 amino acids of hTCP$_{-800}$ and is presented as SEQ ID NO:4.

Comparison of SEQ ID NO:2 and SEQ ID NO:4 with mouse and rat PC5 proteins indicates that SEQ ID NO:4 is amino terminal to SEQ ID NO:2 and that SEQ ID NO:4 as well as SEQ ID NO:2 contain portions of the catalytic domain.

Comparison of SEQ ID NO:3 with the sequences of the genes encoding rPC5 and mPC5 indicates that SEQ ID NO:3 is about 91.9% identical with the corresponding regions of the rat and mouse genes. The amino acid sequences of the three proteins in that region are identical. When compared with the mature rPC5 and mPC5 proteins, the amino terminus of the protein encoded by nhTCP$_{-2400}$ lacks only about the first 17 amino acids of the corresponding region of the mature rPC5 and mPC5 proteins.

Additional nucleic sequence analysis of nhTCP$_{-2400}$ yielded two nucleic acid sequences: (a) an 918 nucleotide sequence at the 5' end of nhTCP$_{-2400}$, referred to herein as SEQ ID NO:12, which encodes an amino acid sequence of 306 amino acids, referred to herein as SEQ ID NO:13; and (b) an 867 nucleotide sequence at the 3' end of nhTCP$_{-2400}$ (including the stop codon), referred to herein as SEQ ID NO:14, which encodes an amino acid sequence of 288 amino acids, referred to herein as SEQ ID NO:15. SEQ ID NO:12 includes both SEQ ID NO:1 and SEQ ID NO:3 in that SEQ ID NO:1 begins at nucleotide position 280 of SEQ ID NO:12, and SEQ ID NO:3 begins at nucleotide position 16 of SEQ ID NO:12. At certain positions in SEQ ID NO:12 and in SEQ ID NO:14, the nucleotide was not identified and is denoted "N".

In order to compare the nucleotide and amino acid sequences with those of mouse PC5, the "N"s were changed to "A"s. Comparison of SEQ ID NO:12 and SEQ ID NO:14 with the corresponding regions of the mouse PC5 gene indicated that the human gene shares about 85% nucleic acid sequence identity with the corresponding regions of the mouse gene. Comparison of SEQ ID NO:13 with the corresponding region of mouse PC5 indicated that SEQ ID NO:13 was about 99% identical to the corresponding region of the mouse protein. Comparison of SEQ ID NO:15 with the corresponding regions of mouse PC5 indicated that SEQ ID NO:15 was about 88% identical to the corresponding region of the mouse protein.

Example 3

This Example demonstrates that a gene including nhTCP$_{483}$ is transcribed in human CD4+ T-lymphocytes as well as in a human colon carcinoma line.

Total and polyA+ RNA was isolated from human CD4+ T-lymphocyte CEM and H9 (available from ATCC) cell lines and from human colon carcinoma LoVo cells (also available from ATCC) using standard procedures. The RNA populations were submitted to Northern blot analysis according to standard procedures and were probed with the labelled nucleic acid molecule nhTCP$_{483}$. The probe hybridized with RNA species of about 3.5 kb and about 6 kb in all cell lines. The RNA species of about 3.5 kb is of a size expected to encode a protein having a size similar to that of mouse or rat PC5, and corresponds to a PC6A gene. The identity of the larger molecular weight species is the PC6B gene; a larger molecular weight RNA is also found in similar experiments using mouse or rat PC5 gene probes.

A similar experiment in which a probe corresponding to the human furin gene was used in Northern analysis of RNA isolated from each of the three cell lines indicated that furin is also expressed by each of these cell lines. Further experiments in which a probe corresponding to the human PC7/8 (hPC7/8) gene was used in a Northern analysis of human CD4+ T cells and LoVo cells indicated that PC7/8 is expressed by each of these cell lines. It is of interest that even though these cell lines produce furin and PC7/8, another enzyme, namely hTCP, is also produced, suggesting the latter's distinct role in processing proteins having dibasic amino acid processing sites, such as being able to function in a particular cellular compartment and/or to cleave a particular substrate, such as has been found for the processing of the multivalent precursor protein propiomelanocortin which is cleaved by PC1 and PC2 at distinct sites within the molecule (see Zhou et al., 1993, *J. Biol. Chem.* 268, 1763–1769).

Example 4

This Example describes the production of certain recombinant molecules and recombinant cells of the present invention.

Recombinant molecule pα/nhTCP$_{-2400}$ is prepared as follows. Nucleic acid molecule nhTCP$_{-2400}$, produced as described in Example 1, is ligated to a nucleic acid sequence encoding a *S. cerevisiae* α-factor signal segment to form an α-signal/nhTCP$_{-2400}$ fragment, denoted herein as α/nhTCP$_{-2400}$. The α/nhTCP$_{-2400}$ fusion gene is operatively linked to *S. cerevisiae* ADH2/GAPDH promoter and CYC1 transcription termination sequences and joined with other yeast shuttle expression vector sequences to form recombinant molecule pα/nhTCP$_{-2400}$. Recombinant molecule pα/nhTCP$_{-2400}$ contains yeast (2μ) and bacterial replication control sequences as well as a bacterial gene encoding ampicillin resistance (Amp), and auxotrophic leu2-d and prototrophic URA3 yeast genes.

Recombinant molecule pα/nhTCP$_{-2400}$ is transformed into *S. cerevisiae* CB023, a cir° strain that is disclosed in Brenner et al., 1992, *Proc. Natl. Acad. Sci.* 89, 922–926 to form recombinant cell *S. cerevisiae* CB023:pα/nhTCP$_{-2400}$.

Recombinant molecule pα/nhTCP is produced in a similar manner to recombinant molecule pα/nhTCP$_{-2400}$ except that the entire coding region of hTCP is included in the recombinant molecule. Recombinant cell *S. cerevisiae* CB023:pα/nhTCP is produced by introducing recombinant molecule pα/nhTCP into *S. cerevisiae* CB023.

Culturing of recombinant cells *S. cerevisiae* CB023:pα/nhTCP$_{-2400}$ and *S. cerevisiae* CB023:pα/nhTCP under appropriate conditions leads to the production of TCP proteins of the present invention.

Example 5

This Example describes the production of another recombinant molecule and recombinant cell of the present invention. Such a recombinant cell can be used to identify inhibitors of HIV gp160 cleavage.

Recombinant molecule pα/env (also denoted pBS8) that includes the gene encoding HIV-1$_{SF2}$ gp160, was produced as described in Example 1 of U.S. Pat. No. 5,413,914, ibid. Briefly, the envelope (env) gene encoding the gp160 precursor envelope protein (about 825 amino acids) of HIV-1$_{SF2}$ (Sanchez-Pescador et al., 1985, *Science* 227, 484–492) was ligated to a nucleic acid sequence encoding an α-factor signal and leader segment of about 86 amino acids to form an α-leader/env-gene fragment (α/env) in which the signal sequence of the env gene was replaced by the α-factor signal and leader sequences in a manner similar to the method by which the epidermal growth factor gene was joined to α-factor signal and leader sequences in Brake et al., 1984, *Proc. Natl. Acad. Sci.* 81, 4642–4646. The α-factor segment, also denoted α-F leader, also included a dibasic amino acid processing site at its carboxyl terminus. The α/env fusion gene was operatively linked to a *S. cerevisiae* ADH2/GAPDH promoter and α-factor transcription termination sequences and joined with other yeast shuttle expression vector sequences to form recombinant molecule pα/env, also denoted pBS8. Recombinant molecule pα/env contains yeast (2μ) and bacterial replication control sequences as well as a bacterial gene encoding ampicillin resistance (Amp), and auxotrophic leu2-d and prototrophic URA3 yeast genes.

Recombinant molecules pα/env and pα/nhTCP, produced as described in Example 5, are transformed into a *S. cerevisiae* Kex2 endoprotease-deficient strain, called *S. cerevisiae* kex2Δ, which has the genotype pep4::URA3 kex2::TRP1 prb leu2 his4 ura3 trp1 and was produced as described in Example 3 of U.S. Pat. No. 5,413,914, ibid. The transformed strain, denoted *S. cerevisiae* kex2Δ:pα/env,pα/nhTCP is cultured under conditions suitable to produce gp160 and hTCP. The ability of hTCP to cleave gp160 into gp120 and gp41 is demonstrated using immunoprecipitation and immunoblot techniques similar to those disclosed in Example 1 of U.S. Pat. No. 5,413,914, ibid. The ability of *S. cerevisiae* kex2Δ:pα/env,pα/nhTCP to express gp120 and gp41 on its cell surface is demonstrated using a cell surface biotinylation assay similar to that described in Example 1 of U.S. Pat. No. 5,413,914, ibid.

Example 6

This example demonstrates the ability to identify inhibitors of HIV-1 infection using a Kex2 endoprotease-deficient *S. cerevisiae* strain transformed with a gene encoding the human CD4+ T-lymphocyte dibasic amino acid processing endoprotease that can cleave HIV-1 gp160 precursor proteins.

*S. cerevisiae* kex2Δ:pα/env,pα/nhTCP, produced as described in Example 5, is cultured according to standard techniques (see, for example, Guthrie et al. (eds.), ibid.) and divided into samples that are placed, for example, in microtiter dish wells. Each sample is incubated with about 300 μM, 100 μM, 10 μM, 1 μM, 300 nM, 100 nM, 10 nM, 1 nM, or none of one of the following peptides: Boc-Arg-Glu-Lys-Arg-MCA or Boc-Gln-Arg-Arg-MCA under culturing conditions for about 12 hours. Putative inhibitory compounds can be pre-incubated with the yeast strain prior to induction of gp160 expression. After culturing, cells from each sample are lysed and submitted to immunoprecipitation and/or immunoblot analysis to measure gp160, gp120, and gp41 production, using the techniques described in Example 5. Peptides that inhibit cleavage of gp160 to gp120 at suitable doses are identified and can be further tested for their ability to inhibit syncytium and/or infectious virus formation by HIV-1-infected CD4+ T-lymphocytes, using techniques such as those disclosed herein and in U.S. Pat. No. 5,413,914, ibid.

Example 7

This Example describes the cloning and sequencing of additional nucleic acid molecules of the present invention, including nucleic acid molecules having apparent full-length coding regions.

A nucleic acid molecule of about 444 nucleotides, denoted herein as $nhTCP_{444}$ and including nucleotides encoding the amino terminus of hTCP, was PCR amplified from the cDNA product described in Example 1 using standard protocols and the following primers: a degenerate sense primer having SEQ ID NO:24, namely 5' AGCGT-NGGNACNATGGAYTGGGAYTGG 3' (N is a mixture of A, T, G and C; Y is a mixture of T and C); and a degenerate antisense primer having SEQ ID NO:25, namely 5' RTTRT-CRCTRCARTGCATRTACCACAT 3' (R is a mixture of A and G). These primers were designed using mouse and rat PC6 gene sequences, and correspond to nucleotides 19–45 and 436–462, respectively, of the mouse and rat PC6 (also referred to as PC5) sequences, as reported in Lusson et al., ibid. The amplified PCR product was recovered and submitted to standard DNA sequencing techniques. An about 445 nucleotide sequence of $nhTCP_{444}$ was determined and is represented herein as SEQ ID NO:16.

Nucleic acid molecule $nhTCP_{2766}$, which contains an apparent full-length open reading frame, was produced by PCR gene splicing by overlap extension (as described, for example, by Horton et al., 1990, *Biotechniques* 8, 528–535) using $nhTCP_{444}$ and $nhTCP_{-2400}$. The amplified PCR product was recovered and submitted to standard DNA sequencing techniques. An about 2766 nucleotide sequence of $nhTCP_{2766}$ was determined and is presented as SEQ ID NO:17. Translation of SEQ ID NO:17 indicates that $nhTCP_{2766}$ encodes a protein of about 915 amino acids, denoted herein as $hTCP_{915}$, the sequence of which is presented in SEQ ID NO:18. SEQ ID NO:18 corresponds to an open reading frame of about 2745 nucleotides, denoted herein as $nhTCP_{2745}$, the nucleic acid sequence of which is presented herein as SEQ ID NO:19.

Comparison of SEQ ID NO:19 with the nucleic acid sequences of the genes encoding mouse and rat PC6 proteins indicated that SEQ ID NO:19 was about 80% identical to the corresponding regions of the rat and mouse genes. The deduced amino acid sequence of SEQ ID NO:18 was about 96% identical to the corresponding regions of the rat and mouse proteins.

Further analysis of SEQ ID NO:18 suggested that $hTCP_{915}$ includes a signal segment of about 34 amino acids, spanning from about amino acid 1 through about amino acid 34 of SEQ ID NO:18, a "pro" region of about 82 amino acids spanning from about amino acid 35 through about amino acid 116 of SEQ ID NO:18, and a putative mature protein of about 799 amino acids, spanning from about amino acid 117 through about amino acid 915 of SEQ ID NO:18. The deduced proprotein, denoted herein as $hTCP_{881}$, has an amino acid sequence represented herein as SEQ ID NO:21, which is encoded by a nucleic acid molecule denoted $nhTCP_{2643}$, the nucleic acid sequence of which is represented herein as SEQ ID NO:20. The deduced putative mature protein, denoted herein as $hTCP_{799}$, has an amino acid sequence represented herein as SEQ ID NO:23, which is encoded by a nucleic acid molecule denoted $nhTCP_{2397}$, the nucleic acid sequence of which is represented herein as SEQ ID NO:22. The predicted molecular weight of this putative mature dibasic amino acid processing endoprotease, excluding post-translational modifications (i.e., based on amino acid sequence alone) is about 88 kilodaltons.

Example 8

This Example demonstrates that $nhTCP_{2766}$ is expressed in primary human CD4+ T lymphocytes and in HIV-1 sensitive Jurkat T cells. This Example, in conjunction with Example 3, also indicates that proteins of the present invention include those that are necessary and sufficient for HIV-1 gp160 processing, and provides evidence that other candidate dibasic amino acid processing endoproteases are not necessary for HIV-1 gp160 processing.

Primary human CD4+ T lymphocytes were isolated from peripheral blood of a healthy adult donor using MicroCEL-Lector T-25 cell culture flasks (available from Applied Immune Sciences, Inc., Santa Clara, Calif.). The CD4+ T-lymphocytes were purified by the panning technique, using plates coated with anti-human CD4 antibodies, eluted and assayed for enrichment by fluorescence activated cell sorting (FACS) analysis. By this strategy, CD4+ T-lymphocytes comprised ~85% of the enriched cell population.

Total RNA samples from the primary CD4+ T-lymphocytes, CEM cells and HIV-1 sensitive Jurkat T cells (available from ATCC) were isolated and submitted to Northern blot analysis as described in Example 3, using a nhTCP-specific probe corresponding to the 5' end of $nhTCP_{2766}$. Approximately the same amount of nhTCP mRNA was detected in each of the three T lymphocyte samples. Further experiments indicated that the hTCPA and the hTCPB isoforms of hTCP and hPC7/8 are expressed in human CD4+ T lymphocytes, but neither PACE4 nor PC1 mRNAs were detected in these human CD4+ T lymphocytes.

LoVo cells derived from a human colon adenocarcinoma (described in Example 3) have been shown to express an mRNA for furin that, although full-length, encodes a truncated, defective protease (see Takahashi et al., 1993, *Biochem. Biophys. Res. Comm.* 195, 1019–1026). Therefore, these cells have proven useful for testing the cleavage efficiency of a variety of transfected precursor proteins by dibasic amino acid processing endoproteases. It has been hypothesized by others that furin is responsible for HIV-1 gp160 cleavage activity. The recognition sequence at the cleavage junction (R-E-K-R) makes gp160 a good furin substrate in vitro. Support for the furin hypothesis has come from studies showing that furin overproduction by transfection or by expression from vaccinia virus vectors in a variety of non-lymphoid and human T cell lines improves the efficiency (to ~60–80%) of gp160 cleavage. The furin hypothesis was also favored since the enzyme is present in the constitutive pathway of a broad spectrum of cells, tissues and organs. Since it has been assumed that gp160 travels the "constitutive" pathway, then it was logical to presume that furin would be responsible for cleaving the gp160 precursor. Finally, numerous precursor proteins, including envelope glycoproteins from Newcastle disease virus (NDV) and influenza virus, definitely require furin for processing.

The hypothesis that furin is responsible in gp160 cleavage in HIV competent cells, however, is not supported by all of the available data, and is seriously brought into question by the data of the present inventors. In fact, overexpression of furin results in both legitimate and illegitimate cleavage of gp160, such that gp160 is processed at multiple sites in these cells, rather than solely at the junction between gp120 and gp41. In contrast, env gene transfection into CD4⁻ or CD4⁺ lymphocytes results in a lower efficiency (5–20%) of gp160 processing by the endogenous protease, and is identical to that observed in HIV-infected human T cells. It has been observed that furin is expressed at significant levels in human T cells; therefore, the furin levels do not explain the lower efficiency of gp160 cleavage in T cells. Further evidence that furin is not the endogenous gp160 SPC protein was provided by Ohnishi et al., 1994, *J. Virol.* 68, 4075–4079, who found that the Newcastle disease virus (NDV) envelope Of glycoprotein processing was eliminated in LoVo cells, suggesting that furin is responsible for that cleavage. Ohnishi et al., ibid., also found that transfection of the HIV-1 genome into LoVo cells gave rise to infectious virions, demonstrating that HIV-1 gp160 precursor processing occurred even in the absence of a functional furin protease. In addition, Gu et al., 1995, *FEBS Lett.* 365, 95–97, showed that infectious HIV virions are produced in another furin-defective cell line, CHO-FD11, in the absence of furin activity, confirming that furin is not required, and that another protease is sufficient, for HIV-1 gp160 maturation. Gu et al., supra, further demonstrated that NDV and influenza proteins were not processed in these furin-defective cells. Without being bound by theory, the present inventors believe that this finding is significant, because it suggests that the subcellular location of subtilisin-like protein convertases (SPC proteases) is very important to their function, and further emphasizes that the proteases do not change their intracellular itinerary to substitute for one another.

Northern blot analysis of total RNA isolated from LoVo cells using nhTCP-based probes (i.e., the 5' probe described in this Example and the catalytic domain-containing probe described in Example 3) indicated that LoVo cells produced nhTCP transcripts. In a separate Northern-blot experiment, it was shown that although LoVo cells expressed a PACE4 mRNA, they did not express a PC1 mRNA.

In summary, human CD4+ T lymphocytes and human LoVo cells (a) both process HIV gp160 and (b) both express nhTCP genes. Since human CD4+ T lymphocytes apparently do not produce PACE4 and PC1, those enzymes are not necessary for HIV gp160 cleavage. Although T lymphocytes do produce furin, LoVo cells do not produce an active furin and yet are still able to effect HIV gp160 cleavage. Thus, these results (as well as those in Example 3) suggest that hTCP is necessary and sufficient for cleavage of HIV gp160. These experiments do not rule out a role for PC7/8 in HIV gp160 processing, but the experiments described below in Example 9 strongly indicate that hTCP, and not PC7/8, is the endogenous SPC protease that is solely responsible for gp160 cleavage.

Example 9

This Example demonstrates that HIV-1 virions from cell lines treated with hTCP antisense constructs are not infectious.

hTCP-defective cell lines were genetically engineered to test the requirement for hTCP in HIV-1 gp160 processing and viral infectivity. Antisense approaches (as described in Homann et al., 1993, *Nucl. Acids Res.* 21, 2809–2814 and Uhlenbeck, 1993, Antisense Res. Dev., Chp. 6, pp 83–96; both of which are incorporated herein by reference in their entireties) were used to interfere with expression of the hTCP gene in target cells. The initial, successful attempts were performed in human LoVo colon carcinoma cells for several reasons: i) LoVo cells are far more efficient for transient transfection than T lymphocytes, which provided the opportunity to examine the efficacy of multiple constructs; ii) LoVo cells, when transfected with the HIV genome, are competent for the production of infectious virions, despite the absence of furin activity; iii) LoVo cells express both isoforms of hTCP (A and B), as well as other SPC proteases: hPC8, hPACE4, and the defective furin (with multiple SPC protease members, the specificity of the antisense constructs in deleting all or individual SPC proteases could be evaluated); and finally, iv) the LoVo cell line exhibits healthy growth characteristics, such that negative consequences of introducing antisense constructs on cell growth would be evident.

Several antisense constructs for the disruption of hTCP expression were engineered, focusing on the sequences in the 3' end of the gene, which is unique in each SPC member. For the following experiments, an antisense construct having the nucleic acid sequence represented by SEQ ID NO:27 was designed. SEQ ID NO:27 is the complement of the nucleic acid sequence denoted SEQ ID NO:26. SEQ ID NO:26 represents nucleotides 924 through 2268 of SEQ ID NO:17. The antisense construct is driven by the CMV promoter in the pCI-neo vector (Invitrogen). Initial experiments with transient transfection of these constructs into LoVo cells revealed that hTCP expression was decreased, without impact on furin mRNA (data not shown). Based on those observations, stably transfected cell lines were isolated and evaluated. Eight stable cell lines were selected for closer examination of gene expression by RT-PCR analysis. The 8 lines fell into 3 classes: i) those cells that exhibited similar levels of hTCP expression as the parent LoVo cell line (designated as isolates 1, 2 and 8); ii) three isolates showed no hTCP mRNA (designated as isolates 5, 6 and 7); and iii) those isolates that exhibit very low, but detectable levels of hTCP message (designated as isolates 3 and 4). One representative member from each class (isolates 1, 4 and 6, referred to hereafter as cell lines #1, #4 and #6) was examined for antisense effects on the expression of other genes. RT-PCR and RNAse protection analyses demonstrated that this hTCP antisense construct reduced or eliminated hTCP expression in cell lines #4 and #6, respectively, with no effect on furin, hPACE4, actin or GAPDH mRNA. It is also important to note that these stably transfected cell lines were viable, exhibiting growth characteristics like the parent LoVo cell line. This point illustrates that interfering with expression of the SPC proteases is apparently not toxic to cells, highlighting the therapeutic potential of these cellular enzymes as anti-viral targets.

One test for the requirement of a SPC protease in gp160 processing is to monitor the effects of the SPC protease depletion on HIV infectivity. LoVo cells transfected with the HIV-1 genome are competent for producing virions that can infect CD4⁺ cells. For this test, the HIV-1 genome from the PNL4-3 viral isolate was transfected into the parent LoVo and hTCP antisense-treated derivatives (hereafter referred to as cell lines #4 and #6, as defined in the previous section). At different times after transfection with the HIV-1 genome, the supernatants from the different cell lines were harvested and the amount of HIV present in the supernatant was detected by p24 ELISAs (see for example, Renneisen et al., 1990, *J. Biol. Chem.* 265:16337–16342, which is incorporated herein by reference in its entirety).

More specifically, as described above, duplicate wells of the parent LoVo cells, as well as the #4 and the #6 hTCP antisense-treated cell lines were transfected with the HIV-1 genomic DNA. At days 0, 1, 3, 5 and 7 post-transfection, the supernatants were harvested and virions were quantified by p24 ELISAs. The p24 levels in the supernatants from each of the cell lines was nearly identical over time, indicating that the hTCP antisense construct exerted no negative impact on cell viability, as measured by the cellular capacity for virion production (FIG. 1). The virions derived from the cell lines were then incubated with CD4+ cells in two independent assays of viral infectivity.

Figure 2:
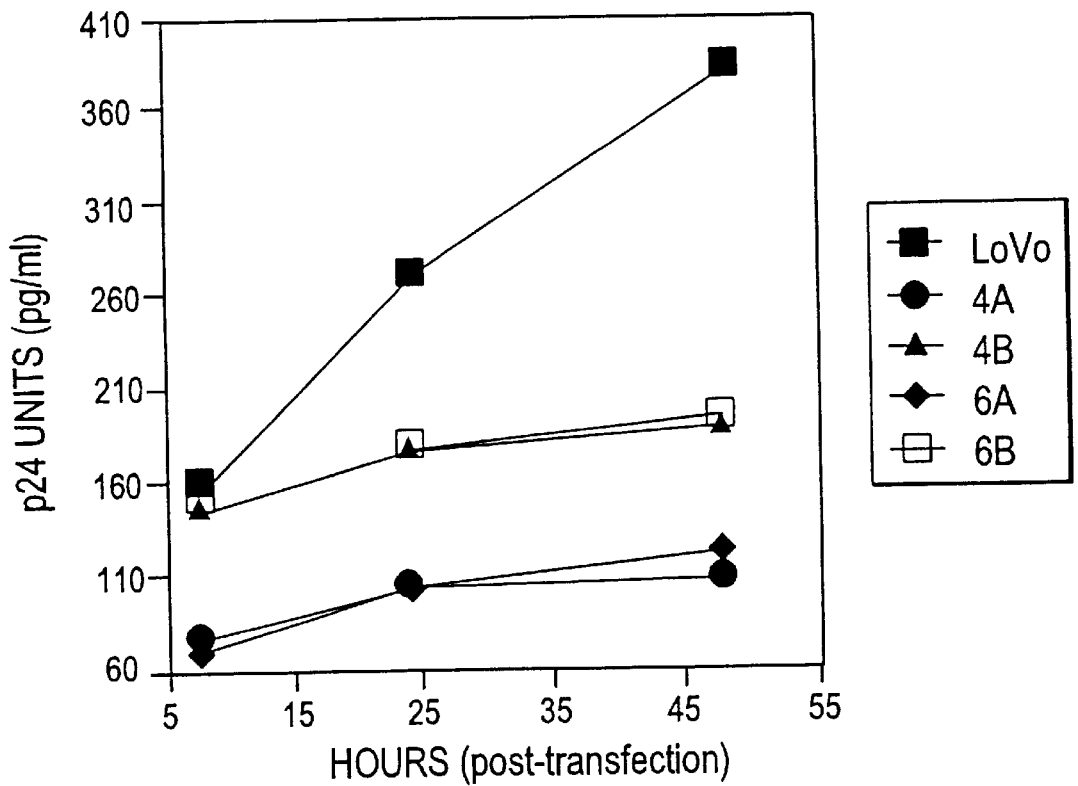
FIG. 2 is a graph showing results from a p24 ELISA which demonstrates that HIV-1 virions derived from LoVo cells transfected with nhTCP antisense constructs are not infectious.

In the first approach, a limiting dilution infectivity assay, the virions harvested from the different cell lines were added to H9 or Jurkat T cell lines, and then subsequent rounds of HIV virion release into the T cell supernatants was monitored by p24 ELISA. More particularly, equivalent aliquots of p24-containing supernatants were incubated with H9 cells for 2 h, the cells were washed, and fresh media was added to the cells for the limiting dilution infectivity assay. At different times after initial incubation with the T cells, the supernatants were assayed for p24 released from the cells. The data shown in FIG. 2 represent the mean of triplicate p24 determinations from a representative experiment. As previously observed, virions released from the parent LoVo cells are infectious and therefore exhibit steady linear increases in p24 units released into the T cell supernatants over time (FIG. 2). In contrast, when the input virions were derived from the hTCP antisense-treated cell lines, #4 and #6, p24 released into the T cell supernatants remained at baseline over time. Therefore, the virions derived from hTCP-antisense treated cell lines are not infectious.

In the second infectivity assay, known as the MAGI assay (described in Kimpton et al., 1992, *J. Virol.* 66, 2232–2239; and Vodicka et al., 1997, *Virol.* 233, 193–198, both references of which are incorporated herein by reference in their entireties), the virions are incubated with HeLa-CD4+ cells that harbor the β-galactosidase gene under the control of the HIV-1 LTR promoter. Infected cells are then stained for β-galactosidase activity; the number of stained cells reflects the titer of infectious virions. Both the p24 ELISA and the MAGI assays efficiently monitor HIV infectivity, yet the MAGI assay reports the activity from a single round of infection, rather than requiring multiple rounds of virion production and infection. The results described here were obtained with the original MAGI assay cell line, although a newer version of these cells has been created which also harbor elevated levels of the co-receptors for HIV infection, which presumably increases the efficiency of viral infectivity.

Figure 3:
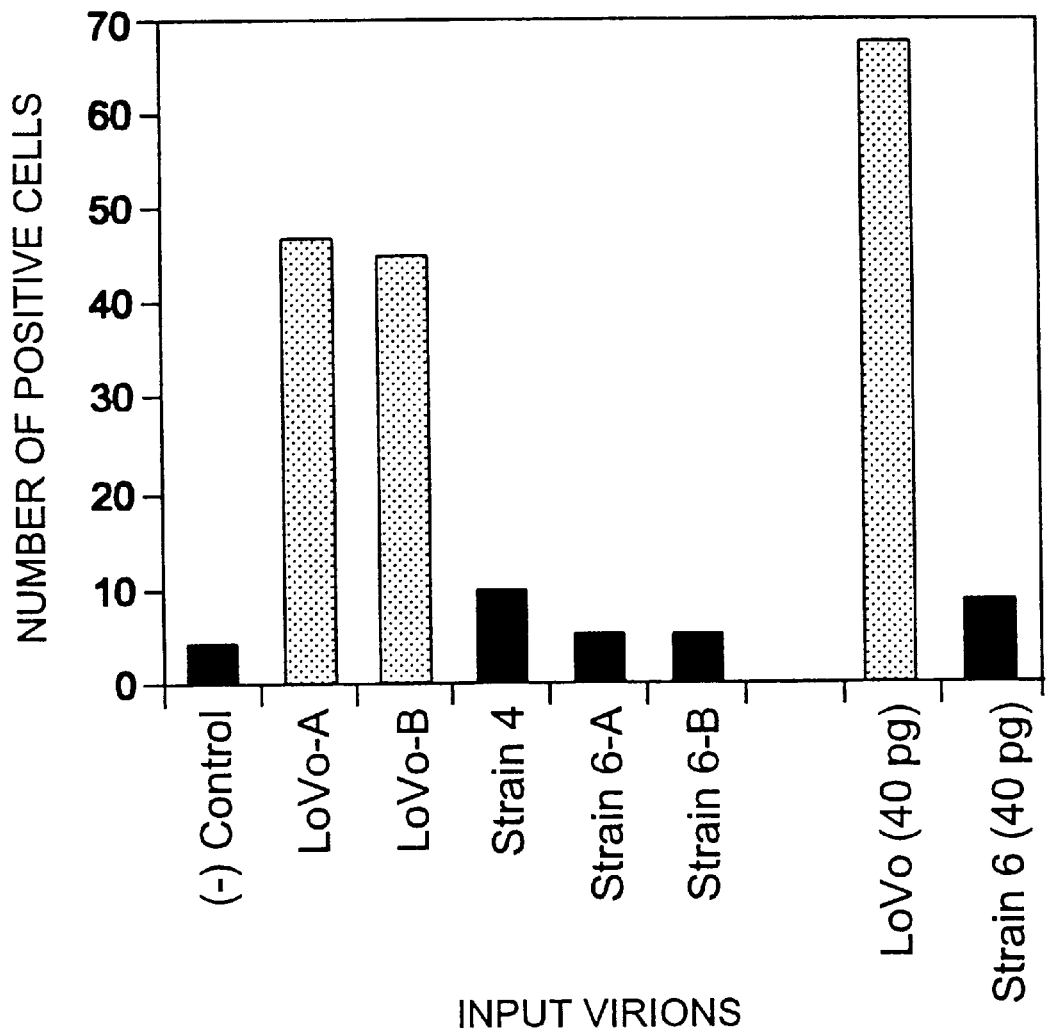
FIG. 3 is a bar graph showing results from a MAGI assay illustrating that HIV-1 virions derived from LoVo cells transfected with nhTCP antisense constructs are not infectious.

In this assay, duplicate aliquots of supernatant with equivalent p24 units (produced as described above from the different cell lines) were incubated with the HeLa-CD4+ cells harboring the HIV-1 LTR-β-galactosidase construct. After 48 h, the cells were stained for β-galactosidase activity. The virions derived from the parent LoVo cells infected a significant number of the target cells (FIG. 3). Doubling the initial concentration of p24 units added to the target cells caused a concomitant increase in the number of β-galactosidase staining cells. However, the virions derived from the hTCP antisense-treated cells, especially those from cell line #6 (which had no detectable hTCP RNA), did not trigger β-galactosidase staining above background levels. This is a representative experiment of eight performed to date. Hence, by two different criteria, virions derived from HTCP antisense-treated cells were not infectious, indicating that HTCP is important for HIV-1 gp160 maturation and viral infectivity.

In summary, members of the SPC protease family are responsible for HIV-1 gp160 precursor processing in the secretory pathway of human T cells. By investigating the profile of SPC proteases expressed in human T cells, the present inventors discovered the human hTCP proteases. The requirement for hTCP for gp160 maturation was tested by creating genetically modified cell lines where the constitutive high levels of the transfected hTCP-specific antisense construct interfered with the expression of the hTCP gene, but not other SPC protease genes. The present examples demonstrate that HIV virions derived from the hTCP antisense-transfected cell lines are not infectious, by two independent infectivity assays. Although a role for PC8 in gp160 processing has not been excluded, the absence of a gp160 processing defect when cells are depleted of furin activity in LoVo cells, taken together with the data presented herein, strongly suggest that hTCP is solely responsible for gp160 cleavage.

It is important to point out that the cell line #4, which exhibits greatly reduced, yet detectable levels of hTCP expression, may influence gp160 processing activity due to decreased capacity for cleavage. To create a fusogenic pore structure, the viral glycoproteins apparently must function coordinately as a unit of 9–12 monomeric subunits to be active for infectivity (White et al., 1995, *Cold Spring Harbor Symposia on Quantitative Biology* 60:581–588). Therefore, reducing the efficiency of gp160 precursor processing, perhaps even 5-fold from 5–15%, may be sufficient to eliminate the probability of generating any functional units for viral infectivity, while retaining the ability to process cellular precursors for function. Without being bound by theory, the present inventors believe that the individual SPC proteases inhabit different branches of the secretory pathways within cells. Hence, the depletion or inactivation of one SPC protease member will not be compensated by the activity of another member, due to their presumably distinct intracellular localization. These features underscore the value and need to analyze the properties of hTCP as an anti-viral target for therapeutic intervention.

Example 10

This Example demonstrates the applicability of antisense technology to inhibition of the expression of a dibasic amino acid processing endoprotease gene.

Figure 4:
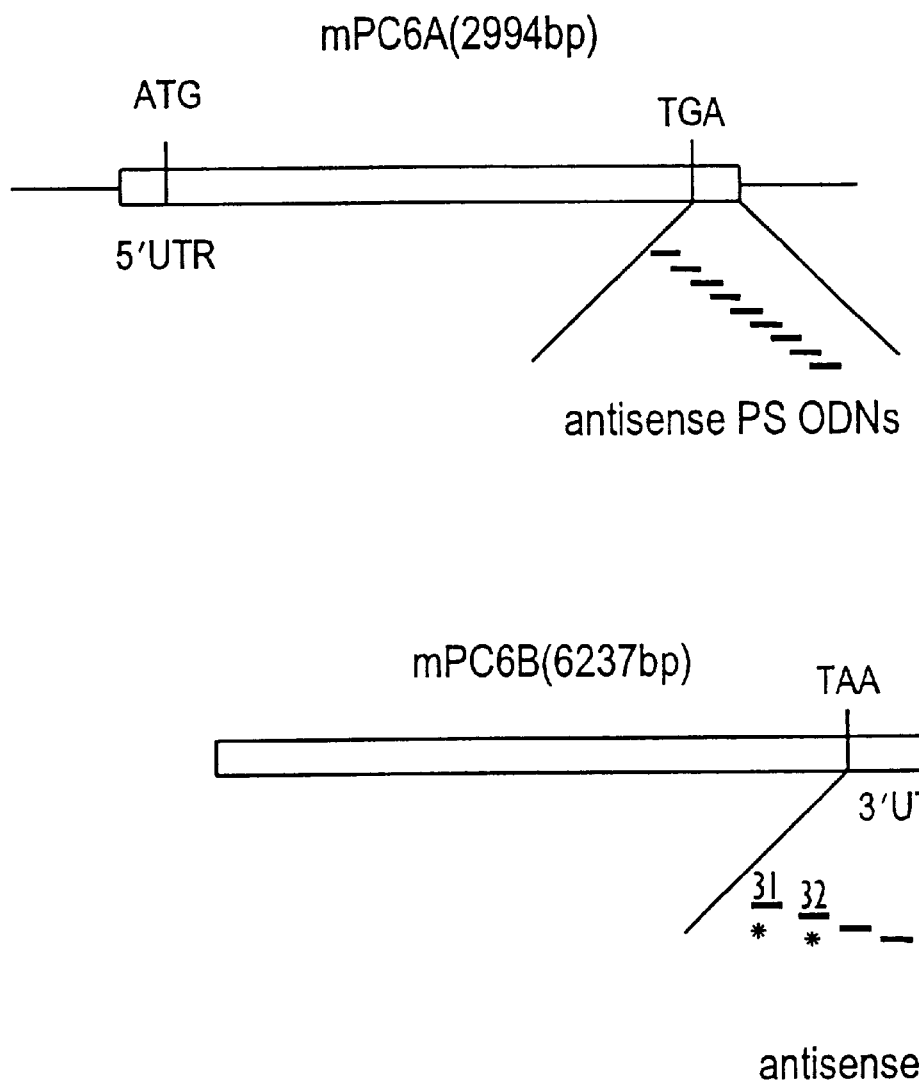
FIG. 4 is a schematic drawing illustrating an antisense oligonucleotide strategy for inhibiting the expression of a dibasic amino acid processing endoprotease gene.

In this experiment, oligonucleotides were designed to span portions of the 3' untranslated region (3' UTR) of the mouse PC6A and the PC6B isoforms. FIG. 4 is a schematic representation of the approximate positions of the series of oligonucleotides in PC6A and PC6B 3' UTRs. The oligonucleotides were modified with phosphorothioate (ODN), a chemical modification which adds thiol groups to the phosphates of the sugar-phosphate backbone of the oligonucleotide, using standard protocols, such as that described in Crooke et al., 1996, *J. of Pharm. and Exp. Therapeutics* 277:923–937, which is incorporated herein by reference in its entirety. The oligonucleotides were then transfected into AtT20 pituitary cells. To determine whether any of the oligonucleotides inhibited expression of the PC6B isoform, RNA was isolated from the transfected AtT20 cells, and reverse transcriptase polymerase chain reaction RT-PCR was performed using primers designed to amplify the PC6B isoform. Two of the oligonucleotides, denoted in FIG. 4 as 31 and 32, and represented herein as SEQ ID NO:29 and SEQ ID NO:30, respectively, completely inhibited the expression of the PC6B gene in AtT20 cells. A third oligonucleotide, denoted in FIG. 4 as 35 and represented herein as SEQ ID NO:31, reduced the expression of the PC6B gene as compared to the positive control. Therefore, antisense oligonucleotides directed against the regulatory region of a dibasic amino acid processing endoprotease gene, such as the untranslated region (UTR) of an RNA molecule encoding the dibasic amino acid processing endoprotease, can be used to completely or partially knock out the expression of the dibasic amino acid processing endoprotease gene by a cell. This experiment provides evidence that such an antisense strategy is technically feasible. Indeed, such an oligonucleotide antisense approach is desirable for use in vivo, since oligonucleotides can be easily chemically modified as described to enhance the stability of the nucleic acid molecule. Given the identification and sequence of the novel human T cell protease gene of the present invention presented herein, and the discovery by the present inventors that hTCP is likely to be the sole endogenous HIV gp120 dibasic amino acid processing endoprotease, it is within the scope of the present invention, to design and select oligonucleotides corresponding to portions of the 3' UTR of the nhTCP gene which effectively inhibit the expression of hTCP by the cell, and to use such oligonucleotides in a therapeutic composition to reduce the infectivity of an infectious agent, such as HIV.

SEQUENCE LISTING

The following Sequence Listing is submitted pursuant to 37 CFR §1.821. A copy in computer readable form is also submitted herewith.

Applicants assert pursuant to 37 CFR §1.821(f) that the content of the paper and computer readable copies of SEQ ID NO:1 through SEQ ID NO:31 submitted herewith are the same.

```
                              SEQUENCE LISTING (1) GENERAL INFORMATION:

(iii) NUMBER OF SEQUENCES: 31

(2) INFORMATION FOR SEQ ID NO:1:

(i) SEQUENCE CHARACTERISTICS:
          (A) LENGTH: 483 base pairs
          (B) TYPE: nucleic acid
          (C) STRANDEDNESS: single
          (D) TOPOLOGY: linear (ii) MOLECULE TYPE: cDNA (ix) FEATURE:
          (A) NAME/KEY: CDS
          (B) LOCATION: 1..483

(xi) SEQUENCE DESCRIPTION: SEQ ID NO:1:

TGT GGA GTA GGA GTG GCT TAC AAC GCC AAG ATC GGA GGA GTG CGA ATG       48
Cys Gly Val Gly Val Ala Tyr Asn Ala Lys Ile Gly Gly Val Arg Met
  1               5                  10                  15

CTG GAC GGA GAT GTC ACG GAC ATG GTT GAA GCA AAA TCA GTT AGC TTC       96
Leu Asp Gly Asp Val Thr Asp Met Val Glu Ala Lys Ser Val Ser Phe
             20                  25                  30

AAC CCC CAG CAC GTG CAC ATT ACA GCG GCC AGC TGG GGC CCG GAT GAT      144
Asn Pro Gln His Val His Ile Thr Ala Ala Ser Trp Gly Pro Asp Asp
         35                  40                  45

GAT GGC AAG ACT GTG GAC GGA CCA GCC CCC CTC ACC CGG CAA GCC TTT      192
Asp Gly Lys Thr Val Asp Gly Pro Ala Pro Leu Thr Arg Gln Ala Phe
     50                  55                  60

GAA AAC GGC GTT AGA ATG GGG CGG AGA GGC CTC GGC TCT GTT GTT TGG      240
Glu Asn Gly Val Arg Met Gly Arg Arg Gly Leu Gly Ser Val Val Trp
 65                  70                  75                  80

GCA TCT GGA AAT GGT GGA AGG AGC AAA GAC CAC TGC TCC TGT GAT GGC      288
Ala Ser Gly Asn Gly Gly Arg Ser Lys Asp His Cys Ser Cys Asp Gly
                 85                  90                  95

TAC ACC AAC AGC ATC TAC ACC ATC TCC ATC AGC AGC ACT GCA GAA AGC      336
Tyr Thr Asn Ser Ile Tyr Thr Ile Ser Ile Ser Ser Thr Ala Glu Ser
            100                 105                 110

GGA AAG GAA CCT TGG TAC CTG GAA GAG TGT TCA TCC ACG CTG GCC ACA      384
Gly Lys Glu Pro Trp Tyr Leu Glu Glu Cys Ser Ser Thr Leu Ala Thr
        115                 120                 125

ACC TAC AGC AGC GGG GAG TCC TAC GAT AAG AAA ATC ATC ACT ACA GAT      432
Thr Tyr Ser Ser Gly Glu Ser Tyr Asp Lys Lys Ile Ile Thr Thr Asp
    130                 135                 140
```

```
CTG AGG CAG CGT TGC ACG GAC AAC CAC TCA GGC ACC TCA GCC TCT GCT      480
Leu Arg Gln Arg Cys Thr Asp Asn His Ser Gly Thr Ser Ala Ser Ala
145                 150                 155                 160

CCC                                                                  483
Pro
```

(2) INFORMATION FOR SEQ ID NO:2:

(i) SEQUENCE CHARACTERISTICS:
        (A) LENGTH: 161 amino acids
        (B) TYPE: amino acid
        (D) TOPOLOGY: linear (ii) MOLECULE TYPE: protein (xi) SEQUENCE DESCRIPTION: SEQ ID NO:2:

```
Cys Gly Val Gly Val Ala Tyr Asn Ala Lys Ile Gly Val Arg Met
1               5                   10                  15

Leu Asp Gly Asp Val Thr Asp Met Val Glu Ala Lys Ser Val Ser Phe
            20                  25                  30

Asn Pro Gln His Val His Ile Thr Ala Ala Ser Trp Gly Pro Asp Asp
            35                  40                  45

Asp Gly Lys Thr Val Asp Gly Pro Ala Pro Leu Thr Arg Gln Ala Phe
        50                  55                  60

Glu Asn Gly Val Arg Met Gly Arg Arg Gly Leu Gly Ser Val Val Trp
65                  70                  75                  80

Ala Ser Gly Asn Gly Gly Arg Ser Lys Asp His Cys Ser Cys Asp Gly
                85                  90                  95

Tyr Thr Asn Ser Ile Tyr Thr Ile Ser Ile Ser Ser Thr Ala Glu Ser
                100                 105                 110

Gly Lys Glu Pro Trp Tyr Leu Glu Glu Cys Ser Ser Thr Leu Ala Thr
            115                 120                 125

Thr Tyr Ser Ser Gly Glu Ser Tyr Asp Lys Lys Ile Ile Thr Thr Asp
        130                 135                 140

Leu Arg Gln Arg Cys Thr Asp Asn His Ser Gly Thr Ser Ala Ser Ala
145                 150                 155                 160

Pro
```

(2) INFORMATION FOR SEQ ID NO:3:

(i) SEQUENCE CHARACTERISTICS:
        (A) LENGTH: 111 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..111

(xi) SEQUENCE DESCRIPTION: SEQ ID NO:3:

```
GAC AAT ACA CAT CCC TGC CAG TCT GAC ATG AAT ATC GAA GGA GCC TGG      48
Asp Asn Thr His Pro Cys Gln Ser Asp Met Asn Ile Glu Gly Ala Trp
1               5                   10                  15

AAG AGA GGC TAC ACG GGA AAG AAC ATT GTG GTC ACT ATC CTG GAT GAC      96
Lys Arg Gly Tyr Thr Gly Lys Asn Ile Val Val Thr Ile Leu Asp Asp
                20                  25                  30

GGA ATT GAG AGA ACC                                                  111
Gly Ile Glu Arg Thr
            35
```

(2) INFORMATION FOR SEQ ID NO:4:

(i) SEQUENCE CHARACTERISTICS:
        (A) LENGTH: 37 amino acids
        (B) TYPE: amino acid
        (D) TOPOLOGY: linear (ii) MOLECULE TYPE: protein (xi) SEQUENCE DESCRIPTION: SEQ ID NO:4:

```
Asp Asn Thr His Pro Cys Gln Ser Asp Met Asn Ile Glu Gly Ala Trp
 1               5                  10                  15

Lys Arg Gly Tyr Thr Gly Lys Asn Ile Val Val Thr Ile Leu Asp Asp
             20                  25                  30

Gly Ile Glu Arg Thr
         35
```

(2) INFORMATION FOR SEQ ID NO:5:

(i) SEQUENCE CHARACTERISTICS:
        (A) LENGTH: 4 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:5:

```
Xaa Xaa Xaa Xaa
 1
```

(2) INFORMATION FOR SEQ ID NO:6:

(i) SEQUENCE CHARACTERISTICS:
        (A) LENGTH: 4 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:6:

```
Arg Glu Lys Arg
 1
```

(2) INFORMATION FOR SEQ ID NO:7:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

TCCCGTCGAC HYCCCABSWR TGRRYDGWCA TGAA                       34

(2) INFORMATION FOR SEQ ID NO:8:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

```
TGTCGGATCC TGYGGNGTHG GHGTDGCHTA YAAYKCC                              37
```

(2) INFORMATION FOR SEQ ID NO:9:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

```
TCCCGTCGAC SGGDGCWGMD GCHGAKGTSC CHGWRTG                              37
```

(2) INFORMATION FOR SEQ ID NO:10:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

```
CCAAGYATGT GGTAYATGCA YTGYAGY                                         27
```

(2) INFORMATION FOR SEQ ID NO:11:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

```
GGCTGCTCAG CCTTGGAATG TACATGTTTT                                      30
```

(2) INFORMATION FOR SEQ ID NO:12:

(i) SEQUENCE CHARACTERISTICS:
        (A) LENGTH: 918 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..918

(xi) SEQUENCE DESCRIPTION: SEQ ID NO:12:

```
TAT ATG CAC TGT AGC GAC AAT ACA CAT CCC TGC CAG TCT GAC ATG AAT       48
Tyr Met His Cys Ser Asp Asn Thr His Pro Cys Gln Ser Asp Met Asn
 1               5                  10                  15

ATC GAA GGA GCC TGG AAG AGA GGC TAC ACG GGA AAG AAC ATT GTG GTC       96
Ile Glu Gly Ala Trp Lys Arg Gly Tyr Thr Gly Lys Asn Ile Val Val
             20                  25                  30

ACT ATC CTG GAT GAC GGA ATT GAG AGA ACC CAT CCA GAT CTG ATG CAA      144
Thr Ile Leu Asp Asp Gly Ile Glu Arg Thr His Pro Asp Leu Met Gln
         35                  40                  45

AAC TAC GAT GCT CTG GCA AGT TGC GAC GTG AAT GGG AAT GAC TTG GAC      192
Asn Tyr Asp Ala Leu Ala Ser Cys Asp Val Asn Gly Asn Asp Leu Asp
     50                  55                  60
```

```
CCA ATG CCT CGT TAT GAT GCA AGC AAC GAG AAC AAG CAT GGG ACT CGC          240
Pro Met Pro Arg Tyr Asp Ala Ser Asn Glu Asn Lys His Gly Thr Arg
 65                  70                  75                  80

TGT GCT GGA GAA GTG GCA GCC GCT GCA AAC AAT TCG CAC TGC ACA GTC          288
Cys Ala Gly Glu Val Ala Ala Ala Ala Asn Asn Ser His Cys Thr Val
                 85                  90                  95

GGA ATT GCT TTC AAC GCC AAG ATC GGA GGA GTG CGA ATG CTG GAC GGA          336
Gly Ile Ala Phe Asn Ala Lys Ile Gly Gly Val Arg Met Leu Asp Gly
            100                 105                 110

GAT GTC ACG GAC ATG GTT GAA GCA AAA TCA GTT AGC TTC AAC CCC CAG          384
Asp Val Thr Asp Met Val Glu Ala Lys Ser Val Ser Phe Asn Pro Gln
        115                 120                 125

CAC GTG CAC ATT TAC AGC GCC AGC TGG GGC CCG GAT GAT GAT GGC AAG          432
His Val His Ile Tyr Ser Ala Ser Trp Gly Pro Asp Asp Asp Gly Lys
    130                 135                 140

ACT GTG GAC GGA CCA GCC CCC CTC ACC CGG AAA GCC TTT GAA AAC GGC          480
Thr Val Asp Gly Pro Ala Pro Leu Thr Arg Lys Ala Phe Glu Asn Gly
145                 150                 155                 160

GTT AGA ATG GGG CGG AGA GGC CTC GGA TCT GTG TTT GTT TGG GCA TCT          528
Val Arg Met Gly Arg Arg Gly Leu Gly Ser Val Phe Val Trp Ala Ser
                165                 170                 175

GGA AAT GGT GGA AGG AGC AAA GAC CAC TGC TCC TGT GAT GGC TAC ACC          576
Gly Asn Gly Gly Arg Ser Lys Asp His Cys Ser Cys Asp Gly Tyr Thr
            180                 185                 190

AAC AGC ATC TAC ACC ATC TCC ATC AGC AGC ACT GCA GAA AGC GGA AAG          624
Asn Ser Ile Tyr Thr Ile Ser Ile Ser Ser Thr Ala Glu Ser Gly Lys
        195                 200                 205

AAA CCT TGG TAC CTG GAA GAG TGT TCA TCC ACG CTG GCC ACA ACC TAC          672
Lys Pro Trp Tyr Leu Glu Glu Cys Ser Ser Thr Leu Ala Thr Thr Tyr
    210                 215                 220

AGC AGC GGG GAG TCC TAC GAT AAG AAA ATC ATC ACT ACA GAT CTG AGG          720
Ser Ser Gly Glu Ser Tyr Asp Lys Lys Ile Ile Thr Thr Asp Leu Arg
225                 230                 235                 240

CAG CGT TGC ACG GAC AAC CAC ACT GGG ACG TCA GCC TCA GCC CCC ATG          768
Gln Arg Cys Thr Asp Asn His Thr Gly Thr Ser Ala Ser Ala Pro Met
                245                 250                 255

GCT GCA GGC ATC ATT GCG CTG GCC CTG GAA GCC AAT CCG TTT CTG ACC          816
Ala Ala Gly Ile Ile Ala Leu Ala Leu Glu Ala Asn Pro Phe Leu Thr
            260                 265                 270

TGG AGA GAC GTA CAG CAT GTT ATT GTC AGG ACT TCC CGT GCG GGA CAT          864
Trp Arg Asp Val Gln His Val Ile Val Arg Thr Ser Arg Ala Gly His
        275                 280                 285

TTG AAC GCT AAT GAC TGG AAA ACC AAT GCT GCT GGT TTT AAG GTG AGC          912
Leu Asn Ala Asn Asp Trp Lys Thr Asn Ala Ala Gly Phe Lys Val Ser
    290                 295                 300

CAT CTT                                                                   918
His Leu
305

(2) INFORMATION FOR SEQ ID NO:13:

(i) SEQUENCE CHARACTERISTICS:
        (A) LENGTH: 306 amino acids
        (B) TYPE: amino acid
        (D) TOPOLOGY: linear (ii) MOLECULE TYPE: protein (xi) SEQUENCE DESCRIPTION: SEQ ID NO:13:

Tyr Met His Cys Ser Asp Asn Thr His Pro Cys Gln Ser Asp Met Asn
 1               5                  10                  15
```

```
Ile Glu Gly Ala Trp Lys Arg Gly Tyr Thr Gly Lys Asn Ile Val
            20                  25                  30
Thr Ile Leu Asp Asp Gly Ile Glu Arg Thr His Pro Asp Leu Met Gln
                35                  40                  45
Asn Tyr Asp Ala Leu Ala Ser Cys Asp Val Asn Gly Asn Asp Leu Asp
 50                  55                  60
Pro Met Pro Arg Tyr Asp Ala Ser Asn Glu Asn Lys His Gly Thr Arg
 65                  70                  75                  80
Cys Ala Gly Glu Val Ala Ala Ala Asn Asn Ser His Cys Thr Val
                85                  90                  95
Gly Ile Ala Phe Asn Ala Lys Ile Gly Gly Val Arg Met Leu Asp Gly
                100                 105                 110
Asp Val Thr Asp Met Val Glu Ala Lys Ser Val Ser Phe Asn Pro Gln
                115                 120                 125
His Val His Ile Tyr Ser Ala Ser Trp Gly Pro Asp Asp Gly Lys
                130                 135                 140
Thr Val Asp Gly Pro Ala Pro Leu Thr Arg Lys Ala Phe Glu Asn Gly
145                 150                 155                 160
Val Arg Met Gly Arg Arg Gly Leu Gly Ser Val Phe Val Trp Ala Ser
                165                 170                 175
Gly Asn Gly Gly Arg Ser Lys Asp His Cys Ser Cys Asp Gly Tyr Thr
                180                 185                 190
Asn Ser Ile Tyr Thr Ile Ser Ile Ser Ser Thr Ala Glu Ser Gly Lys
                195                 200                 205
Lys Pro Trp Tyr Leu Glu Glu Cys Ser Ser Thr Leu Ala Thr Thr Tyr
                210                 215                 220
Ser Ser Gly Glu Ser Tyr Asp Lys Lys Ile Ile Thr Thr Asp Leu Arg
225                 230                 235                 240
Gln Arg Cys Thr Asp Asn His Thr Gly Thr Ser Ala Ser Ala Pro Met
                245                 250                 255
Ala Ala Gly Ile Ile Ala Leu Ala Leu Glu Ala Asn Pro Phe Leu Thr
                260                 265                 270
Trp Arg Asp Val Gln His Val Ile Val Arg Thr Ser Arg Ala Gly His
                275                 280                 285
Leu Asn Ala Asn Asp Trp Lys Thr Asn Ala Ala Gly Phe Lys Val Ser
                290                 295                 300
His Leu
305

(2) INFORMATION FOR SEQ ID NO:14:

(i) SEQUENCE CHARACTERISTICS:
        (A) LENGTH: 867 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..867

(xi) SEQUENCE DESCRIPTION: SEQ ID NO:14:

GAC TAT GGC ACA GAG GAT TAT GCA GGT CCC TGC GAC CCT GAG TGC AGT     48
Asp Tyr Gly Thr Glu Asp Tyr Ala Gly Pro Cys Asp Pro Glu Cys Ser
 1               5                  10                  15

GAG GTT GGC TGT GAC GGG CCA GGA CCA GAC CAC TGC AAT GAC TGT TTG     96
Glu Val Gly Cys Asp Gly Pro Gly Pro Asp His Cys Asn Asp Cys Leu
```

|    |    |    |    |    |    |    |    |    |    |    |    |    |    |    |    |     |
|----|----|----|----|----|----|----|----|----|----|----|----|----|----|----|----|-----|
|    |    |    | 20 |    |    |    |    | 25 |    |    |    |    | 30 |    |    |     |

```
CAC TAC TAC TAC AAG CTG AAA AAC AAT ACC AGG ATC TGT GTC TCC AGC     144
His Tyr Tyr Tyr Lys Leu Lys Asn Asn Thr Arg Ile Cys Val Ser Ser
             35                  40                  45

TGC CCC CCT GGC CAC TAC CAC GCC GAC AAG AAG CGC TGC AGG AAG TGT     192
Cys Pro Pro Gly His Tyr His Ala Asp Lys Lys Arg Cys Arg Lys Cys
     50                  55                  60

GCC CCC AAC TGT GAG TCC TGC TTT GGG AGC CAT GGT GAC CAA TGC ATG     240
Ala Pro Asn Cys Glu Ser Cys Phe Gly Ser His Gly Asp Gln Cys Met
 65                  70                  75                  80

TCC TGC AAA TAT GGA TAC TTT CTG AAT GAA GAA ACC AAC AGC TGT GTT     288
Ser Cys Lys Tyr Gly Tyr Phe Leu Asn Glu Glu Thr Asn Ser Cys Val
             85                  90                  95

ACT CAC TGC CCT GAT GGG TCA TAT CAG GAT ACC AAG AAA AAT CTT TGC     336
Thr His Cys Pro Asp Gly Ser Tyr Gln Asp Thr Lys Lys Asn Leu Cys
                100                 105                 110

CGG AAA TGC AGT GAA AAC TTC AAG ACA TGT ACT GAA TTC CAT ATC TGT     384
Arg Lys Cys Ser Glu Asn Phe Lys Thr Cys Thr Glu Phe His Ile Cys
            115                 120                 125

ACA GAA TGT AGG GAT GGG TTA AGC CTT CAG GGA TCC CGG TGC TCT GTC     432
Thr Glu Cys Arg Asp Gly Leu Ser Leu Gln Gly Ser Arg Cys Ser Val
130                 135                 140

TCC TGT GAA GAT GGA CGG TAT TTC ATC GGC CAG GAC TGC CAG CCC TGC     480
Ser Cys Glu Asp Gly Arg Tyr Phe Ile Gly Gln Asp Cys Gln Pro Cys
145                 150                 155                 160

CAC CGC TTC TTC GCC ACT TGT GCT GGG GCA GGA GCT GAT GGG TGC ATT     528
His Arg Phe Phe Ala Thr Cys Ala Gly Ala Gly Ala Asp Gly Cys Ile
                165                 170                 175

AAC TGC ACA GAG GGC TAC TTC ATG GAG GAT GGG AGA TGC GTG CAG ATC     576
Asn Cys Thr Glu Gly Tyr Phe Met Glu Asp Gly Arg Cys Val Gln Ile
            180                 185                 190

TGT AGT ATC AGC TAT TAC TTT GAC CAC TCT TCA GAG AAT GGA TAC AAA     624
Cys Ser Ile Ser Tyr Tyr Phe Asp His Ser Ser Glu Asn Gly Tyr Lys
        195                 200                 205

TCC TGC AAA AAA TGT GAT ATC AGT TGT TTG ACG TGC AAT GGC CCA GGA     672
Ser Cys Lys Lys Cys Asp Ile Ser Cys Leu Thr Cys Asn Gly Pro Gly
210                 215                 220

TTC AAG AAC TGT ACA AGC TGC CCT AGT GGG TAT CTC TTA GAC TTA GGA     720
Phe Lys Asn Cys Thr Ser Cys Pro Ser Gly Tyr Leu Leu Asp Leu Gly
225                 230                 235                 240

ATG TGT CAA ATG GGA GCC ATT TGC AAG GAT GCA ACG GAA GAG TCC TGG     768
Met Cys Gln Met Gly Ala Ile Cys Lys Asp Ala Thr Glu Glu Ser Trp
                245                 250                 255

GCG GAA GGA GGC TTC TGT ATG CTT GTG AAA AAG AAC AAT CTG TGC CAA     816
Ala Glu Gly Gly Phe Cys Met Leu Val Lys Lys Asn Asn Leu Cys Gln
            260                 265                 270

CGG AAG GTT CTT CAA CAA CTT TGC TGC AAA ACA TGT ACA TTC CAA GGC     864
Arg Lys Val Leu Gln Gln Leu Cys Cys Lys Thr Cys Thr Phe Gln Gly
        275                 280                 285

TGA                                                                 867
 *
```

(2) INFORMATION FOR SEQ ID NO:15:

(i) SEQUENCE CHARACTERISTICS:
        (A) LENGTH: 288 amino acids
        (B) TYPE: amino acid
        (D) TOPOLOGY: linear (ii) MOLECULE TYPE: protein (xi) SEQUENCE DESCRIPTION: SEQ ID NO:15:

| | | | | | | | | | | | |
|---|---|---|---|---|---|---|---|---|---|---|---|
|Asp|Tyr|Gly|Thr|Glu|Asp|Tyr|Ala|Gly|Pro|Cys|Asp Pro Glu Cys Ser|
|1| | | |5| | | |10| | |15|
|Glu|Val|Gly|Cys|Asp|Gly|Pro|Gly|Pro|Asp|His|Cys Asn Asp Cys Leu|
| | | |20| | | | |25| | |30|
|His|Tyr|Tyr|Lys|Leu|Lys|Asn|Asn|Thr|Arg|Ile|Cys Val Ser Ser|
| | |35| | | | |40| | | |45|
|Cys|Pro|Pro|Gly|His|Tyr|His|Ala|Asp|Lys|Lys|Arg Cys Arg Lys Cys|
| |50| | | | |55| | | |60| |
|Ala|Pro|Asn|Cys|Glu|Ser|Cys|Phe|Gly|Ser|His|Gly Asp Gln Cys Met|
|65| | | | |70| | | |75| | 80|
|Ser|Cys|Lys|Tyr|Gly|Tyr|Phe|Leu|Asn|Glu|Glu|Thr Asn Ser Cys Val|
| | | | |85| | | |90| | | 95|
|Thr|His|Cys|Pro|Asp|Gly|Ser|Tyr|Gln|Asp|Thr|Lys Lys Asn Leu Cys|
| | | |100| | | |105| | | |110|
|Arg|Lys|Cys|Ser|Glu|Asn|Phe|Lys|Thr|Cys|Thr|Glu Phe His Ile Cys|
| | |115| | | | |120| | | |125|
|Thr|Glu|Cys|Arg|Asp|Gly|Leu|Ser|Leu|Gln|Gly|Ser Arg Cys Ser Val|
| |130| | | | |135| | | |140| |
|Ser|Cys|Glu|Asp|Gly|Arg|Tyr|Phe|Ile|Gly|Gln|Asp Cys Gln Pro Cys|
|145| | | | |150| | | |155| | 160|
|His|Arg|Phe|Phe|Ala|Thr|Cys|Ala|Gly|Ala|Gly|Ala Asp Gly Cys Ile|
| | | | |165| | | |170| | |175|
|Asn|Cys|Thr|Glu|Gly|Tyr|Phe|Met|Glu|Asp|Gly|Arg Cys Val Gln Ile|
| | | |180| | | |185| | | |190|
|Cys|Ser|Ile|Ser|Tyr|Tyr|Phe|Asp|His|Ser|Ser|Glu Asn Gly Tyr Lys|
| | |195| | | |200| | | |205| |
|Ser|Cys|Lys|Lys|Cys|Asp|Ile|Ser|Cys|Leu|Thr|Cys Asn Gly Pro Gly|
|210| | | |215| | | |220| | | |
|Phe|Lys|Asn|Cys|Thr|Ser|Cys|Pro|Ser|Gly|Tyr|Leu Leu Asp Leu Gly|
|225| | | |230| | | |235| | | 240|
|Met|Cys|Gln|Met|Gly|Ala|Ile|Cys|Lys|Asp|Ala|Thr Glu Glu Ser Trp|
| | | |245| | | |250| | | |255|
|Ala|Glu|Gly|Gly|Phe|Cys|Met|Leu|Val|Lys|Lys|Asn Asn Leu Cys Gln|
| | |260| | | | |265| | | |270|
|Arg|Lys|Val|Leu|Gln|Gln|Leu|Cys|Cys|Lys|Thr|Cys Thr Phe Gln Gly|
| |275| | | | |280| | | |285| |

(2) INFORMATION FOR SEQ ID NO:16:

(i) SEQUENCE CHARACTERISTICS:
        (A) LENGTH: 444 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: 5'UTR
        (B) LOCATION: 1..444

(xi) SEQUENCE DESCRIPTION: SEQ ID NO:16:

```
AGCGTCGGGA CCATGGATTG GGATTGGGGG AACCGCTGCA GCCGCCCGGG ACGGCGGGAC    60

CTGCTGTGCG TGCTGGCACT GCTCGCCGGC TGTCTGCTCC CGGTATGCCG ACGCGCGTC    120

TACACCAACC ACTGGGCAGT GAAGATCGCC GGCGGCTTCG CGGAGGCAGA TCGCATAGCC   180

AGCAAGTACG GATTCATCAA CGTAGGACAG ATCGGTGCAC TGAAGGACTA CTATCACTTC   240
```

5,981,259

61

-continued

| TACCATAGTA GGACCATTAA AAGGTCTGTT CTCTCGAGCA GAGGAACCCA CAGTTTCATT | 300 |
| TCAATGGAAC CAAAGGTGGA GTGGATCCAA CAGCAAGTGG TGAAAAAAG AACCAAGAGG | 360 |
| GATTATGACC TCAGCCATGC CCAGTCAACC TACTTCAATG ATCCCAAGTG GCCAAGTATG | 420 |
| TGGTACATGC ACTGCAGTGA CAAT | 444 |

(2) INFORMATION FOR SEQ ID NO:17:

(i) SEQUENCE CHARACTERISTICS:
        (A) LENGTH: 2766 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 13..2757

(xi) SEQUENCE DESCRIPTION: SEQ ID NO:17:

```
AGCGTCGGGA CC ATG GAT TGG GAT TGG GGG AAC CGC TGC AGC CGC CCG              48
              Met Asp Trp Asp Trp Gly Asn Arg Cys Ser Arg Pro
              1               5                   10

GGA CGG CGG GAC CTG CTG TGC GTG CTG GCA CTG CTC GCC GGC TGT CTG             96
Gly Arg Arg Asp Leu Leu Cys Val Leu Ala Leu Leu Ala Gly Cys Leu
        15                  20                  25

CTC CCG GTA TGC CGG ACG CGC GTC TAC ACC AAC CAC TGG GCA GTG AAG            144
Leu Pro Val Cys Arg Thr Arg Val Tyr Thr Asn His Trp Ala Val Lys
    30                  35                  40

ATC GCC GGC GGC TTC GCG GAG GCA GAT CGC ATA GCC AGC AAG TAC GGA            192
Ile Ala Gly Gly Phe Ala Glu Ala Asp Arg Ile Ala Ser Lys Tyr Gly
45                  50                  55                  60

TTC ATC AAC GTA GGA CAG ATC GGT GCA CTG AAG GAC TAC TAT CAC TTC            240
Phe Ile Asn Val Gly Gln Ile Gly Ala Leu Lys Asp Tyr Tyr His Phe
                65                  70                  75

TAC CAT AGT AGG ACC ATT AAA AGG TCT GTT CTC TCG AGC AGA GGA ACC            288
Tyr His Ser Arg Thr Ile Lys Arg Ser Val Leu Ser Ser Arg Gly Thr
            80                  85                  90

CAC AGT TTC ATT TCA ATG GAA CCA AAG GTG GAG TGG ATC CAA CAG CAA            336
His Ser Phe Ile Ser Met Glu Pro Lys Val Glu Trp Ile Gln Gln Gln
        95                  100                 105

GTG GTG AAA AAA AGA ACC AAG AGG GAT TAT GAC CTC AGC CAT GCC CAG            384
Val Val Lys Lys Arg Thr Lys Arg Asp Tyr Asp Leu Ser His Ala Gln
    110                 115                 120

TCA ACC TAC TTC AAT GAT CCC AAG TGG CCA AGT ATG TGG TAC ATG CAC            432
Ser Thr Tyr Phe Asn Asp Pro Lys Trp Pro Ser Met Trp Tyr Met His
125                 130                 135                 140

TGC AGT GAC AAT ACA CAT CCC TGC CAG TCT GAC ATG AAT ATC GAA GGA            480
Cys Ser Asp Asn Thr His Pro Cys Gln Ser Asp Met Asn Ile Glu Gly
                145                 150                 155

GCC TGG AAG AGA GGC TAC ACG GGA AAG AAC ATT GTG GTC ACT ATC CTG            528
Ala Trp Lys Arg Gly Tyr Thr Gly Lys Asn Ile Val Val Thr Ile Leu
            160                 165                 170

GAT GAC GGA ATT GAG AGA ACC CAT CCA GAT CTG ATG CAA AAC TAC GAT            576
Asp Asp Gly Ile Glu Arg Thr His Pro Asp Leu Met Gln Asn Tyr Asp
        175                 180                 185

GCT CTG GCA AGT TGC GAC GTG AAT GGG AAT GAC TTG GAC CCA ATG CCT            624
Ala Leu Ala Ser Cys Asp Val Asn Gly Asn Asp Leu Asp Pro Met Pro
    190                 195                 200

CGT TAT GAT GCA AGC AAC GAG AAC AAG CAT GGG ACT CGC TGT GCT GGA            672
Arg Tyr Asp Ala Ser Asn Glu Asn Lys His Gly Thr Arg Cys Ala Gly
205                 210                 215                 220
```

```
GAA GTG GCA GCC GCT GCA AAC AAT TCG CAC TGC ACA GTC GGA ATT GCT      720
Glu Val Ala Ala Ala Ala Asn Asn Ser His Cys Thr Val Gly Ile Ala
                225                 230                 235

TTC AAC GCC AAG ATC GGA GGA GTG CGA ATG CTG GAC GGA GAT GTC ACG      768
Phe Asn Ala Lys Ile Gly Gly Val Arg Met Leu Asp Gly Asp Val Thr
                240                 245                 250

GAC ATG GTT GAA GCA AAA TCA GTT AGC TTC AAC CCC CAG CAC GTG CAC      816
Asp Met Val Glu Ala Lys Ser Val Ser Phe Asn Pro Gln His Val His
                255                 260                 265

ATT TAC AGC GCC AGC TGG GGC CCG GAT GAT GAT GGC AAG ACT GTG GAC      864
Ile Tyr Ser Ala Ser Trp Gly Pro Asp Asp Asp Gly Lys Thr Val Asp
                270                 275                 280

GGA CCA GCC CCC CTC ACC CGG CAA GCC TTT GAA AAC GGC GTT AGA ATG      912
Gly Pro Ala Pro Leu Thr Arg Gln Ala Phe Glu Asn Gly Val Arg Met
285                 290                 295                 300

GGG CGG AGA GGC CTC GGC TCT GTG TTT GTT TGG GCA TCT GGA AAT GGT      960
Gly Arg Arg Gly Leu Gly Ser Val Phe Val Trp Ala Ser Gly Asn Gly
                305                 310                 315

GGA AGG AGC AAA GAC CAC TGC TCC TGT GAT GGC TAC ACC AAC AGC ATC     1008
Gly Arg Ser Lys Asp His Cys Ser Cys Asp Gly Tyr Thr Asn Ser Ile
                320                 325                 330

TAC ACC ATC TCC ATC AGC AGC ACT GCA GAA AGC GGA AAG AAA CCT TGG     1056
Tyr Thr Ile Ser Ile Ser Ser Thr Ala Glu Ser Gly Lys Lys Pro Trp
                335                 340                 345

TAC CTG GAA GAG TGT TCA TCC ACG CTG GCC ACA ACC TAC AGC AGC GGG     1104
Tyr Leu Glu Glu Cys Ser Ser Thr Leu Ala Thr Thr Tyr Ser Ser Gly
350                 355                 360

GAG TCC TAC GAT AAG AAA ATC ATC ACT ACA GAT CTG AGG CAG CGT TGC     1152
Glu Ser Tyr Asp Lys Lys Ile Ile Thr Thr Asp Leu Arg Gln Arg Cys
365                 370                 375                 380

ACG GAC AAC CAC ACT GGG ACG TCA GCC TCA GCC CCC ATG GCT GCA GGC     1200
Thr Asp Asn His Thr Gly Thr Ser Ala Ser Ala Pro Met Ala Ala Gly
                385                 390                 395

ATC ATT GCG CTG GCC CTG GAA GCC AAT CCG TTT CTG ACC TGG AGA GAC     1248
Ile Ile Ala Leu Ala Leu Glu Ala Asn Pro Phe Leu Thr Trp Arg Asp
                400                 405                 410

GTA CAG CAT GTT ATT GTC AGG ACT TCC CGT GCG GGA CAT TTG AAC GCT     1296
Val Gln His Val Ile Val Arg Thr Ser Arg Ala Gly His Leu Asn Ala
                415                 420                 425

AAT GAC TGG AAA ACC AAT GCT GCT GGT TTT AAG GTG AGC CAT CTT TAT     1344
Asn Asp Trp Lys Thr Asn Ala Ala Gly Phe Lys Val Ser His Leu Tyr
                430                 435                 440

GGA TTT GGA CTG ATG GAC GCA GAA GCC ATG GTG ATG GAG GCA GAG AAG     1392
Gly Phe Gly Leu Met Asp Ala Glu Ala Met Val Met Glu Ala Glu Lys
445                 450                 455                 460

TGG ACC ACC GTT CCC CGG CAG CAC GTG TGT GTG GAG AGC ACA GAC CGA     1440
Trp Thr Thr Val Pro Arg Gln His Val Cys Val Glu Ser Thr Asp Arg
                465                 470                 475

CAA ATC AAG ACA ATC CGC CCT AAC AGT GCA GTG CGC TCC ATC TAC AAA     1488
Gln Ile Lys Thr Ile Arg Pro Asn Ser Ala Val Arg Ser Ile Tyr Lys
                480                 485                 490

GCT TCA GGC TGC TCG GAT AAC CCC AAC CGC CAT GTC AAC TAC CTG GAG     1536
Ala Ser Gly Cys Ser Asp Asn Pro Asn Arg His Val Asn Tyr Leu Glu
                495                 500                 505

CAC GTC GTT GTG CGC ATC ACC ATC ACC CAC CCC AGG AGA GGA GAC CTG     1584
His Val Val Val Arg Ile Thr Ile Thr His Pro Arg Arg Gly Asp Leu
                510                 515                 520

GCC ATC TAC CTG ACC TCG CCC TCT GGA ACT AGG TCT CAG CTT TTG GCC     1632
Ala Ile Tyr Leu Thr Ser Pro Ser Gly Thr Arg Ser Gln Leu Leu Ala
525                 530                 535                 540
```

```
AAC AGG CTA TTT GAT CAC TCC ATG GAA GGA TTC AAA AAC TGG GAG TTC    1680
Asn Arg Leu Phe Asp His Ser Met Glu Gly Phe Lys Asn Trp Glu Phe
            545                 550                 555

ATG ACC ATT CAT TGC TGG GGA GAA AGA GCT GCT GGT GAC TGG GTC CTT    1728
Met Thr Ile His Cys Trp Gly Glu Arg Ala Ala Gly Asp Trp Val Leu
            560                 565                 570

GAA GTT TAT GAT ACT CCC TCT CAG CTA AGG AAC TTT AAG ACT CCA GGT    1776
Glu Val Tyr Asp Thr Pro Ser Gln Leu Arg Asn Phe Lys Thr Pro Gly
            575                 580                 585

AAA TTG AAA GAA TGG TCT TTG GTC CTC TAC GGC ACC TCC GTG CGG CCA    1824
Lys Leu Lys Glu Trp Ser Leu Val Leu Tyr Gly Thr Ser Val Arg Pro
            590                 595                 600

TAT TCA CCA ACC AAT GAA TTT CCG AAA GTG GAA CGG TTC CGC TAT AGC    1872
Tyr Ser Pro Thr Asn Glu Phe Pro Lys Val Glu Arg Phe Arg Tyr Ser
605                 610                 615                 620

CGA GTT GAA GAC CCC ACA GAC GAC TAT GGC ACA GAG GAT TAT GCA GGT    1920
Arg Val Glu Asp Pro Thr Asp Asp Tyr Gly Thr Glu Asp Tyr Ala Gly
                625                 630                 635

CCC TGC GAC CCT GAG TGC AGT GAG GTT GGC TGT GAC GGG CCA GGA CCA    1968
Pro Cys Asp Pro Glu Cys Ser Glu Val Gly Cys Asp Gly Pro Gly Pro
            640                 645                 650

GAC CAC TGC AAT GAC TGT TTG CAC TAC TAC TAC AAG CTG AAA AAC AAT    2016
Asp His Cys Asn Asp Cys Leu His Tyr Tyr Tyr Lys Leu Lys Asn Asn
            655                 660                 665

ACC AGG ATC TGT GTC TCC AGC TGC CCC CCT GGC CAC TAC CAC GCC GAC    2064
Thr Arg Ile Cys Val Ser Ser Cys Pro Pro Gly His Tyr His Ala Asp
            670                 675                 680

AAG AAG CGC TGC AGG AAG TGT GCC CCC AAC TGT GAG TCC TGC TTT GGG    2112
Lys Lys Arg Cys Arg Lys Cys Ala Pro Asn Cys Glu Ser Cys Phe Gly
685                 690                 695                 700

AGC CAT GGT GAC CAA TGC ATG TCC TGC AAA TAT GGA TAC TTT CTG AAT    2160
Ser His Gly Asp Gln Cys Met Ser Cys Lys Tyr Gly Tyr Phe Leu Asn
                705                 710                 715

GAA GAA ACC AAC AGC TGT GTT ACT CAC TGC CCT GAT GGG TCA TAT CAG    2208
Glu Glu Thr Asn Ser Cys Val Thr His Cys Pro Asp Gly Ser Tyr Gln
            720                 725                 730

GAT ACC AAG AAA AAT CTT TGC CGG AAA TGC AGT GAA AAC TGC AAG ACA    2256
Asp Thr Lys Lys Asn Leu Cys Arg Lys Cys Ser Glu Asn Cys Lys Thr
            735                 740                 745

TGT ACT GAA TTC CAT AAC TGT ACA GAA TGT AGG GAT GGG TTA AGC CTG    2304
Cys Thr Glu Phe His Asn Cys Thr Glu Cys Arg Asp Gly Leu Ser Leu
            750                 755                 760

CAG GGA TCC CGG TGC TCT GTC TCC TGT GAA GAT GGA CGG TAT TTC AAC    2352
Gln Gly Ser Arg Cys Ser Val Ser Cys Glu Asp Gly Arg Tyr Phe Asn
765                 770                 775                 780

GGC CAG GAC TGC CAG CCC TGC CAC CGC TTC TGT GCC ACT TGT GCT GGG    2400
Gly Gln Asp Cys Gln Pro Cys His Arg Phe Cys Ala Thr Cys Ala Gly
                785                 790                 795

GCA GGA GCT GAT GGG TGC ATT AAC TGC ACA GAG GGC TAC TTC ATG GAG    2448
Ala Gly Ala Asp Gly Cys Ile Asn Cys Thr Glu Gly Tyr Phe Met Glu
            800                 805                 810

GAT GGG AGA TGC GTG CAG AGC TGT AGT ATC AGC TAT TAC TTT GAC CAC    2496
Asp Gly Arg Cys Val Gln Ser Cys Ser Ile Ser Tyr Tyr Phe Asp His
            815                 820                 825

TCT TCA GAG AAT GGA TAC AAA TCC TGC AAA AAA TGT GAT ATC AGT TGT    2544
Ser Ser Glu Asn Gly Tyr Lys Ser Cys Lys Lys Cys Asp Ile Ser Cys
830                 835                 840

TTG ACG TGC AAT GGC CCA GGA TTC AAG AAC TGT ACA AGC TGC CCT AGT    2592
Leu Thr Cys Asn Gly Pro Gly Phe Lys Asn Cys Thr Ser Cys Pro Ser
845                 850                 855                 860
```

```
GGG TAT CTC TTA GAC TTA GGA ATG TGT CAA ATG GGA GCC ATT TGC AAG        2640
Gly Tyr Leu Leu Asp Leu Gly Met Cys Gln Met Gly Ala Ile Cys Lys
                865                 870                 875

GAT GCA ACG GAA GAG TCC TGG GCG GAA GGA GGC TTC TGT ATG CTT GTG        2688
Asp Ala Thr Glu Glu Ser Trp Ala Glu Gly Gly Phe Cys Met Leu Val
            880                 885                 890

AAA AAG AAC AAT CTG TGC CAA CGG AAG GTT CTT CAA CAA CTT TGC TGC        2736
Lys Lys Asn Asn Leu Cys Gln Arg Lys Val Leu Gln Gln Leu Cys Cys
        895                 900                 905

AAA ACA TGT ACA TTC CAA GGC TGAGCAGCC                                   2766
Lys Thr Cys Thr Phe Gln Gly
910                 915
```

(2) INFORMATION FOR SEQ ID NO:18:

(i) SEQUENCE CHARACTERISTICS:
        (A) LENGTH: 915 amino acids
        (B) TYPE: amino acid
        (D) TOPOLOGY: linear (ii) MOLECULE TYPE: protein (xi) SEQUENCE DESCRIPTION: SEQ ID NO:18:

```
Met Asp Trp Asp Trp Gly Asn Arg Cys Ser Arg Pro Gly Arg Arg Asp
1               5                   10                  15

Leu Leu Cys Val Leu Ala Leu Ala Gly Cys Leu Leu Pro Val Cys
            20                  25                  30

Arg Thr Arg Val Tyr Thr Asn His Trp Ala Val Lys Ile Ala Gly Gly
        35                  40                  45

Phe Ala Glu Ala Asp Arg Ile Ala Ser Lys Tyr Gly Phe Ile Asn Val
    50                  55                  60

Gly Gln Ile Gly Ala Leu Lys Asp Tyr Tyr His Phe Tyr His Ser Arg
65              70                  75                  80

Thr Ile Lys Arg Ser Val Leu Ser Ser Arg Gly Thr His Ser Phe Ile
                85                  90                  95

Ser Met Glu Pro Lys Val Glu Trp Ile Gln Gln Val Val Lys Lys
            100                 105                 110

Arg Thr Lys Arg Asp Tyr Asp Leu Ser His Ala Gln Ser Thr Tyr Phe
        115                 120                 125

Asn Asp Pro Lys Trp Pro Ser Met Trp Tyr Met His Cys Ser Asp Asn
130                 135                 140

Thr His Pro Cys Gln Ser Asp Met Asn Ile Glu Gly Ala Trp Lys Arg
145                 150                 155                 160

Gly Tyr Thr Gly Lys Asn Ile Val Val Thr Ile Leu Asp Asp Gly Ile
                165                 170                 175

Glu Arg Thr His Pro Asp Leu Met Gln Asn Tyr Asp Ala Leu Ala Ser
            180                 185                 190

Cys Asp Val Asn Gly Asn Asp Leu Asp Pro Met Pro Arg Tyr Asp Ala
        195                 200                 205

Ser Asn Glu Asn Lys His Gly Thr Arg Cys Ala Gly Glu Val Ala Ala
    210                 215                 220

Ala Ala Asn Asn Ser His Cys Thr Val Gly Ile Ala Phe Asn Ala Lys
225                 230                 235                 240

Ile Gly Gly Val Arg Met Leu Asp Gly Asp Val Thr Asp Met Val Glu
                245                 250                 255

Ala Lys Ser Val Ser Phe Asn Pro Gln His Val His Ile Tyr Ser Ala
            260                 265                 270
```

```
Ser Trp Gly Pro Asp Asp Gly Lys Thr Val Asp Gly Pro Ala Pro
        275                 280                 285

Leu Thr Arg Gln Ala Phe Glu Asn Gly Val Arg Met Gly Arg Arg Gly
290                 295                 300

Leu Gly Ser Val Phe Val Trp Ala Ser Gly Asn Gly Gly Arg Ser Lys
305                 310                 315                 320

Asp His Cys Ser Cys Asp Gly Tyr Thr Asn Ser Ile Tyr Thr Ile Ser
                325                 330                 335

Ile Ser Ser Thr Ala Glu Ser Gly Lys Lys Pro Trp Tyr Leu Glu Glu
                340                 345                 350

Cys Ser Ser Thr Leu Ala Thr Thr Tyr Ser Ser Gly Glu Ser Tyr Asp
            355                 360                 365

Lys Lys Ile Ile Thr Thr Asp Leu Arg Gln Arg Cys Thr Asp Asn His
370                 375                 380

Thr Gly Thr Ser Ala Ser Ala Pro Met Ala Ala Gly Ile Ile Ala Leu
385                 390                 395                 400

Ala Leu Glu Ala Asn Pro Phe Leu Thr Trp Arg Asp Val Gln His Val
                405                 410                 415

Ile Val Arg Thr Ser Arg Ala Gly His Leu Asn Ala Asn Asp Trp Lys
                420                 425                 430

Thr Asn Ala Ala Gly Phe Lys Val Ser His Leu Tyr Gly Phe Gly Leu
            435                 440                 445

Met Asp Ala Glu Ala Met Val Met Glu Ala Glu Lys Trp Thr Thr Val
450                 455                 460

Pro Arg Gln His Val Cys Val Glu Ser Thr Asp Arg Gln Ile Lys Thr
465                 470                 475                 480

Ile Arg Pro Asn Ser Ala Val Arg Ser Ile Tyr Lys Ala Ser Gly Cys
                485                 490                 495

Ser Asp Asn Pro Asn Arg His Val Asn Tyr Leu Glu His Val Val Val
                500                 505                 510

Arg Ile Thr Ile Thr His Pro Arg Arg Gly Asp Leu Ala Ile Tyr Leu
                515                 520                 525

Thr Ser Pro Ser Gly Thr Arg Ser Gln Leu Leu Ala Asn Arg Leu Phe
            530                 535                 540

Asp His Ser Met Glu Gly Phe Lys Asn Trp Glu Phe Met Thr Ile His
545                 550                 555                 560

Cys Trp Gly Glu Arg Ala Ala Gly Asp Trp Val Leu Glu Val Tyr Asp
                565                 570                 575

Thr Pro Ser Gln Leu Arg Asn Phe Lys Thr Pro Gly Lys Leu Lys Glu
            580                 585                 590

Trp Ser Leu Val Leu Tyr Gly Thr Ser Val Arg Pro Tyr Ser Pro Thr
        595                 600                 605

Asn Glu Phe Pro Lys Val Glu Arg Phe Arg Tyr Ser Arg Val Glu Asp
610                 615                 620

Pro Thr Asp Asp Tyr Gly Thr Glu Asp Tyr Ala Gly Pro Cys Asp Pro
625                 630                 635                 640

Glu Cys Ser Glu Val Gly Cys Asp Gly Pro Gly Pro Asp His Cys Asn
                645                 650                 655

Asp Cys Leu His Tyr Tyr Lys Leu Lys Asn Asn Thr Arg Ile Cys
                660                 665                 670

Val Ser Ser Cys Pro Pro Gly His Tyr His Ala Asp Lys Lys Arg Cys
            675                 680                 685

Arg Lys Cys Ala Pro Asn Cys Glu Ser Cys Phe Gly Ser His Gly Asp
690                 695                 700
```

```
Gln Cys Met Ser Cys Lys Tyr Gly Tyr Phe Leu Asn Glu Thr Asn
705                 710                 715                 720

Ser Cys Val Thr His Cys Pro Asp Gly Ser Tyr Gln Asp Thr Lys Lys
            725                 730                 735

Asn Leu Cys Arg Lys Cys Ser Glu Asn Cys Lys Thr Cys Thr Glu Phe
                740                 745                 750

His Asn Cys Thr Glu Cys Arg Asp Gly Leu Ser Leu Gln Gly Ser Arg
            755                 760                 765

Cys Ser Val Ser Cys Glu Asp Gly Arg Tyr Phe Asn Gly Gln Asp Cys
        770                 775                 780

Gln Pro Cys His Arg Phe Cys Ala Thr Cys Ala Gly Ala Gly Ala Asp
785                 790                 795                 800

Gly Cys Ile Asn Cys Thr Glu Gly Tyr Phe Met Glu Asp Gly Arg Cys
                805                 810                 815

Val Gln Ser Cys Ser Ile Ser Tyr Tyr Phe Asp His Ser Ser Glu Asn
            820                 825                 830

Gly Tyr Lys Ser Cys Lys Lys Cys Asp Ile Ser Cys Leu Thr Cys Asn
                835                 840                 845

Gly Pro Gly Phe Lys Asn Cys Thr Ser Cys Pro Ser Gly Tyr Leu Leu
850                 855                 860

Asp Leu Gly Met Cys Gln Met Gly Ala Ile Cys Lys Asp Ala Thr Glu
865                 870                 875                 880

Glu Ser Trp Ala Glu Gly Gly Phe Cys Met Leu Val Lys Lys Asn Asn
                885                 890                 895

Leu Cys Gln Arg Lys Val Leu Gln Gln Leu Cys Cys Lys Thr Cys Thr
                900                 905                 910

Phe Gln Gly
        915

(2) INFORMATION FOR SEQ ID NO:19:

(i) SEQUENCE CHARACTERISTICS:
        (A) LENGTH: 2745 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:19:

ATGGATTGGG ATTGGGGGAA CCGCTGCAGC CGCCCGGGAC GGCGGGACCT GCTGTGCGTG      60

CTGGCACTGC TCGCCGGCTG TCTGCTCCCG GTATGCCGGA CGCGCGTCTA CACCAACCAC     120

TGGGCAGTGA AGATCGCCGG CGGCTTCGCG GAGGCAGATC GCATAGCCAG CAAGTACGGA     180

TTCATCAACG TAGGACAGAT CGGTGCACTG AAGGACTACT ATCACTTCTA CCATAGTAGG     240

ACCATTAAAA GGTCTGTTCT CTCGAGCAGA GGAACCCACA GTTTCATTTC AATGGAACCA     300

AAGGTGGAGT GGATCCAACA GCAAGTGGTG AAAAAAAGAA CCAAGAGGGA TTATGACCTC     360

AGCCATGCCC AGTCAACCTA CTTCAATGAT CCCAAGTGGC AAGTATGTGT GTACATGCAC     420

TGCAGTGACA ATACACATCC CTGCCAGTCT GACATGAATA TCGAAGGAGC CTGGAAGAGA     480

GGCTACACGG GAAAGAACAT TGTGGTCACT ATCCTGGATG ACGGAATTGA GAAACCCAT     540

CCAGATCTGA TGCAAAACTA CGATGCTCTG GCAAGTTGCG ACGTGAATGG GAATGACTTG     600

GACCCAATGC CTCGTTATGA TGCAAGCAAC GAGAACAAGC ATGGGACTCG CTGTGCTGGA     660

GAAGTGGCAG CCGCTGCAAA CAATTCGCAC TGCACAGTCG GAATTGCTTT CAACGCCAAG     720
```

```
ATCGGAGGAG TGCGAATGCT GGACGGAGAT GTCACGGACA TGGTTGAAGC AAAATCAGTT      780

AGCTTCAACC CCCAGCACGT GCACATTTAC AGCGCCAGCT GGGGCCCGGA TGATGATGGC      840

AAGACTGTGG ACGGACCAGC CCCCCTCACC CGGCAAGCCT TTGAAAACGG CGTTAGAATG      900

GGGCGGAGAG GCCTCGGCTC TGTGTTTGTT TGGGCATCTG GAAATGGTGG AAGGAGCAAA      960

GACCACTGCT CCTGTGATGG CTACACCAAC AGCATCTACA CCATCTCCAT CAGCAGCACT     1020

GCAGAAAGCG GAAAGAAACC TTGGTACCTG AAGAGTGTT CATCCACGCT GGCCACAACC     1080

TACAGCAGCG GGGAGTCCTA CGATAAGAAA ATCATCACTA CAGATCTGAG GCAGCGTTGC     1140

ACGGACAACC ACACTGGGAC GTCAGCCTCA GCCCCCATGG CTGCAGGCAT CATTGCGCTG     1200

GCCCTGGAAG CCAATCCGTT TCTGACCTGG AGAGACGTAC AGCATGTTAT TGTCAGGACT     1260

TCCCGTGCGG ACATTTGAA CGCTAATGAC TGGAAAACCA ATGCTGCTGG TTTTAAGGTG     1320

AGCCATCTTT ATGGATTTGG ACTGATGGAC GCAGAAGCCA TGGTGATGGA GGCAGAGAAG     1380

TGGACCACCG TTCCCCGGCA GCACGTGTGT GTGGAGAGCA CAGACCGACA AATCAAGACA     1440

ATCCGCCCTA ACAGTGCAGT GCGCTCCATC TACAAAGCTT CAGGCTGCTC GGATAACCCC     1500

AACCGCCATG TCAACTACCT GGAGCACGTC GTTGTGCGCA TCACCATCAC CCACCCCAGG     1560

AGAGGAGACC TGGCCATCTA CCTGACCTCG CCCTCTGGAA CTAGGTCTCA GCTTTTGGCC     1620

AACAGGCTAT TTGATCACTC CATGGAAGGA TTCAAAAACT GGGAGTTCAT GACCATTCAT     1680

TGCTGGGGAG AAAGAGCTGC TGGTGACTGG GTCCTTGAAG TTTATGATAC TCCCTCTCAG     1740

CTAAGGAACT TTAAGACTCC AGGTAAATTG AAAGAATGG CTTTGGTCCT CTACGGCACC     1800

TCCGTGCGGC CATATTCACC AACCAATGAA TTTCCGAAAG TGGAACGGTT CCGCTATAGC     1860

CGAGTTGAAG ACCCCACAGA CGACTATGGC ACAGAGGATT ATGCAGGTCC CTGCGACCCT     1920

GAGTGCAGTG AGGTTGGCTG TGACGGGCCA GGACCAGACC ACTGCAATGA CTGTTTGCAC     1980

TACTACTACA AGCTGAAAAA CAATACCAGG ATCTGTGTCT CCAGCTGCCC CCCTGGCCAC     2040

TACCACGCCG ACAAGAAGCG CTGCAGGAAG TGTGCCCCCA ACTGTGAGTC CTGCTTTGGG     2100

AGCCATGGTG ACCAATGCAT GTCCTGCAAA TATGGATACT TTCTGAATGA AGAAACCAAC     2160

AGCTGTGTTA CTCACTGCCC TGATGGGTCA TATCAGGATA CCAAGAAAAA TCTTTGCCGG     2220

AAATGCAGTG AAAACTGCAA GACATGTACT GAATTCCATA ACTGTACAGA ATGTAGGGAT     2280

GGGTTAAGCC TGCAGGGATC CCGGTGCTCT GTCTCCTGTG AAGATGGACG GTATTTCAAC     2340

GGCCAGGACT GCCAGCCCTG CCACCGCTTC TGCGCCACTT GTGCTGGGGC AGGAGCTGAT     2400

GGGTGCATTA ACTGCACAGA GGGCTACTTC ATGGAGGATG GGAGATGCGT GCAGAGCTGT     2460

AGTATCAGCT ATTACTTTGA CCACTCTTCA GAGAATGGAT ACAAATCCTG CAAAAAATGT     2520

GATATCAGTT GTTTGACGTG CAATGGCCCA GGATTCAAGA ACTGTACAAG CTGCCCTAGT     2580

GGGTATCTCT TAGACTTAGG AATGTGTCAA ATGGGAGCCA TTTGCAAGGA TGCAACGGAA     2640

GAGTCCTGGG CGGAAGGAGG CTTCTGTATG CTTGTGAAAA AGAACAATCT GTGCCAACGG     2700

AAGGTTCTTC AACAACTTTG CTGCAAAACA TGTACATTCC AAGGC                    2745
```

(2) INFORMATION FOR SEQ ID NO:20:

(i) SEQUENCE CHARACTERISTICS:
        (A) LENGTH: 2643 base pairs
        (B) TYPE: nucleic acid
        (C) STRANDEDNESS: single
        (D) TOPOLOGY: linear (ii) MOLECULE TYPE: cDNA (ix) FEATURE:

(A) NAME/KEY: CDS
(B) LOCATION: 1..2643

(xi) SEQUENCE DESCRIPTION: SEQ ID NO:20:

| | | | | | | | | | | | | | | | | |
|---|---|---|---|---|---|---|---|---|---|---|---|---|---|---|---|---|
| CGC | GTC | TAC | ACC | AAC | CAC | TGG | GCA | GTG | AAG | ATC | GCC | GGC | GGC | TTC | GCG | 48 |
| Arg | Val | Tyr | Thr | Asn | His | Trp | Ala | Val | Lys | Ile | Ala | Gly | Gly | Phe | Ala | |
| 1 | | | | 5 | | | | | 10 | | | | | 15 | | |
| GAG | GCA | GAT | CGC | ATA | GCC | AGC | AAG | TAC | GGA | TTC | ATC | AAC | GTA | GGA | CAG | 96 |
| Glu | Ala | Asp | Arg | Ile | Ala | Ser | Lys | Tyr | Gly | Phe | Ile | Asn | Val | Gly | Gln | |
| | | | 20 | | | | | 25 | | | | | 30 | | | |
| ATC | GGT | GCA | CTG | AAG | GAC | TAC | TAT | CAC | TTC | TAC | CAT | AGT | AGG | ACC | ATT | 144 |
| Ile | Gly | Ala | Leu | Lys | Asp | Tyr | Tyr | His | Phe | Tyr | His | Ser | Arg | Thr | Ile | |
| | | 35 | | | | | 40 | | | | | 45 | | | | |
| AAA | AGG | TCT | GTT | CTC | TCG | AGC | AGA | GGA | ACC | CAC | AGT | TTC | ATT | TCA | ATG | 192 |
| Lys | Arg | Ser | Val | Leu | Ser | Ser | Arg | Gly | Thr | His | Ser | Phe | Ile | Ser | Met | |
| | 50 | | | | | 55 | | | | | 60 | | | | | |
| GAA | CCA | AAG | GTG | GAG | TGG | ATC | CAA | CAG | CAA | GTG | GTG | AAA | AAA | AGA | ACC | 240 |
| Glu | Pro | Lys | Val | Glu | Trp | Ile | Gln | Gln | Gln | Val | Val | Lys | Lys | Arg | Thr | |
| 65 | | | | | 70 | | | | | 75 | | | | | 80 | |
| AAG | AGG | GAT | TAT | GAC | CTC | AGC | CAT | GCC | CAG | TCA | ACC | TAC | TTC | AAT | GAT | 288 |
| Lys | Arg | Asp | Tyr | Asp | Leu | Ser | His | Ala | Gln | Ser | Thr | Tyr | Phe | Asn | Asp | |
| | | | | 85 | | | | | 90 | | | | | 95 | | |
| CCC | AAG | TGG | CCA | AGT | ATG | TGG | TAC | ATG | CAC | TGC | AGT | GAC | AAT | ACA | CAT | 336 |
| Pro | Lys | Trp | Pro | Ser | Met | Trp | Tyr | Met | His | Cys | Ser | Asp | Asn | Thr | His | |
| | | | 100 | | | | | 105 | | | | | 110 | | | |
| CCC | TGC | CAG | TCT | GAC | ATG | AAT | ATC | GAA | GGA | GCC | TGG | AAG | AGA | GGC | TAC | 384 |
| Pro | Cys | Gln | Ser | Asp | Met | Asn | Ile | Glu | Gly | Ala | Trp | Lys | Arg | Gly | Tyr | |
| | | 115 | | | | | 120 | | | | | 125 | | | | |
| ACG | GGA | AAG | AAC | ATT | GTG | GTC | ACT | ATC | CTG | GAT | GAC | GGA | ATT | GAG | AGA | 432 |
| Thr | Gly | Lys | Asn | Ile | Val | Val | Thr | Ile | Leu | Asp | Asp | Gly | Ile | Glu | Arg | |
| | 130 | | | | | 135 | | | | | 140 | | | | | |
| ACC | CAT | CCA | GAT | CTG | ATG | CAA | AAC | TAC | GAT | GCT | CTG | GCA | AGT | TGC | GAC | 480 |
| Thr | His | Pro | Asp | Leu | Met | Gln | Asn | Tyr | Asp | Ala | Leu | Ala | Ser | Cys | Asp | |
| 145 | | | | | 150 | | | | | 155 | | | | | 160 | |
| GTG | AAT | GGG | AAT | GAC | TTG | GAC | CCA | ATG | CCT | CGT | TAT | GAT | GCA | AGC | AAC | 528 |
| Val | Asn | Gly | Asn | Asp | Leu | Asp | Pro | Met | Pro | Arg | Tyr | Asp | Ala | Ser | Asn | |
| | | | | 165 | | | | | 170 | | | | | 175 | | |
| GAG | AAC | AAG | CAT | GGG | ACT | CGC | TGT | GCT | GGA | GAA | GTG | GCA | GCC | GCT | GCA | 576 |
| Glu | Asn | Lys | His | Gly | Thr | Arg | Cys | Ala | Gly | Glu | Val | Ala | Ala | Ala | Ala | |
| | | | 180 | | | | | 185 | | | | | 190 | | | |
| AAC | AAT | TCG | CAC | TGC | ACA | GTC | GGA | ATT | GCT | TTC | AAC | GCC | AAG | ATC | GGA | 624 |
| Asn | Asn | Ser | His | Cys | Thr | Val | Gly | Ile | Ala | Phe | Asn | Ala | Lys | Ile | Gly | |
| | | 195 | | | | | 200 | | | | | 205 | | | | |
| GGA | GTG | CGA | ATG | CTG | GAC | GGA | GAT | GTC | ACG | GAC | ATG | GTT | GAA | GCA | AAA | 672 |
| Gly | Val | Arg | Met | Leu | Asp | Gly | Asp | Val | Thr | Asp | Met | Val | Glu | Ala | Lys | |
| | 210 | | | | | 215 | | | | | 220 | | | | | |
| TCA | GTT | AGC | TTC | AAC | CCC | CAG | CAC | GTG | CAC | ATT | TAC | AGC | GCC | AGC | TGG | 720 |
| Ser | Val | Ser | Phe | Asn | Pro | Gln | His | Val | His | Ile | Tyr | Ser | Ala | Ser | Trp | |
| 225 | | | | | 230 | | | | | 235 | | | | | 240 | |
| GGC | CCG | GAT | GAT | GAT | GGC | AAG | ACT | GTG | GAC | GGA | CCA | GCC | CCC | CTC | ACC | 768 |
| Gly | Pro | Asp | Asp | Asp | Gly | Lys | Thr | Val | Asp | Gly | Pro | Ala | Pro | Leu | Thr | |
| | | | | 245 | | | | | 250 | | | | | 255 | | |
| CGG | CAA | GCC | TTT | GAA | AAC | GGC | GTT | AGA | ATG | GGG | CGG | AGA | GGC | CTC | GGC | 816 |
| Arg | Gln | Ala | Phe | Glu | Asn | Gly | Val | Arg | Met | Gly | Arg | Arg | Gly | Leu | Gly | |
| | | | 260 | | | | | 265 | | | | | 270 | | | |
| TCT | GTG | TTT | GTT | TGG | GCA | TCT | GGA | AAT | GGT | GGA | AGG | AGC | AAA | GAC | CAC | 864 |
| Ser | Val | Phe | Val | Trp | Ala | Ser | Gly | Asn | Gly | Gly | Arg | Ser | Lys | Asp | His | |
| | | 275 | | | | | 280 | | | | | 285 | | | | |
| TGC | TCC | TGT | GAT | GGC | TAC | ACC | AAC | AGC | ATC | TAC | ACC | ATC | TCC | ATC | AGC | 912 |
| Cys | Ser | Cys | Asp | Gly | Tyr | Thr | Asn | Ser | Ile | Tyr | Thr | Ile | Ser | Ile | Ser | |
| | 290 | | | | | 295 | | | | | 300 | | | | | |

```
AGC ACT GCA GAA AGC GGA AAG AAA CCT TGG TAC CTG GAA GAG TGT TCA        960
Ser Thr Ala Glu Ser Gly Lys Lys Pro Trp Tyr Leu Glu Glu Cys Ser
305                 310                 315                 320

TCC ACG CTG GCC ACA ACC TAC AGC AGC GGG GAG TCC TAC GAT AAG AAA       1008
Ser Thr Leu Ala Thr Thr Tyr Ser Ser Gly Glu Ser Tyr Asp Lys Lys
                325                 330                 335

ATC ATC ACT ACA GAT CTG AGG CAG CGT TGC ACG GAC AAC CAC ACT GGG       1056
Ile Ile Thr Thr Asp Leu Arg Gln Arg Cys Thr Asp Asn His Thr Gly
            340                 345                 350

ACG TCA GCC TCA GCC CCC ATG GCT GCA GGC ATC ATT GCG CTG GCC CTG       1104
Thr Ser Ala Ser Ala Pro Met Ala Ala Gly Ile Ile Ala Leu Ala Leu
        355                 360                 365

GAA GCC AAT CCG TTT CTG ACC TGG AGA GAC GTA CAG CAT GTT ATT GTC       1152
Glu Ala Asn Pro Phe Leu Thr Trp Arg Asp Val Gln His Val Ile Val
370                 375                 380

AGG ACT TCC CGT GCG GGA CAT TTG AAC GCT AAT GAC TGG AAA ACC AAT       1200
Arg Thr Ser Arg Ala Gly His Leu Asn Ala Asn Asp Trp Lys Thr Asn
385                 390                 395                 400

GCT GCT GGT TTT AAG GTG AGC CAT CTT TAT GGA TTT GGA CTG ATG GAC       1248
Ala Ala Gly Phe Lys Val Ser His Leu Tyr Gly Phe Gly Leu Met Asp
                405                 410                 415

GCA GAA GCC ATG GTG ATG GAG GCA GAG AAG TGG ACC ACC GTT CCC CGG       1296
Ala Glu Ala Met Val Met Glu Ala Glu Lys Trp Thr Thr Val Pro Arg
            420                 425                 430

CAG CAC GTG TGT GTG GAG AGC ACA GAC CGA CAA ATC AAG ACA ATC CGC       1344
Gln His Val Cys Val Glu Ser Thr Asp Arg Gln Ile Lys Thr Ile Arg
        435                 440                 445

CCT AAC AGT GCA GTG CGC TCC ATC TAC AAA GCT TCA GGC TGC TCG GAT       1392
Pro Asn Ser Ala Val Arg Ser Ile Tyr Lys Ala Ser Gly Cys Ser Asp
450                 455                 460

AAC CCC AAC CGC CAT GTC AAC TAC CTG GAG CAC GTC GTT GTG CGC ATC       1440
Asn Pro Asn Arg His Val Asn Tyr Leu Glu His Val Val Val Arg Ile
465                 470                 475                 480

ACC ATC ACC CAC CCC AGG AGA GGA GAC CTG GCC ATC TAC CTG ACC TCG       1488
Thr Ile Thr His Pro Arg Arg Gly Asp Leu Ala Ile Tyr Leu Thr Ser
                485                 490                 495

CCC TCT GGA ACT AGG TCT CAG CTT TTG GCC AAC AGG CTA TTT GAT CAC       1536
Pro Ser Gly Thr Arg Ser Gln Leu Leu Ala Asn Arg Leu Phe Asp His
            500                 505                 510

TCC ATG GAA GGA TTC AAA AAC TGG GAG TTC ATG ACC ATT CAT TGC TGG       1584
Ser Met Glu Gly Phe Lys Asn Trp Glu Phe Met Thr Ile His Cys Trp
        515                 520                 525

GGA GAA AGA GCT GCT GGT GAC TGG GTC CTT GAA GTT TAT GAT ACT CCC       1632
Gly Glu Arg Ala Ala Gly Asp Trp Val Leu Glu Val Tyr Asp Thr Pro
                535                 540

TCT CAG CTA AGG AAC TTT AAG ACT CCA GGT AAA TTG AAA GAA TGG TCT       1680
Ser Gln Leu Arg Asn Phe Lys Thr Pro Gly Lys Leu Lys Glu Trp Ser
545                 550                 555                 560

TTG GTC CTC TAC GGC ACC TCC GTG CGG CCA TAT TCA CCA ACC AAT GAA       1728
Leu Val Leu Tyr Gly Thr Ser Val Arg Pro Tyr Ser Pro Thr Asn Glu
                565                 570                 575

TTT CCG AAA GTG GAA CGG TTC CGC TAT AGC CGA GTT GAA GAC CCC ACA       1776
Phe Pro Lys Val Glu Arg Phe Arg Tyr Ser Arg Val Glu Asp Pro Thr
            580                 585                 590

GAC GAC TAT GGC ACA GAG GAT TAT GCA GGT CCC TGC GAC CCT GAG TGC       1824
Asp Asp Tyr Gly Thr Glu Asp Tyr Ala Gly Pro Cys Asp Pro Glu Cys
        595                 600                 605

AGT GAG GTT GGC TGT GAC GGG CCA GGA CCA GAC CAC TGC AAT GAC TGT       1872
Ser Glu Val Gly Cys Asp Gly Pro Gly Pro Asp His Cys Asn Asp Cys
            610                 615                 620
```

```
TTG CAC TAC TAC TAC AAG CTG AAA AAC AAT ACC AGG ATC TGT GTC TCC           1920
Leu His Tyr Tyr Tyr Lys Leu Lys Asn Asn Thr Arg Ile Cys Val Ser
625                 630                 635                 640

AGC TGC CCC CCT GGC CAC TAC CAC GCC GAC AAG AAG CGC TGC AGG AAG           1968
Ser Cys Pro Pro Gly His Tyr His Ala Asp Lys Lys Arg Cys Arg Lys
                    645                 650                 655

TGT GCC CCC AAC TGT GAG TCC TGC TTT GGG AGC CAT GGT GAC CAA TGC           2016
Cys Ala Pro Asn Cys Glu Ser Cys Phe Gly Ser His Gly Asp Gln Cys
                660                 665                 670

ATG TCC TGC AAA TAT GGA TAC TTT CTG AAT GAA GAA ACC AAC AGC TGT           2064
Met Ser Cys Lys Tyr Gly Tyr Phe Leu Asn Glu Glu Thr Asn Ser Cys
            675                 680                 685

GTT ACT CAC TGC CCT GAT GGG TCA TAT CAG GAT ACC AAG AAA AAT CTT           2112
Val Thr His Cys Pro Asp Gly Ser Tyr Gln Asp Thr Lys Lys Asn Leu
        690                 695                 700

TGC CGG AAA TGC AGT GAA AAC TGC AAG ACA TGT ACT GAA TTC CAT AAC           2160
Cys Arg Lys Cys Ser Glu Asn Cys Lys Thr Cys Thr Glu Phe His Asn
    705                 710                 715                 720

TGT ACA GAA TGT AGG GAT GGG TTA AGC CTG CAG GGA TCC CGG TGC TCT           2208
Cys Thr Glu Cys Arg Asp Gly Leu Ser Leu Gln Gly Ser Arg Cys Ser
                    725                 730                 735

GTC TCC TGT GAA GAT GGA CGG TAT TTC AAC GGC CAG GAC TGC CAG CCC           2256
Val Ser Cys Glu Asp Gly Arg Tyr Phe Asn Gly Gln Asp Cys Gln Pro
                740                 745                 750

TGC CAC CGC TTC TGC GCC ACT TGT GCT GGG GCA GGA GCT GAT GGG TGC           2304
Cys His Arg Phe Cys Ala Thr Cys Ala Gly Ala Gly Ala Asp Gly Cys
            755                 760                 765

ATT AAC TGC ACA GAG GGC TAC TTC ATG GAG GAT GGG AGA TGC GTG CAG           2352
Ile Asn Cys Thr Glu Gly Tyr Phe Met Glu Asp Gly Arg Cys Val Gln
        770                 775                 780

AGC TGT AGT ATC AGC TAT TAC TTT GAC CAC TCT TCA GAG AAT GGA TAC           2400
Ser Cys Ser Ile Ser Tyr Tyr Phe Asp His Ser Ser Glu Asn Gly Tyr
785                 790                 795                 800

AAA TCC TGC AAA AAA TGT GAT ATC AGT TGT TTG ACG TGC AAT GGC CCA           2448
Lys Ser Cys Lys Lys Cys Asp Ile Ser Cys Leu Thr Cys Asn Gly Pro
                    805                 810                 815

GGA TTC AAG AAC TGT ACA AGC TGC CCT AGT GGG TAT CTC TTA GAC TTA           2496
Gly Phe Lys Asn Cys Thr Ser Cys Pro Ser Gly Tyr Leu Leu Asp Leu
                820                 825                 830

GGA ATG TGT CAA ATG GGA GCC ATT TGC AAG GAT GCA ACG GAA GAG TCC           2544
Gly Met Cys Gln Met Gly Ala Ile Cys Lys Asp Ala Thr Glu Glu Ser
            835                 840                 845

TGG GCG GAA GGA GGC TTC TGT ATG CTT GTG AAA AAG AAC AAT CTG TGC           2592
Trp Ala Glu Gly Gly Phe Cys Met Leu Val Lys Lys Asn Asn Leu Cys
        850                 855                 860

CAA CGG AAG GTT CTT CAA CAA CTT TGC TGC AAA ACA TGT ACA TTC CAA           2640
Gln Arg Lys Val Leu Gln Gln Leu Cys Cys Lys Thr Cys Thr Phe Gln
865                 870                 875                 880

GGC                                                                       2643
Gly
```

(2) INFORMATION FOR SEQ ID NO:21:

(i) SEQUENCE CHARACTERISTICS:
        (A) LENGTH: 881 amino acids
        (B) TYPE: amino acid
        (D) TOPOLOGY: linear (ii) MOLECULE TYPE: protein (xi) SEQUENCE DESCRIPTION: SEQ ID NO:21:

```
Arg Val Tyr Thr Asn His Trp Ala Val Lys Ile Ala Gly Gly Phe Ala
  1               5                  10                  15

Glu Ala Asp Arg Ile Ala Ser Lys Tyr Gly Phe Ile Asn Val Gly Gln
                 20                  25                  30

Ile Gly Ala Leu Lys Asp Tyr Tyr His Phe Tyr His Ser Arg Thr Ile
             35                  40                  45

Lys Arg Ser Val Leu Ser Ser Arg Gly Thr His Ser Phe Ile Ser Met
 50                  55                  60

Glu Pro Lys Val Glu Trp Ile Gln Gln Val Val Lys Lys Arg Thr
 65                  70                  75                  80

Lys Arg Asp Tyr Asp Leu Ser His Ala Gln Ser Thr Tyr Phe Asn Asp
                 85                  90                  95

Pro Lys Trp Pro Ser Met Trp Tyr Met His Cys Ser Asp Asn Thr His
                100                 105                 110

Pro Cys Gln Ser Asp Met Asn Ile Glu Gly Ala Trp Lys Arg Gly Tyr
                115                 120                 125

Thr Gly Lys Asn Ile Val Val Thr Ile Leu Asp Asp Gly Ile Glu Arg
130                 135                 140

Thr His Pro Asp Leu Met Gln Asn Tyr Asp Ala Leu Ala Ser Cys Asp
145                 150                 155                 160

Val Asn Gly Asn Asp Leu Asp Pro Met Pro Arg Tyr Asp Ala Ser Asn
                165                 170                 175

Glu Asn Lys His Gly Thr Arg Cys Ala Gly Glu Val Ala Ala Ala Ala
                180                 185                 190

Asn Asn Ser His Cys Thr Val Gly Ile Ala Phe Asn Ala Lys Ile Gly
                195                 200                 205

Gly Val Arg Met Leu Asp Gly Asp Val Thr Asp Met Val Glu Ala Lys
210                 215                 220

Ser Val Ser Phe Asn Pro Gln His Val His Ile Tyr Ser Ala Ser Trp
225                 230                 235                 240

Gly Pro Asp Asp Asp Gly Lys Thr Val Asp Gly Pro Ala Pro Leu Thr
                245                 250                 255

Arg Gln Ala Phe Glu Asn Gly Val Arg Met Gly Arg Arg Gly Leu Gly
                260                 265                 270

Ser Val Phe Val Trp Ala Ser Gly Asn Gly Gly Arg Ser Lys Asp His
            275                 280                 285

Cys Ser Cys Asp Gly Tyr Thr Asn Ser Ile Tyr Thr Ile Ser Ile Ser
290                 295                 300

Ser Thr Ala Glu Ser Gly Lys Lys Pro Trp Tyr Leu Glu Glu Cys Ser
305                 310                 315                 320

Ser Thr Leu Ala Thr Thr Tyr Ser Ser Gly Glu Ser Tyr Asp Lys Lys
                325                 330                 335

Ile Ile Thr Thr Asp Leu Arg Gln Arg Cys Thr Asp Asn His Thr Gly
                340                 345                 350

Thr Ser Ala Ser Ala Pro Met Ala Ala Gly Ile Ile Ala Leu Ala Leu
            355                 360                 365

Glu Ala Asn Pro Phe Leu Thr Trp Arg Asp Val Gln His Val Ile Val
370                 375                 380

Arg Thr Ser Arg Ala Gly His Leu Asn Ala Asn Asp Trp Lys Thr Asn
385                 390                 395                 400

Ala Ala Gly Phe Lys Val Ser His Leu Tyr Gly Phe Gly Leu Met Asp
                405                 410                 415

Ala Glu Ala Met Val Met Glu Ala Glu Lys Trp Thr Thr Val Pro Arg
                420                 425                 430
```

-continued

```
Gln His Val Cys Val Glu Ser Thr Asp Arg Gln Ile Lys Thr Ile Arg
        435                 440                 445

Pro Asn Ser Ala Val Arg Ser Ile Tyr Lys Ala Ser Gly Cys Ser Asp
    450                 455                 460

Asn Pro Asn Arg His Val Asn Tyr Leu Glu His Val Val Arg Ile
465                 470                 475                 480

Thr Ile Thr His Pro Arg Arg Gly Asp Leu Ala Ile Tyr Leu Thr Ser
                    485                 490                 495

Pro Ser Gly Thr Arg Ser Gln Leu Leu Ala Asn Arg Leu Phe Asp His
            500                 505                 510

Ser Met Glu Gly Phe Lys Asn Trp Glu Phe Met Thr Ile His Cys Trp
        515                 520                 525

Gly Glu Arg Ala Ala Gly Asp Trp Val Leu Glu Val Tyr Asp Thr Pro
        530                 535                 540

Ser Gln Leu Arg Asn Phe Lys Thr Pro Gly Lys Leu Lys Glu Trp Ser
545                 550                 555                 560

Leu Val Leu Tyr Gly Thr Ser Val Arg Pro Tyr Ser Pro Thr Asn Glu
                565                 570                 575

Phe Pro Lys Val Glu Arg Phe Arg Tyr Ser Arg Val Glu Asp Pro Thr
                580                 585                 590

Asp Asp Tyr Gly Thr Glu Asp Tyr Ala Gly Pro Cys Asp Pro Glu Cys
            595                 600                 605

Ser Glu Val Gly Cys Asp Gly Pro Gly Pro Asp His Cys Asn Asp Cys
        610                 615                 620

Leu His Tyr Tyr Tyr Lys Leu Lys Asn Asn Thr Arg Ile Cys Val Ser
625                 630                 635                 640

Ser Cys Pro Pro Gly His Tyr His Ala Asp Lys Lys Arg Cys Arg Lys
                645                 650                 655

Cys Ala Pro Asn Cys Glu Ser Cys Phe Gly Ser His Gly Asp Gln Cys
                660                 665                 670

Met Ser Cys Lys Tyr Gly Tyr Phe Leu Asn Glu Glu Thr Asn Ser Cys
        675                 680                 685

Val Thr His Cys Pro Asp Gly Ser Tyr Gln Asp Thr Lys Lys Asn Leu
        690                 695                 700

Cys Arg Lys Cys Ser Glu Asn Cys Lys Thr Cys Thr Glu Phe His Asn
705                 710                 715                 720

Cys Thr Glu Cys Arg Asp Gly Leu Ser Leu Gln Gly Ser Arg Cys Ser
                725                 730                 735

Val Ser Cys Glu Asp Gly Arg Tyr Phe Asn Gly Gln Asp Cys Gln Pro
                740                 745                 750

Cys His Arg Phe Cys Ala Thr Cys Ala Gly Ala Gly Ala Asp Gly Cys
        755                 760                 765

Ile Asn Cys Thr Glu Gly Tyr Phe Met Glu Asp Gly Arg Cys Val Gln
        770                 775                 780

Ser Cys Ser Ile Ser Tyr Tyr Phe Asp His Ser Ser Glu Asn Gly Tyr
785                 790                 795                 800

Lys Ser Cys Lys Lys Cys Asp Ile Ser Cys Leu Thr Cys Asn Gly Pro
                805                 810                 815

Gly Phe Lys Asn Cys Thr Ser Cys Pro Ser Gly Tyr Leu Leu Asp Leu
                820                 825                 830

Gly Met Cys Gln Met Gly Ala Ile Cys Lys Asp Ala Thr Glu Glu Ser
        835                 840                 845

Trp Ala Glu Gly Gly Phe Cys Met Leu Val Lys Lys Asn Asn Leu Cys
```

```
                  850               855               860
Gln Arg Lys Val Leu Gln Gln Leu Cys Cys Lys Thr Cys Thr Phe Gln
865                 870               875               880

Gly (2) INFORMATION FOR SEQ ID NO:22:

(i) SEQUENCE CHARACTERISTICS:
        (A) LENGTH: 2397 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..2397

(xi) SEQUENCE DESCRIPTION: SEQ ID NO:22:

GAT TAT GAC CTC AGC CAT GCC CAG TCA ACC TAC TTC AAT GAT CCC AAG       48
Asp Tyr Asp Leu Ser His Ala Gln Ser Thr Tyr Phe Asn Asp Pro Lys
  1               5                  10                  15

TGG CCA AGT ATG TGG TAC ATG CAC TGC AGT GAC AAT ACA CAT CCC TGC       96
Trp Pro Ser Met Trp Tyr Met His Cys Ser Asp Asn Thr His Pro Cys
             20                  25                  30

CAG TCT GAC ATG AAT ATC GAA GGA GCC TGG AAG AGA GGC TAC ACG GGA      144
Gln Ser Asp Met Asn Ile Glu Gly Ala Trp Lys Arg Gly Tyr Thr Gly
         35                  40                  45

AAG AAC ATT GTG GTC ACT ATC CTG GAT GAC GGA ATT GAG AGA ACC CAT      192
Lys Asn Ile Val Val Thr Ile Leu Asp Asp Gly Ile Glu Arg Thr His
     50                  55                  60

CCA GAT CTG ATG CAA AAC TAC GAT GCT CTG GCA AGT TGC GAC GTG AAT      240
Pro Asp Leu Met Gln Asn Tyr Asp Ala Leu Ala Ser Cys Asp Val Asn
 65                  70                  75                  80

GGG AAT GAC TTG GAC CCA ATG CCT CGT TAT GAT GCA AGC AAC GAG AAC      288
Gly Asn Asp Leu Asp Pro Met Pro Arg Tyr Asp Ala Ser Asn Glu Asn
                 85                  90                  95

AAG CAT GGG ACT CGC TGT GCT GGA GAA GTG GCA GCC GCT GCA AAC AAT      336
Lys His Gly Thr Arg Cys Ala Gly Glu Val Ala Ala Ala Ala Asn Asn
            100                 105                 110

TCG CAC TGC ACA GTC GGA ATT GCT TTC AAC GCC AAG ATC GGA GGA GTG      384
Ser His Cys Thr Val Gly Ile Ala Phe Asn Ala Lys Ile Gly Gly Val
        115                 120                 125

CGA ATG CTG GAC GGA GAT GTC ACG GAC ATG GTT GAA GCA AAA TCA GTT      432
Arg Met Leu Asp Gly Asp Val Thr Asp Met Val Glu Ala Lys Ser Val
    130                 135                 140

AGC TTC AAC CCC CAG CAC GTG CAC ATT TAC AGC GCC AGC TGG GGC CCG      480
Ser Phe Asn Pro Gln His Val His Ile Tyr Ser Ala Ser Trp Gly Pro
145                 150                 155                 160

GAT GAT GAT GGC AAG ACT GTG GAC GGA CCA GCC CCC CTC ACC CGG CAA      528
Asp Asp Asp Gly Lys Thr Val Asp Gly Pro Ala Pro Leu Thr Arg Gln
                165                 170                 175

GCC TTT GAA AAC GGC GTT AGA ATG GGC CGG AGA GGC CTC GGC TCT GTG      576
Ala Phe Glu Asn Gly Val Arg Met Gly Arg Arg Gly Leu Gly Ser Val
            180                 185                 190

TTT GTT TGG GCA TCT GGA AAT GGT GGA AGG AGC AAA GAC CAC TGC TCC      624
Phe Val Trp Ala Ser Gly Asn Gly Gly Arg Ser Lys Asp His Cys Ser
        195                 200                 205

TGT GAT GGC TAC ACC AAC AGC ATC TAC ACC ATC TCC ATC AGC AGC ACT      672
Cys Asp Gly Tyr Thr Asn Ser Ile Tyr Thr Ile Ser Ile Ser Ser Thr
    210                 215                 220
```

```
GCA GAA AGC GGA AAG AAA CCT TGG TAC CTG GAA GAG TGT TCA TCC ACG        720
Ala Glu Ser Gly Lys Lys Pro Trp Tyr Leu Glu Glu Cys Ser Ser Thr
225                 230                 235                 240

CTG GCC ACA ACC TAC AGC AGC GGG GAG TCC TAC GAT AAG AAA ATC ATC        768
Leu Ala Thr Thr Tyr Ser Ser Gly Glu Ser Tyr Asp Lys Lys Ile Ile
            245                 250                 255

ACT ACA GAT CTG AGG CAG CGT TGC ACG GAC AAC CAC ACT GGG ACG TCA        816
Thr Thr Asp Leu Arg Gln Arg Cys Thr Asp Asn His Thr Gly Thr Ser
                260                 265                 270

GCC TCA GCC CCC ATG GCT GCA GGC ATC ATT GCG CTG GCC CTG GAA GCC        864
Ala Ser Ala Pro Met Ala Ala Gly Ile Ile Ala Leu Ala Leu Glu Ala
            275                 280                 285

AAT CCG TTT CTG ACC TGG AGA GAC GTA CAG CAT GTT ATT GTC AGG ACT        912
Asn Pro Phe Leu Thr Trp Arg Asp Val Gln His Val Ile Val Arg Thr
        290                 295                 300

TCC CGT GCG GGA CAT TTG AAC GCT AAT GAC TGG AAA ACC AAT GCT GCT        960
Ser Arg Ala Gly His Leu Asn Ala Asn Asp Trp Lys Thr Asn Ala Ala
305                 310                 315                 320

GGT TTT AAG GTG AGC CAT CTT TAT GGA TTT GGA CTG ATG GAC GCA GAA       1008
Gly Phe Lys Val Ser His Leu Tyr Gly Phe Gly Leu Met Asp Ala Glu
            325                 330                 335

GCC ATG GTG ATG GAG GCA GAG AAG TGG ACC ACC GTT CCC CGG CAG CAC       1056
Ala Met Val Met Glu Ala Glu Lys Trp Thr Thr Val Pro Arg Gln His
                340                 345                 350

GTG TGT GTG GAG AGC ACA GAC CGA CAA ATC AAG ACA ATC CGC CCT AAC       1104
Val Cys Val Glu Ser Thr Asp Arg Gln Ile Lys Thr Ile Arg Pro Asn
            355                 360                 365

AGT GCA GTG CGC TCC ATC TAC AAA GCT TCA GGC TGC TCG GAT AAC CCC       1152
Ser Ala Val Arg Ser Ile Tyr Lys Ala Ser Gly Cys Ser Asp Asn Pro
        370                 375                 380

AAC CGC CAT GTC AAC TAC CTG GAG CAC GTC GTT GTG CGC ATC ACC ATC       1200
Asn Arg His Val Asn Tyr Leu Glu His Val Val Val Arg Ile Thr Ile
385                 390                 395                 400

ACC CAC CCC AGG AGA GGA GAC CTG GCC ATC TAC CTG ACC TCG CCC TCT       1248
Thr His Pro Arg Arg Gly Asp Leu Ala Ile Tyr Leu Thr Ser Pro Ser
            405                 410                 415

GGA ACT AGG TCT CAG CTT TTG GCC AAC AGG CTA TTT GAT CAC TCC ATG       1296
Gly Thr Arg Ser Gln Leu Leu Ala Asn Arg Leu Phe Asp His Ser Met
                420                 425                 430

GAA GGA TTC AAA AAC TGG GAG TTC ATG ACC ATT CAT TGC TGG GGA GAA       1344
Glu Gly Phe Lys Asn Trp Glu Phe Met Thr Ile His Cys Trp Gly Glu
            435                 440                 445

AGA GCT GCT GGT GAC TGG GTC CTT GAA GTT TAT GAT ACT CCC TCT CAG       1392
Arg Ala Ala Gly Asp Trp Val Leu Glu Val Tyr Asp Thr Pro Ser Gln
        450                 455                 460

CTA AGG AAC TTT AAG ACT CCA GGT AAA TTG AAA GAA TGG TCT TTG GTC       1440
Leu Arg Asn Phe Lys Thr Pro Gly Lys Leu Lys Glu Trp Ser Leu Val
465                 470                 475                 480

CTC TAC GGC ACC TCC GTG CGG CCA TAT TCA CCA ACC AAT GAA TTT CCG       1488
Leu Tyr Gly Thr Ser Val Arg Pro Tyr Ser Pro Thr Asn Glu Phe Pro
            485                 490                 495

AAA GTG GAA CGG TTC CGC TAT AGC CGA GTT GAA GAC CCC ACA GAC GAC       1536
Lys Val Glu Arg Phe Arg Tyr Ser Arg Val Glu Asp Pro Thr Asp Asp
                500                 505                 510

TAT GGC ACA GAG GAT TAT GCA GGT CCC TGC GAC CCT GAG TGC AGT GAG       1584
Tyr Gly Thr Glu Asp Tyr Ala Gly Pro Cys Asp Pro Glu Cys Ser Glu
            515                 520                 525

GTT GGC TGT GAC GGG CCA GGA CCA GAC CAC TGC AAT GAC TGT TTG CAC       1632
Val Gly Cys Asp Gly Pro Gly Pro Asp His Cys Asn Asp Cys Leu His
        530                 535                 540
```

```
TAC TAC TAC AAG CTG AAA AAC AAT ACC AGG ATC TGT GTC TCC AGC TGC        1680
Tyr Tyr Tyr Lys Leu Lys Asn Asn Thr Arg Ile Cys Val Ser Ser Cys
545             550                 555                 560

CCC CCT GGC CAC TAC CAC GCC GAC AAG AAG CGC TGC AGG AAG TGT GCC        1728
Pro Pro Gly His Tyr His Ala Asp Lys Lys Arg Cys Arg Lys Cys Ala
                565                 570                 575

CCC AAC TGT GAG TCC TGC TTT GGG AGC CAT GGT GAC CAA TGC ATG TCC        1776
Pro Asn Cys Glu Ser Cys Phe Gly Ser His Gly Asp Gln Cys Met Ser
                580                 585                 590

TGC AAA TAT GGA TAC TTT CTG AAT GAA GAA ACC AAC AGC TGT GTT ACT        1824
Cys Lys Tyr Gly Tyr Phe Leu Asn Glu Glu Thr Asn Ser Cys Val Thr
            595                 600                 605

CAC TGC CCT GAT GGG TCA TAT CAG GAT ACC AAG AAA AAT CTT TGC CGG        1872
His Cys Pro Asp Gly Ser Tyr Gln Asp Thr Lys Lys Asn Leu Cys Arg
            610                 615                 620

AAA TGC AGT GAA AAC TGC AAG ACA TGT ACT GAA TTC CAT AAC TGT ACA        1920
Lys Cys Ser Glu Asn Cys Lys Thr Cys Thr Glu Phe His Asn Cys Thr
625                 630                 635                 640

GAA TGT AGG GAT GGG TTA AGC CTG CAG GGA TCC CGG TGC TCT GTC TCC        1968
Glu Cys Arg Asp Gly Leu Ser Leu Gln Gly Ser Arg Cys Ser Val Ser
                645                 650                 655

TGT GAA GAT GGA CGG TAT TTC AAC GGC CAG GAC TGC CAG CCC TGC CAC        2016
Cys Glu Asp Gly Arg Tyr Phe Asn Gly Gln Asp Cys Gln Pro Cys His
                660                 665                 670

CGC TTC TGC GCC ACT TGT GCT GGG GCA GGA GCT GAT GGG TGC ATT AAC        2064
Arg Phe Cys Ala Thr Cys Ala Gly Ala Gly Ala Asp Gly Cys Ile Asn
            675                 680                 685

TGC ACA GAG GGC TAC TTC ATG GAG GAT GGG AGA TGC GTG CAG AGC TGT        2112
Cys Thr Glu Gly Tyr Phe Met Glu Asp Gly Arg Cys Val Gln Ser Cys
690                 695                 700

AGT ATC AGC TAT TAC TTT GAC CAC TCT TCA GAG AAT GGA TAC AAA TCC        2160
Ser Ile Ser Tyr Tyr Phe Asp His Ser Ser Glu Asn Gly Tyr Lys Ser
705                 710                 715                 720

TGC AAA AAA TGT GAT ATC AGT TGT TTG ACG TGC AAT GGC CCA GGA TTC        2208
Cys Lys Lys Cys Asp Ile Ser Cys Leu Thr Cys Asn Gly Pro Gly Phe
                725                 730                 735

AAG AAC TGT ACA AGC TGC CCT AGT GGG TAT CTC TTA GAC TTA GGA ATG        2256
Lys Asn Cys Thr Ser Cys Pro Ser Gly Tyr Leu Leu Asp Leu Gly Met
            740                 745                 750

TGT CAA ATG GGA GCC ATT TGC AAG GAT GCA ACG GAA GAG TCC TGG GCG        2304
Cys Gln Met Gly Ala Ile Cys Lys Asp Ala Thr Glu Glu Ser Trp Ala
            755                 760                 765

GAA GGA GGC TTC TGT ATG CTT GTG AAA AAG AAC AAT CTG TGC CAA CGG        2352
Glu Gly Gly Phe Cys Met Leu Val Lys Lys Asn Asn Leu Cys Gln Arg
770                 775                 780

AAG GTT CTT CAA CAA CTT TGC TGC AAA ACA TGT ACA TTC CAA GGC              2397
Lys Val Leu Gln Gln Leu Cys Cys Lys Thr Cys Thr Phe Gln Gly
785                 790                 795
```

(2) INFORMATION FOR SEQ ID NO:23:

(i) SEQUENCE CHARACTERISTICS:
        (A) LENGTH: 799 amino acids
        (B) TYPE: amino acid
        (D) TOPOLOGY: linear (ii) MOLECULE TYPE: protein (xi) SEQUENCE DESCRIPTION: SEQ ID NO:23:

```
Asp Tyr Asp Leu Ser His Ala Gln Ser Thr Tyr Phe Asn Asp Pro Lys
1               5                   10                  15

Trp Pro Ser Met Trp Tyr Met His Cys Ser Asp Asn Thr His Pro Cys
```

-continued

```
                    20                  25                  30
Gln Ser Asp Met Asn Ile Glu Gly Ala Trp Lys Arg Gly Tyr Thr Gly
        35                  40                  45
Lys Asn Ile Val Val Thr Ile Leu Asp Asp Gly Ile Glu Arg Thr His
 50                  55                  60
Pro Asp Leu Met Gln Asn Tyr Asp Ala Leu Ala Ser Cys Asp Val Asn
 65                  70                  75                  80
Gly Asn Asp Leu Asp Pro Met Pro Arg Tyr Asp Ala Ser Asn Glu Asn
                 85                  90                  95
Lys His Gly Thr Arg Cys Ala Gly Glu Val Ala Ala Ala Asn Asn
100                 105                 110
Ser His Cys Thr Val Gly Ile Ala Phe Asn Ala Lys Ile Gly Gly Val
        115                 120                 125
Arg Met Leu Asp Gly Asp Val Thr Asp Met Val Glu Ala Lys Ser Val
130                 135                 140
Ser Phe Asn Pro Gln His Val His Ile Tyr Ser Ala Ser Trp Gly Pro
145                 150                 155                 160
Asp Asp Asp Gly Lys Thr Val Asp Gly Pro Ala Pro Leu Thr Arg Gln
                165                 170                 175
Ala Phe Glu Asn Gly Val Arg Met Gly Arg Arg Gly Leu Gly Ser Val
        180                 185                 190
Phe Val Trp Ala Ser Gly Asn Gly Gly Arg Ser Lys Asp His Cys Ser
        195                 200                 205
Cys Asp Gly Tyr Thr Asn Ser Ile Tyr Thr Ile Ser Ile Ser Ser Thr
        210                 215                 220
Ala Glu Ser Gly Lys Lys Pro Trp Tyr Leu Glu Glu Cys Ser Ser Thr
225                 230                 235                 240
Leu Ala Thr Thr Tyr Ser Ser Gly Glu Ser Tyr Asp Lys Lys Ile Ile
                245                 250                 255
Thr Thr Asp Leu Arg Gln Arg Cys Thr Asp Asn His Thr Gly Thr Ser
                260                 265                 270
Ala Ser Ala Pro Met Ala Ala Gly Ile Ile Ala Leu Ala Leu Glu Ala
        275                 280                 285
Asn Pro Phe Leu Thr Trp Arg Asp Val Gln His Val Ile Val Arg Thr
290                 295                 300
Ser Arg Ala Gly His Leu Asn Ala Asn Asp Trp Lys Thr Asn Ala Ala
305                 310                 315                 320
Gly Phe Lys Val Ser His Leu Tyr Gly Phe Gly Leu Met Asp Ala Glu
                325                 330                 335
Ala Met Val Met Glu Ala Glu Lys Trp Thr Thr Val Pro Arg Gln His
        340                 345                 350
Val Cys Val Glu Ser Thr Asp Arg Gln Ile Lys Thr Ile Arg Pro Asn
        355                 360                 365
Ser Ala Val Arg Ser Ile Tyr Lys Ala Ser Gly Cys Ser Asp Asn Pro
370                 375                 380
Asn Arg His Val Asn Tyr Leu Glu His Val Val Val Arg Ile Thr Ile
385                 390                 395                 400
Thr His Pro Arg Arg Gly Asp Leu Ala Ile Tyr Leu Thr Ser Pro Ser
                405                 410                 415
Gly Thr Arg Ser Gln Leu Leu Ala Asn Arg Leu Phe Asp His Ser Met
                420                 425                 430
Glu Gly Phe Lys Asn Trp Glu Phe Met Thr Ile His Cys Trp Gly Glu
        435                 440                 445
```

```
Arg Ala Ala Gly Asp Trp Val Leu Glu Val Tyr Asp Thr Pro Ser Gln
450                 455                 460

Leu Arg Asn Phe Lys Thr Pro Gly Lys Leu Lys Glu Trp Ser Leu Val
465                 470                 475                 480

Leu Tyr Gly Thr Ser Val Arg Pro Tyr Ser Pro Thr Asn Glu Phe Pro
                485                 490                 495

Lys Val Glu Arg Phe Arg Tyr Ser Arg Val Glu Asp Pro Thr Asp Asp
                500                 505                 510

Tyr Gly Thr Glu Asp Tyr Ala Gly Pro Cys Asp Pro Glu Cys Ser Glu
                515                 520                 525

Val Gly Cys Asp Gly Pro Gly Pro Asp His Cys Asn Asp Cys Leu His
530                 535                 540

Tyr Tyr Tyr Lys Leu Lys Asn Asn Thr Arg Ile Cys Val Ser Ser Cys
545                 550                 555                 560

Pro Pro Gly His Tyr His Ala Asp Lys Lys Arg Cys Arg Lys Cys Ala
                565                 570                 575

Pro Asn Cys Glu Ser Cys Phe Gly Ser His Gly Asp Gln Cys Met Ser
                580                 585                 590

Cys Lys Tyr Gly Tyr Phe Leu Asn Glu Glu Thr Asn Ser Cys Val Thr
                595                 600                 605

His Cys Pro Asp Gly Ser Tyr Gln Asp Thr Lys Lys Asn Leu Cys Arg
610                 615                 620

Lys Cys Ser Glu Asn Cys Lys Thr Cys Thr Glu Phe His Asn Cys Thr
625                 630                 635                 640

Glu Cys Arg Asp Gly Leu Ser Leu Gln Gly Ser Arg Cys Ser Val Ser
                645                 650                 655

Cys Glu Asp Gly Arg Tyr Phe Asn Gly Gln Asp Cys Gln Pro Cys His
                660                 665                 670

Arg Phe Cys Ala Thr Cys Ala Gly Ala Gly Ala Asp Gly Cys Ile Asn
                675                 680                 685

Cys Thr Glu Gly Tyr Phe Met Glu Asp Gly Arg Cys Val Gln Ser Cys
690                 695                 700

Ser Ile Ser Tyr Tyr Phe Asp His Ser Ser Glu Asn Gly Tyr Lys Ser
705                 710                 715                 720

Cys Lys Lys Cys Asp Ile Ser Cys Leu Thr Cys Asn Gly Pro Gly Phe
                725                 730                 735

Lys Asn Cys Thr Ser Cys Pro Ser Gly Tyr Leu Leu Asp Leu Gly Met
                740                 745                 750

Cys Gln Met Gly Ala Ile Cys Lys Asp Ala Thr Glu Glu Ser Trp Ala
                755                 760                 765

Glu Gly Gly Phe Cys Met Leu Val Lys Lys Asn Asn Leu Cys Gln Arg
                770                 775                 780

Lys Val Leu Gln Gln Leu Cys Cys Lys Thr Cys Thr Phe Gln Gly
785                 790                 795
```

(2) INFORMATION FOR SEQ ID NO:24:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:24:

AGCGTNGGNA CNATGGAYTG GGAYTGG                                 27

(2) INFORMATION FOR SEQ ID NO:25:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:25:

```
RTTRTCRCTR CARTGCATRT ACCACAT                                            27
```

(2) INFORMATION FOR SEQ ID NO:26:

(i) SEQUENCE CHARACTERISTICS:
        (A) LENGTH: 1345 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:26:

```
CCTCGGCTCT GTGTTTGTTT GGGCATCTGG AAATGGTGGA AGGAGCAAAG ACCACTGCTC          60
CTGTGATGGC TACACCAACA GCATCTACAC CATCTCCATC AGCAGCACTG CAGAAAGCGG        120
AAAGAAACCT TGGTACCTGG AAGAGTGTTC ATCCACGCTG GCCACAACCT ACAGCAGCGG        180
GGAGTCCTAC GATAAGAAAA TCATCACTAC AGATCTGAGG CAGCGTTGCA CGGACAACCA        240
CACTGGGACG TCAGCCTCAG CCCCCATGGC TGCAGGCATC ATTGCGCTGG CCCTGGAAGC        300
CAATCCGTTT CTGACCTGGA GAGACGTACA GCATGTTATT GTCAGGACTT CCCGTGCGGG        360
ACATTTGAAC GCTAATGACT GGAAAACCAA TGCTGCTGGT TTTAAGGTGA GCCATCTTTA        420
TGGATTTGGA CTGATGGACG CAGAAGCCAT GGTGATGGAG GCAGAGAAGT GGACCACCGT        480
TCCCCGGCAG CACGTGTGTG TGGAGAGCAC AGACCGACAA ATCAAGACAA TCCGCCCTAA        540
CAGTGCAGTG CGCTCCATCT ACAAAGCTTC AGGCTGCTCG GATAACCCCA ACCGCCATGT        600
CAACTACCTG GAGCACGTCG TTGTGCGCAT CACCATCACC CACCCCAGGA GAGGAGACCT        660
GGCCATCTAC CTGACCTCGC CCTCTGGAAC TAGGTCTCAG CTTTTGGCCA ACAGGCTATT        720
TGATCACTCC ATGGAAGGAT TCAAAAACTG GGAGTTCATG ACCATTCATT GCTGGGGAGA        780
AAGAGCTGCT GGTGACTGGG TCCTTGAAGT TTATGATACT CCCTCTCAGC TAAGGAACTT        840
TAAGACTCCA GGTAAATTGA AGAATGGTC TTTGGTCCTC TACGGCACCT CCGTGCGGCC        900
ATATTCACCA ACCAATGAAT TTCCGAAAGT GGAACGGTTC CGCTATAGCC GAGTTGAAGA        960
CCCCACAGAC GACTATGGCA CAGAGGATTA TGCAGGTCCC TGCGACCCTG AGTGCAGTGA       1020
GGTTGGCTGT GACGGGCCAG GACCAGACCA CTGCAATGAC TGTTTGCACT ACTACTACAA       1080
GCTGAAAAAC AATACCAGGA TCTGTGTCTC CAGCTGCCCC CCTGGCCACT ACCACGCCGA       1140
CAAGAAGCGC TGCAGGAAGT GTGCCCCCAA CTGTGAGTCC TGCTTTGGGA GCCATGGTGA       1200
CCAATGCATG TCCTGCAAAT ATGGATACTT TCTGAATGAA GAAACCAACA GCTGTGTTAC       1260
TCACTGCCCT GATGGGTCAT ATCAGGATAC CAAGAAAAAT CTTTGCCGGA AATGCAGTGA       1320
AAACTGCAAG ACATGTACTG AATTC                                            1345
```

(2) INFORMATION FOR SEQ ID NO:27:

(i) SEQUENCE CHARACTERISTICS:
        (A) LENGTH: 1345 base pairs (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:27:

| | | | | | |
|---|---|---|---|---|---|
| GAATTCAGTA | CATGTCTTGC | AGTTTTCACT | GCATTTCCGG | CAAAGATTTT | TCTTGGTATC | 60 |
| CTGATATGAC | CCATCAGGGC | AGTGAGTAAC | ACAGCTGTTG | GTTTCTTCAT | TCAGAAAGTA | 120 |
| TCCATATTTG | CAGGACATGC | ATTGGTCACC | ATGGCTCCCA | AAGCAGGACT | CACAGTTGGG | 180 |
| GGCACACTTC | CTGCAGCGCT | TCTTGTCGGC | GTGGTAGTGG | CCAGGGGGGC | AGCTGGAGAC | 240 |
| ACAGATCCTG | GTATTGTTTT | TCAGCTTGTA | GTAGTAGTGC | AAACAGTCAT | TGCAGTGGTC | 300 |
| TGGTCCTGGC | CCGTCACAGC | CAACCTCACT | GCACTCAGGG | TCGCAGGGAC | CTGCATAATC | 360 |
| CTCTGTGCCA | TAGTCGTCTG | TGGGGTCTTC | AACTCGGCTA | TAGCGGAACC | GTTCCACTTT | 420 |
| CGGAAATTCA | TTGGTTGGTG | AATATGGCCG | CACGGAGGTG | CCGTAGAGGA | CCAAAGACCA | 480 |
| TTCTTTCAAT | TTACCTGGAG | TCTTAAAGTT | CCTTAGCTGA | GAGGGAGTAT | CATAAACTTC | 540 |
| AAGGACCCAG | TCACCAGCAG | CTCTTTCTCC | CCAGCAATGA | ATGGTCATGA | ACTCCCAGTT | 600 |
| TTTGAATCCT | TCCATGGAGT | GATCAAATAG | CCTGTTGGCC | AAAAGCTGAG | ACCTAGTTCC | 660 |
| AGAGGGCGAG | GTCAGGTAGA | TGGCCAGGTC | TCCTCTCCTG | GGGTGGGTGA | TGGTGATGCG | 720 |
| CACAACGACG | TGCTCCAGGT | AGTTGACATG | GCGGTTGGGG | TTATCCGAGC | AGCCTGAAGC | 780 |
| TTTGTAGATG | GAGCGCACTG | CACTGTTAGG | GCGGATTGTC | TTGATTTGTC | GGTCTGTGCT | 840 |
| CTCCACACAC | ACGTGCTGCC | GGGGAACGGT | GGTCCACTTC | TCTGCCTCCA | TCACCATGGC | 900 |
| TTCTGCGTCC | ATCAGTCCAA | ATCCATAAAG | ATGGCTCACC | TTAAAACCAG | CAGCATTGGT | 960 |
| TTTCCAGTCA | TTAGCGTTCA | AATGTCCCGC | ACGGGAAGTC | CTGACAATAA | CATGCTGTAC | 1020 |
| GTCTCTCCAG | GTCAGAAACG | GATTGGCTTC | CAGGGCCAGC | GCAATGATGC | CTGCAGCCAT | 1080 |
| GGGGGCTGAG | GCTGACGTCC | CAGTGTGGTT | GTCCGTGCAA | CGCTGCCTCA | GATCTGTAGT | 1140 |
| GATGATTTTC | TTATCGTAGG | ACTCCCCGCT | GCTGTAGGTT | GTGGCCAGCG | TGGATGAACA | 1200 |
| CTCTTCCAGG | TACCAAGGTT | TCTTTCCGCT | TTCTGCAGTG | CTGCTGATGG | AGATGGTGTA | 1260 |
| GATGCTGTTG | GTGTAGCCAT | CACAGGAGCA | GTGGTCTTTG | CTCCTTCCAC | CATTTCCAGA | 1320 |
| TGCCCAAACA | AACACAGAGC | CGAGG | | | | 1345 |

(2) INFORMATION FOR SEQ ID NO:28:

(i) SEQUENCE CHARACTERISTICS:
        (A) LENGTH: 2766 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:28:

| | | | | | |
|---|---|---|---|---|---|
| GGCTGCTCAG | CCTTGGAATG | TACATGTTTT | GCAGCAAAGT | TGTTGAAGAA | CCTTCCGTTG | 60 |
| GCACAGATTG | TTCTTTTTCA | CAAGCATACA | GAAGCCTCCT | TCCGCCCAGG | ACTCTTCCGT | 120 |
| TGCATCCTTG | CAAATGGCTC | CCATTTGACA | CATTCCTAAG | TCTAAGAGAT | ACCCACTAGG | 180 |
| GCAGCTTGTA | CAGTTCTTGA | ATCCTGGGCC | ATTGCACGTC | AAACAACTGA | TATCACATTT | 240 |
| TTTGCAGGAT | TTGTATCCAT | TCTCTGAAGA | GTGGTCAAAG | TAATAGCTGA | TACTACAGCT | 300 |
| CTGCACGCAT | CTCCCATCCT | CCATGAAGTA | GCCCTCTGTG | CAGTTAATGC | ACCCATCAGC | 360 |
| TCCTGCCCCA | GCACAAGTGG | CGCAGAAGCG | GTGGCAGGGC | TGGCAGTCCT | GGCCGTTGAA | 420 |

```
ATACCGTCCA TCTTCACAGG AGACAGAGCA CCGGGATCCC TGCAGGCTTA ACCCATCCCT    480

ACATTCTGTA CAGTTATGGA ATTCAGTACA TGTCTTGCAG TTTTCACTGC ATTTCCGGCA    540

AAGATTTTTC TTGGTATCCT GATATGACCC ATCAGGGCAG TGAGTAACAC AGCTGTTGGT    600

TTCTTCATTC AGAAAGTATC CATATTTGCA GGACATGCAT TGGTCACCAT GGCTCCCAAA    660

GCAGGACTCA CAGTTGGGGG CACACTTCCT GCAGCGCTTC TTGTCGGCGT GGTAGTGGCC    720

AGGGGGGCAG CTGGAGACAC AGATCCTGGT ATTGTTTTTC AGCTTGTAGT AGTAGTGCAA    780

ACAGTCATTG CAGTGGTCTG GTCCTGGCCC GTCACAGCCA ACCTCACTGC ACTCAGGGTC    840

GCAGGGACCT GCATAATCCT CTGTGCCATA GTCGTCTGTG GGGTCTTCAA CTCGGCTATA    900

GCGGAACCGT TCCACTTTCG GAAATTCATT GGTTGGTGAA TATGGCCGCA CGGAGGTGCC    960

GTAGAGGACC AAAGACCATT CTTTCAATTT ACCTGGAGTC TTAAAGTTCC TTAGCTGAGA   1020

GGGAGTATCA TAAACTTCAA GGACCCAGTC ACCAGCAGCT CTTTCTCCCC AGCAATGAAT   1080

GGTCATGAAC TCCCAGTTTT TGAATCCTTC CATGGAGTGA TCAAATAGCC TGTTGGCCAA   1140

AAGCTGAGAC CTAGTTCCAG AGGGCGAGGT CAGGTAGATG GCCAGGTCTC CTCTCCTGGG   1200

GTGGGTGATG GTGATGCGCA CAACGACGTG CTCCAGGTAG TTGACATGGC GGTTGGGGTT   1260

ATCCGAGCAG CCTGAAGCTT TGTAGATGGA GCGCACTGCA CTGTTAGGGC GGATTGTCTT   1320

GATTTGTCGG TCTGTGCTCT CCACACACAC GTGCTGCCGG GGAACGGTGG TCCACTTCTC   1380

TGCCTCCATC ACCATGGCTT CTGCGTCCAT CAGTCCAAAT CCATAAAGAT GGCTCACCTT   1440

AAAACCAGCA GCATTGGTTT TCCAGTCATT AGCGTTCAAA TGTCCCGCAC GGGAAGTCCT   1500

GACAATAACA TGCTGTACGT CTCTCCAGGT CAGAAACGGA TTGGCTTCCA GGGCCAGCGC   1560

AATGATGCCT GCAGCCATGG GGGCTGAGGC TGACGTCCCA GTGTGGTTGT CCGTGCAACG   1620

CTGCCTCAGA TCTGTAGTGA TGATTTTCTT ATCGTAGGAC TCCCCGCTGC TGTAGGTTGT   1680

GGCCAGCGTG GATGAACACT CTTCCAGGTA CCAAGGTTTC TTTCCGCTTT CTGCAGTGCT   1740

GCTGATGGAG ATGGTGTAGA TGCTGTTGGT GTAGCCATCA CAGGAGCAGT GGTCTTTGCT   1800

CCTTCCACCA TTTCCAGATG CCCAAACAAA CACAGAGCCG AGGCCTCTCC GCCCCATTCT   1860

AACGCCGTTT TCAAAGGCTT GCCGGGTGAG GGGGCTGGT CCGTCCACAG TCTTGCCATC   1920

ATCATCCGGG CCCCAGCTGG CGCTGTAAAT GTGCACGTGC TGGGGGTTGA AGCTAACTGA   1980

TTTTGCTTCA ACCATGTCCG TGACATCTCC GTCCAGCATT CGCACTCCTC CGATCTTGGC   2040

GTTGAAAGCA ATTCCGACTG TGCAGTGCGA ATTGTTTGCA GCGGCTGCCA CTTCTCCAGC   2100

ACAGCGAGTC CCATGCTTGT TCTCGTTGCT TGCATCATAA CGAGGCATTG GTCCAAGTC   2160

ATTCCCATTC ACGTCGCAAC TTGCCAGAGC ATCGTAGTTT TGCATCAGAT CTGGATGGGT   2220

TCTCTCAATT CCGTCATCCA GGATAGTGAC CACAATGTTC TTTCCCGTGT AGCCTCTCTT   2280

CCAGGCTCCT TCGATATTCA TGTCAGACTG GCAGGGATGT GTATTGTCGC TACAGTGCAT   2340

GTACCACATA CTTGGCCACT TGGGATCATT GAAGTAGGTT GACTGGGCAT GGCTGAGGTC   2400

ATAATCCCTC TTGGTTCTTT TTTTCACCAC TTGCTGTTGG ATCCACTCCA CCTTTGGTTC   2460

CATTGAAATG AAACTGTGGG TTCCTCTGCT CGAGAGAACA GACCTTTTAA TGGTCCTACT   2520

ATGGTAGAAG TGATAGTAGT CCTTCAGTGC ACCGATCTGT CCTACGTTGA TGAATCCGTA   2580

CTTGCTGGCT ATGCGATCTG CCTCCGCGAA GCCGCCGGCG ATCTTCACTG CCCAGTGGTT   2640

GGTGTAGACG CGCGTCCGGC ATACCGGGAG CAGACAGCCG GCGAGCAGTG CCAGCACGCA   2700

CAGCAGGTCC CGCCGTCCCG GGCGGCTGCA GCGGTTCCCC CAATCCCAAT CCATGGTCCC   2760

GACGCT                                                             2766
```

(2) INFORMATION FOR SEQ ID NO:29:

(i) SEQUENCE CHARACTERISTICS:
    (A) LENGTH: 20 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:29:

TGGGTGGTGG GTTTGAGATG                                          20

(2) INFORMATION FOR SEQ ID NO:30:

(i) SEQUENCE CHARACTERISTICS:
    (A) LENGTH: 20 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:30:

GGATGGGAGG TGGGTGGTGG                                          20

(2) INFORMATION FOR SEQ ID NO:31:

(i) SEQUENCE CHARACTERISTICS:
    (A) LENGTH: 20 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:31:

TTCATTGCAC TCAGCTAATG                                          20

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

What is claimed is:

1. An isolated nucleic acid molecule that selectively reduces expression of a dibasic amino acid processing endoprotease hTCP gene by hybridizing to a nucleic acid molecule selected from the group consisting of a dibasic amino acid processing endoprotease hTCP gene and transcription products thereof.

2. The nucleic acid molecule of claim 1, wherein said nucleic acid molecule reduces the infectivity of an infectious agent susceptible to inhibition of dibasic amino acid processing endoprotease activity.

3. The nucleic acid molecule of claim 2, wherein said nucleic acid molecule reduces the infectivity of an infectious agent susceptible to inhibition of dibasic amino acid processing endoprotease activity selected from the group consisting of hTCPA activity and hTCPB activity.

4. The nucleic acid molecule of claim 1, wherein said nucleic acid molecule hybridizes under stringent hybridization conditions with a nucleic acid molecule selected from the group consisting of $nhTCP_{483}$, $nhTCP_{\sim 2400}$ nhTCP, $nhTCP_{444}$, $nhTCP_{2766}$, $nhTCP_{2745}$, $nhTCP_{2643}$, $nhTCP_{1345}$, an approximately 0.7 kb fragment of the 3' end of $nhTCP_{1345}$, and $nhTCP_{2397}$.

5. The nucleic acid molecule of claim 1, wherein said nucleic acid molecule hybridizes with at least a portion of a nucleic acid molecule comprising a nucleic acid sequence selected from the group consisting of SEQ ID NO:17, SEQ ID NO:19, SEQ ID NO:20, SEQ ID NO:22, and SEQ ID NO:26.

6. The nucleic acid molecule of claim 1, wherein said nucleic acid molecule comprises at least a portion of a nucleic acid sequence selected from the group consisting of SEQ ID NO:27 and SEQ ID NO:28.

7. The nucleic acid molecule of claim 1, wherein said nucleic acid molecule comprises at least a portion of a nucleic acid sequence selected from the group consisting of SEQ ID NO:17, SEQ ID NO:19, SEQ ID NO:20, SEQ ID NO:22, and SEQ ID NO:26.

8. The nucleic acid molecule of claim 1, wherein said nucleic acid molecule hybridizes with a regulatory region of said dibasic amino acid processing endoprotease nhTCP gene.

9. An isolated nucleic acid molecule that reduces expression of a dibasic amino acid processing endoprotease hTCP gene to a greater degree as compared to its ability to reduce the expression of another dibasic amino acid processing endoprotease gene by hybridizing to a nucleic acid molecule selected from the group consisting of a dibasic amino acid processing endoprotease hTCP gene and transcription products thereof.

10. The isolated nucleic acid molecule of claim 9, wherein said nucleic acid molecule reduces expression of said dibasic amino acid processing endoprotease hTCP gene without reducing the expression of said another dibasic amino acid processing endoprotease gene by more than 50%.

11. A recombinant molecule comprising an isolated nucleic acid molecule as set forth in claim 1 operatively linked to a transcription control sequence.

12. A recombinant cell comprising an isolated nucleic acid molecule as set forth in claim 1.

13. A recombinant virus comprising an isolated nucleic acid molecule as set forth in claim 1.

14. An isolated nucleic acid molecule that hybridizes under stringent hybridization conditions with a regulatory region of a dibasic amino acid processing endoprotease gene comprising nhTCP.

15. The nucleic acid molecule of claim 14, wherein said nucleic acid molecule comprises an oligonucleotide.

16. The nucleic acid molecule of claim 14, wherein said regulatory region comprises an untranslated region.

17. The nucleic acid molecule of claim 14, wherein said nucleic acid molecule reduces the infectivity of an infectious agent susceptible to inhibition of dibasic amino acid processing endoprotease activity.

18. A recombinant molecule comprising an isolated nucleic acid molecule as set forth in claim 14 operatively linked to a transcription control sequence.

19. A recombinant cell comprising an isolated nucleic acid molecule as set forth in claim 14.

20. A recombinant virus comprising an isolated nucleic acid molecule as set forth in claim 14.

21. A therapeutic composition that reduces the infectivity of an infectious agent susceptible to inhibition of dibasic amino acid processing endoprotease activity, wherein said composition comprises a nucleic acid molecule that selectively reduces expression of a dibasic amino acid processing endoprotease hTCP gene by hybridizing to a nucleic acid molecule selected from the group consisting of a dibasic amino acid processing endoprotease hTCP gene and transcription products thereof, and an excipient.

22. The composition of claim 21, wherein said nucleic acid molecule hybridizes under stringent hybridization conditions, with a nucleic acid molecule selected from the group consisting of $nhTCP_{483}$, $nhTCP_{\sim 2400}$, $nhTCP$, $nhTCP_{444}$, $nhTCP_{2766}$, $nhTCP_{2745}$, $nhTCP_{2643}$, $nhTCP_{1345}$, an approximately 0.7 kb fragment of the 3' end of $nhTCP_{1345}$, and $nhTCP_{2397}$.

23. The composition of claim 21, wherein said infectious agent comprises an enveloped virus.

24. The composition of claim 21, wherein said infectious agent is selected from the group consisting of retroviruses, herpes viruses, hepadnaviruses, pox viruses, orthomyxoviruses, paramyxoviruses, rhabdoviruses, togaviruses, arena viruses, bunyaviruses and coronaviruses.

25. The composition of claim 21, wherein said infectious agent is selected from the group consisting of retroviruses, herpes viruses and hepadnaviruses.

26. The composition of claim 21, wherein said infectious agent comprises a retrovirus.

27. The composition of claim 21, wherein said infectious agent infects a cell that expresses a CD4+ cell marker on the surface of said cell.

28. The composition of claim 21, wherein said infectious agent is selected from the group consisting of lentiviruses and lymphotropic viruses.

29. The composition of claim 21, wherein said infectious agent is selected from the group consisting of HIV, FIV, SIV, CIV, HTLV, BLV and FLV.

30. The composition of claim 21, wherein said infectious agent comprises HIV.

31. A method to protect an animal from disease caused by an infectious agent susceptible to inhibition of dibasic amino acid processing endoprotease activity, said method comprising administering to said animal a therapeutic composition comprising a nucleic acid molecule that selectively reduces expression of a dibasic amino acid processing endoprotease hTCP gene by hybridizing to a nucleic acid molecule selected from the group consisting of a dibasic amino acid processing endoprotease hTCP gene and transcription products thereof.

32. The method of claim 31, wherein said composition further comprises an excipient.

33. The method of claim 31, wherein said animal is selected from the group consisting of mammals, birds, insects, amphibians and fish.

34. The method of claim 31, wherein said animal is selected from the group consisting of humans, apes, cats, dogs, cattle, horses, swine, sheep and monkeys.

35. A method to protect an animal from disease caused by an infectious agent susceptible to inhibition of dibasic amino acid processing endoprotease activity, said method comprising administering to said animal a therapeutic composition comprising a nucleic acid molecule that reduces expression of a dibasic amino acid processing endoprotease hTCP gene by hybridizing to a nucleic acid molecule selected from the group consisting of a regulatory region of a dibasic amino acid processing endoprotease hTCP gene, a coding region of a dibasic amino acid processing endoprotease hTCP gene, and transcription products of said dibasic amino acid processing endoprotease hTCP gene.

36. A method for reducing the infectivity of an infectious agent susceptible to inhibition of dibasic amino acid processing endoprotease activity in an animal, comprising administering to an animal an isolated nucleic acid molecule that selectively reduces expression of a dibasic amino acid processing endoprotease hTCP gene by hybridizing to a nucleic acid molecule selected from the group consisting of a dibasic amino acid processing endoprotease hTCP gene and transcription products thereof.

37. The method of claim 36, wherein said nucleic acid molecule hybridizes with a regulatory region of said dibasic amino acid processing endoprotease gene comprising nhTCP.

38. The method of claim 36, wherein said nucleic acid molecule is an oligonucleotide.

39. The method of claim 36, wherein said infectious agent comprises HIV.

40. A method for reducing expression of a dibasic amino acid processing endoprotease hTCP gene in an animal, comprising administering to said animal an isolated nucleic acid molecule that reduces expression of a dibasic amino acid processing endoprotease hTCP gene by hybridizing to a nucleic acid molecule selected from the group consisting of a dibasic amino acid processing endoprotease hTCP gene and transcription products thereof.

41. A method for reducing the infectivity of an infectious agent susceptible to inhibition of dibasic amino acid processing endoprotease activity in an animal, comprising administering to said animal an isolated nucleic acid molecule that reduces expression of a dibasic amino acid processing endoprotease hTCP gene by hybridizing to a nucleic acid molecule selected from the group consisting of a dibasic amino acid processing endoprotease hTCP gene regulatory region, a dibasic amino acid processing endoprotease hTCP gene coding region, and transcription products of said dibasic amino acid processing endoprotease hTCP gene.

* * * * *

UNITED STATES PATENT AND TRADEMARK OFFICE
CERTIFICATE OF CORRECTION

PATENT NO : 5,981,259
DATED : November 9, 1999
INVENTOR(S) : Franzusoff

It is certified that error appears in the above-identified patent and that said Letters Patent are hereby corrected as shown below:

In the "Related U.S. Application Data" [63], in lines 1 and 2 of the paragraph, please delete "Feb. 5, 1995" and insert –Jan. 5, 1995– therefor Signed and Sealed this Tenth Day of April, 2001

Attest:

NICHOLAS P. GODICI

Attesting Officer     Acting Director of the United States Patent and Trademark Office